US009422348B2

(12) United States Patent
Theisen et al.

(10) Patent No.: US 9,422,348 B2
(45) Date of Patent: Aug. 23, 2016

(54) PRODUCTION OF A CYSTEINE RICH PROTEIN

(71) Applicant: Statens Serum Institut, Copenhagen S (DK)

(72) Inventors: Michael Theisen, Nærum (DK); Gorm Andersen, Kastrup (DK)

(*) Notice: Subject to any disclaimer, the term of this patent is extended or adjusted under 35 U.S.C. 154(b) by 0 days.

(21) Appl. No.: 14/123,676

(22) PCT Filed: Oct. 3, 2012

(86) PCT No.: PCT/DK2012/000108
§ 371 (c)(1),
(2) Date: Dec. 3, 2013

(87) PCT Pub. No.: WO2013/050034
PCT Pub. Date: Apr. 11, 2013

(65) Prior Publication Data
US 2014/0170182 A1      Jun. 19, 2014

(30) Foreign Application Priority Data
Oct. 4, 2011  (DK) .................................. 2011 00765

(51) Int. Cl.
C12P 21/06        (2006.01)
C07K 14/445       (2006.01)
A61K 39/015       (2006.01)
C07K 14/47        (2006.01)
C12P 21/02        (2006.01)
C12N 15/62        (2006.01)
C12N 15/74        (2006.01)

(52) U.S. Cl.
CPC .............. *C07K 14/445* (2013.01); *A61K 39/015* (2013.01); *C07K 14/4718* (2013.01); *C12N 15/62* (2013.01); *C12N 15/746* (2013.01); *C12P 21/02* (2013.01); *C07K 2319/055* (2013.01)

(58) Field of Classification Search
None
See application file for complete search history.

(56) References Cited

FOREIGN PATENT DOCUMENTS

WO    WO 2004/043488 A1    5/2004

OTHER PUBLICATIONS

Raman et al (J.Biol. Chem. 1996. 271(29): 17067-17072).*
Seely et al (Chapter 16. Large Scale Refolding of Secretory Leukocyte Protease Inhibitor. 1991. ACS Symposium Series, Amer. Chem. Soc.), pp. 206-216).*
Vallego et al (Microbial Cell Factories. Sep. 2004. 3(11): 1-12).*
Bredmose, et al., Development of a heterologous gene expression system for use in *Lactococcus lactis*, p. 269-275, in Merten, et al., (ed.), Recombinant Protein Production with Prokaryotic and Eukaryotic Cells, Kluwer Academic Publishers, Netherlands, 2001.
Carter, et al., Two Apparently Nonrepeated Epitopes on Gametes of *Plasmodium falciuparum* Are Targets of Transmission-Blocking Antibodies, Infection and Immunity, Oct. 1985, 50(1):102-106.
Carter, et al., Properties of epitopes of Pfs 48/45, a target of transmission blocking monoclonal antibodies, on gametes of different isolates of *Plasmodium falciparum*, Parasite Immunology, Nov. 1990, 12(6):587-603.
Carter, Transmission blocking malaria vaccines, Vaccine, Mar. 21, 2011, 19(17-19):2309-2314.
Carvalho, et al., Immunization of *Saimiri sciureus* monkeys with a recombinant hybrid protein derived from the *Plasmodium falciparum* antigen glutamate-rich protein and merozoite surface protein 3 can induce partial protection with Freund and Montanide ISA720 adjuvants, Clinical and Diagnostic Laboratory Immunology, Feb. 2005, 12(2):242-248.
Cohen, et al., Gamma-globulin and acquired immunity to human malaria, Nature, Nov. 25, 1961, 192:733-737.
Gasson, Plasmid complements of *Streptococcus lactis* NCDO 712 and other lactic streptococci after protoplast-induced curing, J. Bacteriol., Apr. 1983, 154(1):1-9.
Gosselin, et al., Enhanced antigen presentation using human Fc gamma receptor (monocyte/macrophage)-specific immunogens, J. Immunol., Dec. 1, 1992, 149(11):3477-3481.
Holo, et al., Transformation of Lactococcus by electroporation, Methods in Molecular Biology, 1995, 47:195-199.
Israelsen, et al., Cloning and partial characterization of regulated promoters from Lactococcus lactis Tn917-lacZ integrants with the new promoter probe vector, pAK80, Appl. Environ. Microbiol., Jul. 1995, 61(7):2540-2547.
Kaslow, et al., Malaria transmission-blocking vaccines, Trends in Biotechnology, Nov. 1992, 10(11):388-391.
Kaslow, Transmission-blocking vaccines, Chem Immunol., 2002, 80:287-307.
Laemmli, Cleavage of structural proteins during the assembly of the head of bacteriophage T4, Nature, Aug. 15, 1970, 227(5259):680-685.
Le Loir, et al., A nine-residue synthetic propeptide enhances secretion efficiency of heterologous proteins in *Lactococcus lactis*, J. Bacteriol., Apr. 1998, 180(7):1895-1903.
Lowrie, et al., Therapy of tuberculosis in mice by DNA vaccination, Nature, Jul. 15, 1999, 400(6741):269-271.
Madsen, et al., Molecular characterization of the pH-inducible and growth phase-dependent promoter P170 of *Lactococcus lactis*, Mol Microbiol., Apr. 1999, 32(1):75-87.
Outchkourov, et al., Correctly folded Pfs48/45 protein of Plasmodium falciparum elicits malaria transmission-blocking immunity in mice, PNAS, Mar. 18, 2008, e-pub Mar. 10, 2008, 105(11):4301-4305.

(Continued)

*Primary Examiner* — Jennifer Graser
(74) *Attorney, Agent, or Firm* — Howson & Howson LLP

(57) ABSTRACT

The present invention relates to a method for the production of correctly folded Pfs48/45. This is achieved in the *lactococcus lactis* when Pfs48/45 or fractions thereof are fused genetically to a glutamate rich protein, e.g. GLURP from *Plasmodium falciparum*.

20 Claims, 9 Drawing Sheets

(56) References Cited

OTHER PUBLICATIONS

Figure 1:
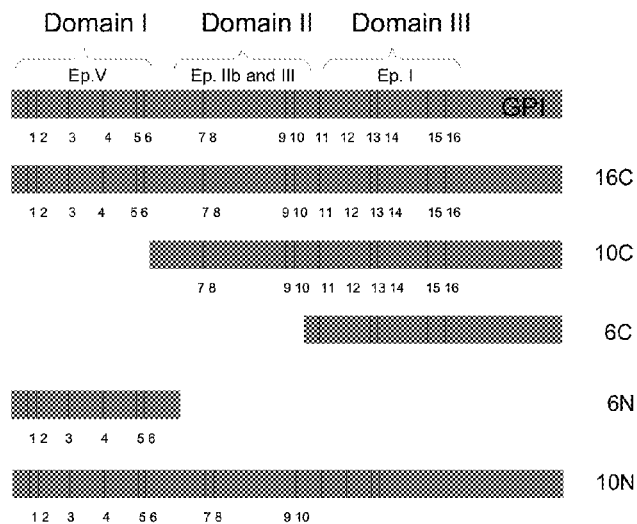

Outchkourov, et al., Epitope analysis of the malaria surface antigen pfs48/45 identifies a subdomain that elicits transmission blocking antibodies, J Biol Chem, Jun. 8, 2007, e-pub Apr. 9, 2007, 282(23):17148-17156.

Pedersen, et al., Genetic analysis of the minimal replicon of the *Lactococcus lactis* subsp. lactis biovar diacetylactis citrate plasmid, Mol Gen Genet., Aug. 15, 1994, 244(4):374-382.

Ravn, et al., Optimization of signal peptide SP310 for heterologous protein production in Lactococcus lactis, Microbiology, Aug. 2003, 149(Pt 8):2193-2201.

Rener, et al., Target antigens of transmission-blocking immunity on gametes of plasmodium falciparum, J Exp Med., Sep. 1, 1983, 158(3):976-981.

Roeffen, et al., A comparison of transmission-blocking activity with reactivity in a Plasmodium falciparum 48/45-kD molecule-specific competition enzyme-linked immunosorbent assay, Am J Trop Med Hyg., Jan. 1995, 52(1):60-65.

Roeffen, et al., Association between anti-Pfs48/45 reactivity and *P. falciparum* transmission-blocking activity in sera from Cameroon, Parasite Immunol., Feb. 1996, 18(2):103-109.

Roeffen, et al., Plasmodium falciparum: production and characterization of rat monoclonal antibodies specific for the sexual-stage Pfs48/45 antigen, Experimental Parasitology, Jan. 2001, 97(1):45-49.

Russell, et al., The Immunization of Fowls Against Mosquito-Borne Plasmodium Gallinaceum by Injections of Serum and of Inactivated Homologous Sporozoites, J Exp Med., Nov. 1, 1942, 76(5):477-495.

Simon, et al., Construction of a vector plasmid family and its use for molecular cloning in *Streptococcus lactis*, Biochimie, Apr. 1988, 70(4):559-566.

Targett, et al., Plasmodium falciparum sexual stage antigens: immunogenicity and cell-mediated responses, Immunol Lett., Aug. 1990, 25(1-3):77-81.

Theisen, et al., A Plasmodium falciparum GLURP-MSP3 chimeric protein; expression in Lactococcus lactis, immunogenicity and induction of biologically active antibodies, Vaccine, Mar. 12, 2004, 22(9-10):1188-1198.

van Dijk, et al., A central role for P48/45 in malaria parasite male gamete fertility, Cell, Jan. 12, 2001, 104(1):153-164.

Vermeulen, et al., Plasmodium falciparum transmission blocking monoclonal antibodies recognize monovalently expressed epitopes, Dev Biol Stand., 1985, 62:91-97.

Vermeulen, et al., Sequential expression of antigens on sexual stages of Plasmodium falciparum accessible to transmission-blocking antibodies in the mosquito, J Exp Med., Nov., 1985, 162(5):1460-1476.

World Health Organization, "Malaria", WHO Weekly Epidemiology Record No. 32, 1999, 74: 265-272, Geneva, Switzerland.

Nov. 11, 2013 International Preliminary Examination Report in international stage of present application (PCT/DK2012/000108).

Singh, S.K. et al., A Plasmodium falciparum 48/45 single epitope R0.6C subunit protein elicits high levels of transmission blocking antibodies, Vaccine, available online Feb. 26, 2015, 33: 1981-1986.

Theisen, M. et al., A multi-stage malaria vaccine candidate targeting both transmission and asexual parasite life-cycle stages, Vaccine, available online Mar. 21 2014, 32: 2623-2630.

* cited by examiner

SEQUENCE LISTING

<160> NUMBER OF SEQ ID NOS: 28

<210> SEQ ID NO 1
<211> LENGTH: 1271
<212> TYPE: PRT
<213> ORGANISM: Plasmodium falciparum

<400> SEQUENCE: 1

```
Met Arg Asn Leu Phe His Ile Thr Ile Cys Leu Val Thr Leu Asn Leu
1               5                   10                  15

Phe Ile Leu Glu Ile Ser Ala Lys Thr Asn Thr Ser Glu Asn Arg Asn
            20                  25                  30

Lys Arg Ile Gly Gly Pro Lys Leu Arg Gly Asn Val Thr Ser Asn Ile
        35                  40                  45

Lys Phe Pro Ser Asp Asn Lys Gly Lys Ile Ile Arg Gly Ser Asn Asp
    50                  55                  60

Lys Leu Asn Lys Asn Ser Glu Asp Val Leu Glu Gln Ser Glu Lys Ser
65                  70                  75                  80

Leu Val Ser Glu Asn Val Pro Ser Gly Leu Asp Ile Asp Asp Ile Pro
                85                  90                  95

Lys Glu Ser Ile Phe Ile Gln Glu Asp Gln Glu Gly Gln Thr His Ser
            100                 105                 110

Glu Leu Asn Pro Glu Thr Ser Glu His Ser Lys Asp Leu Asn Asn Asn
        115                 120                 125

Gly Ser Lys Asn Glu Ser Ser Asp Ile Ile Ser Glu Asn Asn Lys Ser
    130                 135                 140

Asn Lys Val Gln Asn His Phe Glu Ser Leu Ser Asp Leu Glu Leu Leu
145                 150                 155                 160

Glu Asn Ser Ser Gln Asp Asn Leu Asp Lys Asp Thr Ile Ser Thr Glu
                165                 170                 175

Pro Phe Pro Asn Gln Lys His Lys Asp Leu Gln Gln Asp Leu Asn Asp
            180                 185                 190

Glu Pro Leu Glu Pro Phe Pro Thr Gln Ile His Lys Asp Tyr Lys Glu
        195                 200                 205

Lys Asn Leu Ile Asn Glu Glu Asp Ser Glu Pro Phe Pro Arg Gln Lys
    210                 215                 220

His Lys Lys Val Asp Asn His Asn Glu Glu Lys Asn Val Phe His Glu
225                 230                 235                 240

Asn Gly Ser Ala Asn Gly Asn Gln Gly Ser Leu Lys Leu Lys Ser Phe
                245                 250                 255

Asp Glu His Leu Lys Asp Glu Lys Ile Glu Asn Glu Pro Leu Val His
```

```
                260                 265                 270
Glu Asn Leu Ser Ile Pro Asn Asp Pro Ile Glu Gln Ile Leu Asn Gln
            275                 280                 285

Pro Glu Gln Glu Thr Asn Ile Gln Glu Gln Leu Tyr Asn Glu Lys Gln
            290                 295                 300

Asn Val Glu Glu Lys Gln Asn Ser Gln Ile Pro Ser Leu Asp Leu Lys
305                 310                 315                 320

Glu Pro Thr Asn Glu Asp Ile Leu Pro Asn His Asn Pro Leu Glu Asn
                325                 330                 335

Ile Lys Gln Ser Glu Ser Glu Ile Asn His Val Gln Asp His Ala Leu
                340                 345                 350

Pro Lys Glu Asn Ile Ile Asp Lys Leu Asp Asn Gln Lys Glu His Ile
            355                 360                 365

Asp Gln Ser Gln His Asn Ile Asn Val Leu Gln Glu Asn Asn Ile Asn
            370                 375                 380

Asn His Gln Leu Glu Pro Gln Glu Lys Pro Asn Ile Glu Ser Phe Glu
385                 390                 395                 400

Pro Lys Asn Ile Asp Ser Glu Ile Ile Leu Pro Glu Asn Val Glu Thr
                405                 410                 415

Glu Glu Ile Ile Asp Asp Val Pro Ser Pro Lys His Ser Asn His Glu
                420                 425                 430

Thr Phe Glu Glu Glu Thr Ser Glu Ser Glu His Glu Glu Ala Val Ser
            435                 440                 445

Glu Lys Asn Ala His Glu Thr Val Glu His Glu Glu Thr Val Ser Gln
            450                 455                 460

Glu Ser Asn Pro Glu Lys Ala Asp Asn Asp Gly Asn Val Ser Gln Asn
465                 470                 475                 480

Ser Asn Asn Glu Leu Asn Glu Asn Glu Phe Val Glu Ser Glu Lys Ser
                485                 490                 495

Glu His Glu Ala Ala Glu Asn Glu Glu Ser Ser Leu Glu Glu Gly His
            500                 505                 510

His Glu Glu Ile Val Pro Glu Gln Asn Asn Glu Glu Ser Gly Glu Ser
            515                 520                 525

Lys Leu Val Asp Asn Asp Glu Gly Gly Phe Glu Glu Ala His His Glu
530                 535                 540

Asn Phe Ser Ser Glu Val Ser Asn Ser Glu Leu Asn Glu Asn Glu Phe
545                 550                 555                 560

Val Glu Ser Asp Lys Ser Val Thr Glu Pro Ala Glu His Glu Glu Val
                565                 570                 575

Val Ser Glu Glu Ser Asn Pro Glu Pro Ala Glu Asn Glu Glu Ser Ser
            580                 585                 590

Ile Glu Glu Ala His Gln Glu Glu Ile Val Pro Glu Gln Asn Asp Glu
            595                 600                 605

Glu Ser Gly Glu Ser Gly Leu Val Asp Asn Glu Glu Gly Asp Phe Glu
            610                 615                 620

Glu Pro Asn His Glu Glu Phe Glu Pro Asp Gln Asn Asp Ser Glu Leu
625                 630                 635                 640

Ser Glu Asn Glu Leu Val Glu Ser Glu Lys Ser Val Ser Glu Pro Ala
                645                 650                 655

Glu His Val Glu Ile Val Ser Glu Lys Ser Val Ser Glu Pro Ala Glu
            660                 665                 670

His Val Glu Ile Val Ser Glu Lys Ser Thr Ser Glu Pro Ala Glu His
            675                 680                 685
```

```
Val Glu Ser Val Ser Glu Gln Ser Asn Asn Glu Pro Ser Glu Lys Lys
            690                 695                 700

Asp Gly Pro Val Pro Ser Lys Pro Phe Glu Glu Ile Glu Lys Val Asp
705                 710                 715                 720

Val Gln Pro Lys Ile Val Asp Leu Gln Ile Ile Glu Pro Asn Phe Val
                725                 730                 735

Asp Ser Gln Pro Asn Pro Gln Glu Pro Val Glu Pro Ser Phe Val Lys
            740                 745                 750

Ile Glu Lys Val Pro Ser Glu Glu Asn Lys His Ala Ser Val Asp Pro
        755                 760                 765

Glu Val Lys Glu Lys Glu Asn Val Ser Glu Val Glu Glu Lys Gln
    770                 775                 780

Asn Ser Gln Glu Ser Val Glu Glu Ile Pro Val Asn Glu Asp Glu Phe
785                 790                 795                 800

Glu Asp Val His Thr Glu Gln Leu Asp Leu Asp His Lys Thr Val Asp
                805                 810                 815

Pro Glu Ile Val Glu Val Glu Ile Pro Ser Glu Leu His Glu Asn
                820                 825                 830

Glu Val Ala His Pro Glu Ile Val Glu Ile Glu Glu Val Phe Pro Glu
        835                 840                 845

Pro Asn Gln Asn Asn Glu Phe Gln Glu Ile Asn Glu Asp Asp Lys Ser
850                 855                 860

Ala His Ile Gln His Glu Ile Val Glu Val Glu Ile Leu Pro Glu
865                 870                 875                 880

Asp Asp Lys Asn Glu Lys Val Glu His Glu Ile Val Glu Val Glu Glu
                885                 890                 895

Ile Leu Pro Glu Asp Lys Asn Glu Lys Gly Gln His Glu Ile Val Glu
                900                 905                 910

Val Glu Glu Ile Leu Pro Glu Asp Asp Lys Asn Glu Lys Val Glu His
        915                 920                 925

Glu Ile Val Glu Val Glu Glu Ile Leu Pro Glu Asp Lys Asn Glu Lys
    930                 935                 940

Gly Gln His Glu Ile Val Glu Val Glu Glu Ile Leu Pro Glu Asp Lys
945                 950                 955                 960

Asn Glu Lys Val Glu His Glu Ile Val Glu Val Glu Glu Ile Leu Pro
                965                 970                 975

Glu Asp Lys Asn Glu Lys Gly Gln His Glu Ile Val Glu Val Glu Glu
            980                 985                 990

Ile Leu Pro Glu Asp Lys Asn Glu Lys Val Gln His Glu Ile Val Glu
        995                1000                1005

Val Glu Glu Ile Leu Pro Glu Asp Lys Asn Glu Lys Gly Gln His
    1010                1015                1020

Glu Ile Val Glu Val Glu Ile Leu Pro Glu Glu Asp Lys Asn
    1025                1030                1035

Glu Lys Gly Gln His Glu Ile Val Glu Val Glu Ile Leu Pro
    1040                1045                1050

Glu Asp Lys Asn Glu Lys Val Gln His Glu Ile Val Glu Val Glu
    1055                1060                1065

Glu Ile Leu Pro Glu Asp Lys Asn Glu Lys Val Gln His Glu Ile
        1070                1075                1080

Val Glu Val Glu Glu Ile Leu Pro Glu Ile Val Glu Ile Glu Glu
    1085                1090                1095
```

```
Val Pro Ser Gln Thr Asn Asn Asn Glu Asn Ile Glu Thr Ile Lys
    1100                1105                1110

Pro Glu Glu Lys Lys Asn Glu Phe Ser Val Glu Glu Lys Ala Ile
    1115                1120                1125

Pro Gln Glu Pro Val Val Pro Thr Leu Asn Glu Asn Glu Asn Val
    1130                1135                1140

Thr Pro Lys Pro Ser Glu Gly Glu Ser Thr Lys Pro Asp Ile Val
    1145                1150                1155

Gln Ile Lys Ile Val Gln Glu Asn Lys Pro Asn Lys Lys Glu Thr
    1160                1165                1170

Pro Val Val Asp Gly Pro Lys His Val Glu Gln Asn Ile Gln Glu
    1175                1180                1185

Asp Asp Asn Asp Glu Glu Asp Asp Asp Ile Asp Phe Glu Gly
    1190                1195                1200

Leu Ser Arg Lys Asp Asp Glu Lys Asp Ser Ser Asn Lys Asn Lys
    1205                1210                1215

Lys Lys Ser Ser Phe Ile Thr Tyr Ile Ser Thr Lys Lys Phe Lys
    1220                1225                1230

Lys Val Ser Gln Thr Ile Val Ser Val Met Ile Asn Ala Tyr Asp
    1235                1240                1245

Gly Val Ile Gln Val Val Ser Thr Ile Lys Gly Ile Ala Lys Asp
    1250                1255                1260

Ile Val Ile Phe Phe Gln Asn Ile
    1265                1270

<210> SEQ ID NO 2
<211> LENGTH: 3816
<212> TYPE: DNA
<213> ORGANISM: Plasmodium falciparum

<400> SEQUENCE: 2
atgagaaacc tttccatat taccatttgt ttagttacac ttaatttatt tattttggaa      60
ataagtgcaa aaactaatac aagtgagaat agaaataaac gaatcggggg tcctaaatta     120
aggggtaatg ttacaagtaa tataaagttc ccatcagata acaaaggtaa aattataaga     180
ggttcgaatg ataaacttaa taaaaactct gaagatgttt tagaacaaag cgaaaaatcg     240
cttgtttcag aaaatgttcc tagtggatta gatatagatg atatccctaa gaatctatt      300
tttattcaag aagatcaaga aggtcaaact cattctgaat aaatcctga acatcagaa      360
catagtaaag atttaaataa taatggttca aaaaatgaat ctagtgatat tatttcagaa     420
aataataaat caaataaagt acaaaatcat tttgaatcat tatcagattt agaattactt     480
gaaaattcct cacaagataa tttagacaaa gatacaattt caacagaacc tttccctaat     540
caaaaacata aagacttaca acaagattta atgatgaac ctttagaacc ctttcctaca      600
caaatacata aagattataa agaaaaaat ttaataaatg aagaagattc agaaccattt     660
cccagacaaa agcataaaaa ggtagacaat cataatgaag aaaaaaacgt atttcatgaa     720
aatggttctg caaatggtaa tcaaggaagt ttgaaactta atcattcga tgaacattta      780
aaagatgaaa aatagaaaaa tgaaccactt gttcatgaaa atttatccat accaaatgat     840
ccaatagaac aaatattaaa tcaacctgaa caagaaacaa atatccagga caattgtat      900
aatgaaaaac aaaatgttga agaaaaacaa aattctcaaa taccttcgtt agatttaaaa     960
gaaccaacaa atgaagatat tttaccaaat cataatccat tagaaaatat aaaacaaagt    1020
gaatcagaaa taaatcatgt acaagatcat gcgctaccaa aagagaatat aatagacaaa    1080
```

```
cttgataatc aaaaagaaca catcgatcaa tcacaacata atataaatgt attacaagaa    1140
aataacataa acaatcacca attagaacct caagagaaac ctaatattga atcgtttgaa    1200
cctaaaaata tagattcaga aattattctt cctgaaaatg ttgaaacaga agaaataata    1260
gatgatgtgc cttcccctaa acattctaac catgaaacat ttgaagaaga aacaagtgaa    1320
tctgaacatg aagaagccgt atctgaaaaa aatgcccacg aaactgtcga acatgaagaa    1380
actgtgtctc aagaaagcaa tcctgaaaaa gctgataatg atggaaatgt atctcaaaac    1440
agcaacaacg aattaaatga aaatgaattc gttgaatcgg aaaaaagcga gcatgaagca    1500
gctgaaaatg aagaaagtag tcttgaagaa ggccatcatg aagaaattgt acctgaacaa    1560
aataatgaag aatcaggtga aagtaaatta gttgataatg atgaaggtgg ttttgaagaa    1620
gctcatcatg aaaattttc atctgaagta agtaactctg aattaaatga aaatgaattt    1680
gttgaatctg acaaaagtgt aactgaacct gctgaacatg aagaagttgt atctgaagaa    1740
agcaaccctg aaccagctga aaatgaagaa agtagtatag aagaagctca tcaggaagaa    1800
attgtacctg aacaaaatga tgaagaatca ggtgaaagtg gattagttga taatgaagaa    1860
ggtgattttg aagaacctaa tcatgaagaa tttgaacctg atcaaaatga ctctgaatta    1920
agtgaaaatg aattagttga atcagaaaaa agtgtatctg aaccagctga acatgtagaa    1980
attgtatcag aaaaagtgt atctgaacca gctgaacacg tagaaattgt atctgaaaaa    2040
agtacatccg aaccagctga acatgtagaa agtgtatctg aacaaagtaa taacgaacca    2100
tccgaaaaga aagatggacc agttccttca aaaccatttg aagaaattga aaaagtggat    2160
gttcaaccta aaattgtaga ccttcaaata attgaaccta attttgttga ctcacaacca    2220
aatccacaag aaccagttga accatcattt gtcaaaattg aaaaagttcc ttctgaagaa    2280
aataaacatg caagtgttga tcctgaagta aaagaaaaag aaaatgtatc tgaagttgtt    2340
gaagaaaaac aaaattcaca agaatcagtt gaagaaattc cagtaaatga ggatgaattt    2400
gaagatgttc acactgaaca attagattta gatcataaaa cagttgatcc agaaatagta    2460
gaagttgaag aaattccttc agaactacat gaaaatgaag tggctcatcc agaaattgtt    2520
gaaattgagg aagttttttcc tgaaccaaat caaaataacg aatttcaaga aattaatgaa    2580
gatgataaaa gtgcacatat tcagcatgaa atagtagaag tagaagaaat acttccagaa    2640
gatgataaaa atgaaaaagt tgaacatgaa atagtagaag ttgaagaaat tctaccagaa    2700
gataaaaatg aaaaaggtca acatgaaata gtagaggttg aagaaattct accagaagat    2760
gataaaaatg aaaaagttga acatgaaata gtagaagttg aagaaattct accagaagat    2820
aaaaatgaaa aggtcaaca tgaaatagta gaggttgaag aaattctacc agaagataaa    2880
aatgaaaaag ttgaacatga atagtagaa gttgaagaaa ttctaccaga agataaaaat    2940
gaaaaaggtc aacatgaaat agtagaggtt gaagaaattc taccagaaga taaaaatgaa    3000
aaagttcaac atgaaatagt agaagttgaa gaaattctac cagaagataa aaatgaaaaa    3060
ggtcaacatg aaatagtaga ggttgaagaa attctaccag aagaagataa aaatgaaaaa    3120
ggtcaacatg aaatagtaga ggttgaagaa attctaccag aagataaaaa tgaaaaagtt    3180
caacatgaaa tagtagaggt tgaagaaatt ctaccagaag ataaaaatga aaaagttcaa    3240
catgaaatag tagaggttga agaaattctt ccagaaattg ttgaaattga agaagtacca    3300
tcacaaacaa ataacaatga aaatattgaa actataaaac cagaagaaaa aaagaatgaa    3360
tttagtgttg aagaaaaagc aattccacaa gaacccgtgg tacctacatt aaatgaaaat    3420
```

-continued

```
gaaaacgtta ctcccaaacc atctgaaggt gaatccacta aaccagatat agttcaaatt    3480
aaaatagtac aagaaaataa accaaataaa aaggaaacac cagtagtaga tggtccaaaa    3540
catgtagaac aaaatataca agaagatgat aatgatgaag aggatgatga tgatatagat    3600
tttgaaggat tatcaagaaa agatgatgaa aaggattcat caaataaaaa taaaaagaaa    3660
tcatctttta taacatatat atctacaaag aaatttaaaa aagtatctca aactattgta    3720
agtgttatga ttaatgcata tgatggtgtt attcaagttg taagtacaat taaaggaata    3780
gcaaaggata tagtaatatt tttccaaaac atttaa                              3816
```

<210> SEQ ID NO 3
<211> LENGTH: 448
<212> TYPE: PRT
<213> ORGANISM: Plasmodium falciparum

<400> SEQUENCE: 3

```
Met Met Leu Tyr Ile Ser Ala Lys Lys Ala Gln Val Ala Phe Ile Leu
1               5                   10                  15

Tyr Ile Val Leu Val Leu Arg Ile Ile Ser Gly Asn Asn Asp Phe Cys
            20                  25                  30

Lys Pro Ser Ser Leu Asn Ser Glu Ile Ser Gly Phe Ile Gly Tyr Lys
        35                  40                  45

Cys Asn Phe Ser Asn Glu Gly Val His Asn Leu Lys Pro Asp Met Arg
    50                  55                  60

Glu Arg Arg Ser Ile Phe Cys Thr Ile His Ser Tyr Phe Ile Tyr Asp
65                  70                  75                  80

Lys Ile Arg Leu Ile Ile Pro Lys Lys Ser Ser Pro Glu Phe Lys
                85                  90                  95

Ile Leu Pro Glu Lys Cys Phe Gln Lys Val Tyr Thr Asp Tyr Glu Asn
            100                 105                 110

Arg Val Glu Thr Asp Ile Ser Glu Leu Gly Leu Ile Glu Tyr Glu Ile
        115                 120                 125

Glu Glu Asn Asp Thr Asn Pro Asn Tyr Asn Glu Arg Thr Ile Thr Ile
    130                 135                 140

Ser Pro Phe Ser Pro Lys Asp Ile Glu Phe Phe Cys Phe Cys Asp Asn
145                 150                 155                 160

Thr Glu Lys Val Ile Ser Ser Ile Glu Gly Arg Ser Ala Met Val His
                165                 170                 175

Val Arg Val Leu Lys Tyr Pro His Asn Ile Leu Phe Thr Asn Leu Thr
            180                 185                 190

Asn Asp Leu Phe Thr Tyr Leu Pro Lys Thr Tyr Asn Glu Ser Asn Phe
        195                 200                 205

Val Ser Asn Val Leu Glu Val Glu Leu Asn Asp Gly Glu Leu Phe Val
    210                 215                 220

Leu Ala Cys Glu Leu Ile Asn Lys Lys Cys Phe Gln Glu Gly Lys Glu
225                 230                 235                 240

Lys Ala Leu Tyr Lys Ser Asn Lys Ile Tyr His Lys Asn Leu Thr
                245                 250                 255

Ile Phe Lys Ala Pro Phe Tyr Val Thr Ser Lys Asp Val Asn Thr Glu
            260                 265                 270

Cys Thr Cys Lys Phe Lys Asn Asn Tyr Lys Ile Val Leu Lys Pro
        275                 280                 285

Lys Tyr Glu Lys Lys Val Ile His Gly Cys Asn Phe Ser Ser Asn Val
    290                 295                 300
```

```
Ser Ser Lys His Thr Phe Thr Asp Ser Leu Asp Ile Ser Leu Val Asp
305                 310                 315                 320

Asp Ser Ala His Ile Ser Cys Asn Val His Leu Ser Glu Pro Lys Tyr
                325                 330                 335

Asn His Leu Val Gly Leu Asn Cys Pro Gly Asp Ile Ile Pro Asp Cys
            340                 345                 350

Phe Phe Gln Val Tyr Gln Pro Glu Ser Glu Leu Glu Pro Ser Asn
        355                 360                 365

Ile Val Tyr Leu Asp Ser Gln Ile Asn Ile Gly Asp Ile Glu Tyr Tyr
    370                 375                 380

Glu Asp Ala Glu Gly Asp Asp Lys Ile Lys Leu Phe Gly Ile Val Gly
385                 390                 395                 400

Ser Ile Pro Lys Thr Thr Ser Phe Thr Cys Ile Cys Lys Lys Asp Lys
                405                 410                 415

Lys Ser Ala Tyr Met Thr Val Thr Ile Asp Ser Ala Tyr Tyr Gly Phe
                420                 425                 430

Leu Ala Lys Thr Phe Ile Phe Leu Ile Val Ala Ile Leu Leu Tyr Ile
            435                 440                 445
```

<210> SEQ ID NO 4
<211> LENGTH: 1347
<212> TYPE: DNA
<213> ORGANISM: Plasmodium falciparum

<400> SEQUENCE: 4

| | | | | | |
|---|---|---|---|---|---|
| atgatgttat | atatttctgc | gaaaaaggct | caagttgctt | ttatcttata | tatagtatta | 60 |
| gtattaagaa | taataagtgg | aaacaatgat | ttttgtaagc | ctagctcttt | gaatagtgaa | 120 |
| atatctggat | tcataggata | taagtgtaat | ttttcaaatg | aaggtgttca | taatttaaag | 180 |
| ccagatatgc | gtgaacgtag | gtctattttt | tgcaccatcc | attcgtattt | tatatatgat | 240 |
| aagataagat | aataataacc | taaaaaaagt | tcgtctcctg | agtttaaaat | attaccagaa | 300 |
| aaatgttttc | aaaaagtata | tactgattat | gagaatagag | ttgaaactga | tatatcggaa | 360 |
| ttaggtttaa | ttgaatatga | aatagaagaa | aatgatacaa | accctaatta | aatgaaaagg | 420 |
| acaataacta | tatctccatt | tagtccaaaa | gacattgaat | tttttgttt | ttgtgataat | 480 |
| actgaaaagg | ttatatcaag | tatagaaggg | agaagtgcta | tggtacatgt | acgtgtatta | 540 |
| aaatatccac | ataatatttt | atttactaat | ttaacaaatg | atcttttttac | atatttgccg | 600 |
| aaaacatata | tgaatctaa | ttttgtaagt | aatgtattag | aagtagaatt | gaatgatgga | 660 |
| gaattatttg | ttttagcttg | tgaactaatt | aataaaaaat | gttttcaaga | aggaaaagaa | 720 |
| aaagccttat | ataaaagtaa | taaaataatt | tatcataaaa | acttaactat | ctttaaagct | 780 |
| ccattttatg | ttcatcaaa | agatgttaat | acagaatgta | catgcaaatt | taaaaataat | 840 |
| aattataaaa | tagttttaaa | accaaaatat | gaaaaaaaag | tcatacacgg | atgtaacttc | 900 |
| tcttcaaatg | ttagttctaa | acatactttt | acagatagtt | tagatatttc | tttagttgat | 960 |
| gatagtgcac | atatttcatg | taacgtacat | ttgtctgaac | caaaatataa | tcatttggta | 1020 |
| ggtttaaatt | gtcctggtga | tattatacca | gattgctttt | ttcaagtata | tcaacctgaa | 1080 |
| tcagaagaac | ttgaaccatc | caacattgtt | tatttagatt | cacaaataaa | tataggagat | 1140 |
| attgaatatt | atgaagatgc | tgaaggagat | gataaaatta | aattatttgg | tatagttgga | 1200 |
| agtataccaa | aaacgacatc | ttttacttgt | atatgtaaga | aggataaaaa | aagtgcttat | 1260 |
| atgacagtta | ctatagattc | agcatattat | ggattttttgg | ctaaaacatt | tatattccta | 1320 | attgtagcaa tattattata tatttag                                                          1347

<210> SEQ ID NO 5
<211> LENGTH: 754
<212> TYPE: PRT
<213> ORGANISM: Plasmodium falciparum

<400> SEQUENCE: 5

| | | | | | | | | | | | | | | |
|---|---|---|---|---|---|---|---|---|---|---|---|---|---|---|
| Ala | Glu | Arg | Ser | Thr | Ser | Glu | Asn | Arg | Asn | Lys | Arg | Ile | Gly | Gly | Pro |
| 1 | | | | 5 | | | | | 10 | | | | | 15 | |
| Lys | Leu | Arg | Gly | Asn | Val | Thr | Ser | Asn | Ile | Lys | Phe | Pro | Ser | Asp | Asn |
| | | | 20 | | | | | 25 | | | | | 30 | | |
| Lys | Gly | Lys | Ile | Ile | Arg | Gly | Ser | Asn | Asp | Lys | Leu | Asn | Lys | Asn | Ser |
| | | 35 | | | | | 40 | | | | | 45 | | | |
| Glu | Asp | Val | Leu | Glu | Gln | Ser | Glu | Lys | Ser | Leu | Val | Ser | Glu | Asn | Val |
| | 50 | | | | | 55 | | | | | 60 | | | | |
| Pro | Ser | Gly | Leu | Asp | Ile | Asp | Ile | Pro | Lys | Glu | Ser | Ile | Phe | Ile |
| 65 | | | | 70 | | | | 75 | | | | | 80 | |
| Gln | Glu | Asp | Gln | Glu | Gly | Gln | Thr | His | Ser | Glu | Leu | Asn | Pro | Glu | Thr |
| | | | | 85 | | | | | 90 | | | | | 95 | |
| Ser | Glu | His | Ser | Lys | Asp | Leu | Asn | Asn | Asn | Gly | Ser | Lys | Asn | Glu | Ser |
| | | | 100 | | | | | 105 | | | | | 110 | | |
| Ser | Asp | Ile | Ile | Ser | Glu | Asn | Asn | Lys | Ser | Asn | Lys | Val | Gln | Asn | His |
| | | 115 | | | | | 120 | | | | | 125 | | | |
| Phe | Glu | Ser | Leu | Ser | Asp | Leu | Glu | Leu | Leu | Glu | Asn | Ser | Ser | Gln | Asp |
| | 130 | | | | | 135 | | | | | 140 | | | | |
| Asn | Leu | Asp | Lys | Asp | Thr | Ile | Ser | Thr | Glu | Pro | Phe | Pro | Asn | Gln | Lys |
| 145 | | | | | 150 | | | | | 155 | | | | | 160 |
| His | Lys | Asp | Leu | Gln | Gln | Asp | Leu | Asn | Asp | Glu | Pro | Leu | Glu | Pro | Phe |
| | | | | 165 | | | | | 170 | | | | | 175 | |
| Pro | Thr | Gln | Ile | His | Lys | Asp | Tyr | Lys | Glu | Lys | Asn | Leu | Ile | Asn | Glu |
| | | | 180 | | | | | 185 | | | | | 190 | | |
| Glu | Asp | Ser | Glu | Pro | Phe | Pro | Arg | Gln | Lys | His | Lys | Lys | Val | Asp | Asn |
| | | 195 | | | | | 200 | | | | | 205 | | | |
| His | Asn | Glu | Glu | Lys | Asn | Val | Phe | His | Glu | Asn | Gly | Ser | Ala | Asn | Gly |
| | 210 | | | | | 215 | | | | | 220 | | | | |
| Asn | Gln | Gly | Ser | Leu | Lys | Leu | Lys | Ser | Phe | Asp | Glu | His | Leu | Lys | Asp |
| 225 | | | | | 230 | | | | | 235 | | | | | 240 |
| Glu | Lys | Ile | Glu | Asn | Glu | Pro | Leu | Val | His | Glu | Asn | Leu | Ser | Ile | Pro |
| | | | | 245 | | | | | 250 | | | | | 255 | |
| Asn | Asp | Pro | Ile | Glu | Gln | Ile | Leu | Asn | Gln | Pro | Glu | Gln | Glu | Thr | Asn |
| | | | 260 | | | | | 265 | | | | | 270 | | |
| Ile | Gln | Glu | Gln | Leu | Tyr | Asn | Glu | Lys | Gln | Asn | Val | Glu | Glu | Lys | Gln |
| | | 275 | | | | | 280 | | | | | 285 | | | |
| Asn | Ser | Gln | Ile | Pro | Ser | Leu | Asp | Leu | Lys | Glu | Pro | Thr | Asn | Glu | Asp |
| | 290 | | | | | 295 | | | | | 300 | | | | |
| Ile | Leu | Pro | Asn | His | Asn | Pro | Leu | Glu | Asn | Ile | Lys | Gln | Ser | Glu | Ser |
| 305 | | | | | 310 | | | | | 315 | | | | | 320 |
| Glu | Ile | Asn | His | Val | Gln | Asp | His | Ala | Leu | Pro | Lys | Glu | Asn | Ile | Ile |
| | | | | 325 | | | | | 330 | | | | | 335 | |
| Asp | Lys | Leu | Asp | Asn | Gln | Lys | Glu | His | Ile | Asp | Gln | Ser | Gln | His | Asn |
| | | | 340 | | | | | 345 | | | | | 350 | | |
| Ile | Asn | Val | Leu | Gln | Glu | Asn | Asn | Ile | Asn | Asn | His | Gln | Leu | Glu | Pro |
| | | 355 | | | | | 360 | | | | | 365 | | | |

```
Gln Glu Lys Pro Asn Ile Glu Ser Phe Glu Pro Lys Asn Ile Asp Ser
    370                 375                 380

Glu Ile Ile Leu Pro Glu Asn Val Glu Thr Glu Ile Ile Asp Asp
385                 390                 395                 400

Val Pro Ser Pro Lys His Ser Asn His Glu Thr Phe Glu Glu Thr
                405                 410                 415

Ser Glu Ser Glu His Glu Glu Ala Val Ser Glu Lys Asn Ala His Glu
            420                 425                 430

Thr Val Glu His Glu Glu Thr Val Ser Gln Glu Ser Asn Pro Glu Lys
        435                 440                 445

Ala Asp Asn Asp Gly Asn Val Ser Gln Asn Ser Asn Asn Glu Leu Asn
450                 455                 460

Glu Asn Glu Phe Val Glu Ser Glu Lys Ser Glu His Glu Ala Asp Asn
465                 470                 475                 480

Thr Glu Lys Val Ile Ser Ser Ile Glu Gly Arg Ser Ala Met Val His
                485                 490                 495

Val Arg Val Leu Lys Tyr Pro His Asn Ile Leu Phe Thr Asn Leu Thr
            500                 505                 510

Asn Asp Leu Phe Thr Tyr Leu Pro Lys Thr Tyr Asn Glu Ser Asn Phe
        515                 520                 525

Val Ser Asn Val Leu Glu Val Glu Leu Asn Asp Gly Glu Leu Phe Val
530                 535                 540

Leu Ala Cys Glu Leu Ile Asn Lys Lys Cys Phe Gln Glu Gly Lys Glu
545                 550                 555                 560

Lys Ala Leu Tyr Lys Ser Asn Lys Ile Ile Tyr His Lys Asn Leu Thr
                565                 570                 575

Ile Phe Lys Ala Pro Phe Tyr Val Thr Ser Lys Asp Val Asn Thr Glu
            580                 585                 590

Cys Thr Cys Lys Phe Lys Asn Asn Tyr Lys Ile Val Leu Lys Pro
        595                 600                 605

Lys Tyr Glu Lys Lys Val Ile His Gly Cys Asn Phe Ser Ser Asn Val
610                 615                 620

Ser Ser Lys His Thr Phe Thr Asp Ser Leu Asp Ile Ser Leu Val Asp
625                 630                 635                 640

Asp Ser Ala His Ile Ser Cys Asn Val His Leu Ser Glu Pro Lys Tyr
                645                 650                 655

Asn His Leu Val Gly Leu Asn Cys Pro Gly Asp Ile Pro Asp Cys
            660                 665                 670

Phe Phe Gln Val Tyr Gln Pro Glu Ser Glu Glu Leu Glu Pro Ser Asn
        675                 680                 685

Ile Val Tyr Leu Asp Ser Gln Ile Asn Ile Gly Asp Ile Glu Tyr Tyr
690                 695                 700

Glu Asp Ala Glu Gly Asp Asp Lys Ile Lys Leu Phe Gly Ile Val Gly
705                 710                 715                 720

Ser Ile Pro Lys Thr Thr Ser Phe Thr Cys Ile Cys Lys Lys Asp Lys
                725                 730                 735

Lys Ser Ala Tyr Met Thr Val Thr Ile Asp Ser Ala His His His
            740                 745                 750

His His

<210> SEQ ID NO 6
<211> LENGTH: 2361
<212> TYPE: DNA
<213> ORGANISM: Plasmodium falciparum
```

<400> SEQUENCE: 6

```
atgaaattta taaaaaaag agttgcaata gccacgttta ttgctttgat atttgtaagt    60
ttttttacaa tatcatcaat ccaagatgct caagcagccg aaagatctac aagtgagaat   120
agaaataaac gaatcggggg tcctaaatta aggggtaatg ttacaagtaa tataaagttc   180
ccatcagata acaaaggtaa aattataaga ggttcgaatg ataaacttaa taaaaactct   240
gaagatgttt tagaacaaag cgaaaaatcg cttgtttcag aaaatgttcc tagtggatta   300
gatatagatg atatccctaa agaatctatt tttattcaag aagatcaaga aggtcaaact   360
cattctgaat taaatcctga aacatcagaa catagtaaag atttaaataa taatggttca   420
aaaaatgaat ctagtgatat tatttcagaa aataataaat caaataaagt acaaaatcat   480
tttgaatcat tatcagattt agaattactt gaaaattcct cacaagataa tttagacaaa   540
gatacaattt caacagaacc ttttcctaat caaaaacata aagacttaca acaagattta   600
aatgatgaac cttagaacc ctttcctaca caaatacata aagattataa agaaaaaaat   660
ttaataaatg aagaagattc agaaccattt cccagacaaa agcataaaaa ggtagacaat   720
cataatgaag aaaaaaacgt atttcatgaa aatggttctg caaatggtaa tcaaggaagt   780
ttgaaactta aatcattcga tgaacattta aaagatgaaa aatagaaaa tgaaccactt   840
gttcatgaaa atttatccat accaaatgat ccaatagaac aaatattaaa tcaacctgaa   900
caagaaacaa atatccagga acaattgtat aatgaaaaac aaaatgttga agaaaaacaa   960
aattctcaaa taccttcgtt agatttaaaa gaaccaacaa atgaagatat tttaccaaat  1020
cataatccat tagaaaatat aaaacaaagt gaatcagaaa taaatcatgt acaagatcat  1080
gcgctaccaa aagagaatat aatagacaaa cttgataatc aaaaagaaca catcgatcaa  1140
tcacaacata atataaatgt attacaagaa aataacataa acaatcacca attagaacct  1200
caagagaaac ctaatattga atcgtttgaa cctaaaaata tagattcaga aattattctt  1260
cctgaaaatg ttgaaacaga agaaataata gatgatgtgc cttcccctaa acattctaac  1320
catgaaacat ttgaagaaga aacaagtgaa tctgaacatg aagaagccgt atctgaaaaa  1380
aatgcccacg aaactgtcga acatgaagaa actgtgtctc aagaaagcaa tcctgaaaaa  1440
gctgataatg atggaaatgt atctcaaaac agcaacaacg aattaaatga aaatgaattc  1500
gttgaatcgg aaaaaagcga gcatgaagca gataatactg aaaaggttat atcaagtata  1560
gaagggagaa gtgctatggt acatgtacgt gtattaaaat atccacataa tattttattt  1620
actaatttaa caaatgatct ttttacatat ttgccgaaaa catataatga atctaatttt  1680
gtaagtaatg tattagaagt agaattgaat gatggagaat tatttgtttt agcttgtgaa  1740
ctaattaata aaaatgttt tcaagaagga aagaaaaag ccttatataa aagtaataaa  1800
ataatttatc ataaaaactt aactatcttt aaagctccat tttatgttac atcaaaagat  1860
gttaatacag aatgtacatg caaatttaaa aataataatt ataaaatagt tttaaaacca  1920
aaatatgaaa aaaagtcat acacggatgt aacttctctt caaatgttag ttctaaacat  1980
acttttacag atagtttaga tatttcttta gttgatgata gtgcacatat ttcatgtaac  2040
gtacattgt ctgaaccaaa atataatcat ttggtaggtt taaattgtcc tggtgatatt  2100
ataccagatt gcttttttca agtatatcaa cctgaatcag aagaacttga accatccaac  2160
attgtttatt tagattcaca aataaatata ggagatattg aatattatga agatgctgaa  2220
ggagatgata aaattaaatt atttggtata gttggaagta taccaaaaac gacatctttt  2280
```

```
acttgtatat gtaagaagga taaaaaagt gcttatatga cagttactat agattcagca    2340
catcaccatc atcaccatta g                                              2361
```

<210> SEQ ID NO 7
<211> LENGTH: 875
<212> TYPE: PRT
<213> ORGANISM: Plasmodium falciparum

<400> SEQUENCE: 7

```
Ala Glu Arg Ser Thr Ser Glu Asn Arg Asn Lys Arg Ile Gly Gly Pro
1               5                   10                  15

Lys Leu Arg Gly Asn Val Thr Ser Asn Ile Lys Phe Pro Ser Asp Asn
            20                  25                  30

Lys Gly Lys Ile Ile Arg Gly Ser Asn Asp Lys Leu Asn Lys Asn Ser
        35                  40                  45

Glu Asp Val Leu Glu Gln Ser Glu Lys Ser Leu Val Ser Glu Asn Val
    50                  55                  60

Pro Ser Gly Leu Asp Ile Asp Ile Pro Lys Glu Ser Ile Phe Ile
65                  70                  75                  80

Gln Glu Asp Gln Glu Gly Gln Thr His Ser Glu Leu Asn Pro Glu Thr
                85                  90                  95

Ser Glu His Ser Lys Asp Leu Asn Asn Asn Gly Ser Lys Asn Glu Ser
            100                 105                 110

Ser Asp Ile Ile Ser Glu Asn Asn Lys Ser Asn Lys Val Gln Asn His
        115                 120                 125

Phe Glu Ser Leu Ser Asp Leu Glu Leu Leu Glu Asn Ser Ser Gln Asp
    130                 135                 140

Asn Leu Asp Lys Asp Thr Ile Ser Thr Glu Pro Phe Pro Asn Gln Lys
145                 150                 155                 160

His Lys Asp Leu Gln Gln Asp Leu Asn Asp Glu Pro Leu Glu Pro Phe
                165                 170                 175

Pro Thr Gln Ile His Lys Asp Tyr Lys Glu Lys Asn Leu Ile Asn Glu
            180                 185                 190

Glu Asp Ser Glu Pro Phe Pro Arg Gln Lys His Lys Lys Val Asp Asn
        195                 200                 205

His Asn Glu Glu Lys Asn Val Phe His Glu Asn Gly Ser Ala Asn Gly
    210                 215                 220

Asn Gln Gly Ser Leu Lys Leu Lys Ser Phe Asp Glu His Leu Lys Asp
225                 230                 235                 240

Glu Lys Ile Glu Asn Glu Pro Leu Val His Glu Asn Leu Ser Ile Pro
                245                 250                 255

Asn Asp Pro Ile Glu Gln Ile Leu Asn Gln Pro Glu Gln Glu Thr Asn
            260                 265                 270

Ile Gln Glu Gln Leu Tyr Asn Glu Lys Gln Asn Val Glu Glu Lys Gln
        275                 280                 285

Asn Ser Gln Ile Pro Ser Leu Asp Leu Lys Glu Pro Thr Asn Glu Asp
    290                 295                 300

Ile Leu Pro Asn His Asn Pro Leu Glu Asn Ile Lys Gln Ser Glu Ser
305                 310                 315                 320

Glu Ile Asn His Val Gln Asp His Ala Leu Pro Lys Glu Asn Ile Ile
                325                 330                 335

Asp Lys Leu Asp Asn Gln Lys Glu His Ile Asp Gln Ser Gln His Asn
            340                 345                 350

Ile Asn Val Leu Gln Glu Asn Asn Ile Asn Asn His Gln Leu Glu Pro
```

```
                    355                 360                 365
Gln Glu Lys Pro Asn Ile Glu Ser Phe Glu Pro Lys Asn Ile Asp Ser
370                 375                 380
Glu Ile Ile Leu Pro Glu Asn Val Glu Thr Glu Ile Ile Asp Asp
385                 390                 395                 400
Val Pro Ser Pro Lys His Ser Asn His Glu Thr Phe Glu Glu Thr
                405                 410                 415
Ser Glu Ser Glu His Glu Glu Ala Val Ser Glu Lys Asn Ala His Glu
                420                 425                 430
Thr Val Glu His Glu Glu Thr Val Ser Gln Glu Ser Asn Pro Glu Lys
            435                 440                 445
Ala Asp Asn Asp Gly Asn Val Ser Gln Asn Ser Asn Glu Leu Asn
450                 455                 460
Glu Asn Glu Phe Val Glu Ser Glu Lys Ser His Glu Ala Gly Asn
465                 470                 475                 480
Asn Asp Phe Cys Lys Pro Ser Ser Leu Asn Ser Glu Ile Ser Gly Phe
                485                 490                 495
Ile Gly Tyr Lys Cys Asn Phe Ser Asn Glu Gly Val His Asn Leu Lys
            500                 505                 510
Pro Asp Met Arg Glu Arg Arg Ser Ile Phe Cys Thr Ile His Ser Tyr
            515                 520                 525
Phe Ile Tyr Asp Lys Ile Arg Leu Ile Pro Lys Lys Ser Ser Ser
530                 535                 540
Pro Glu Phe Lys Ile Leu Pro Glu Lys Cys Phe Gln Lys Val Tyr Thr
545                 550                 555                 560
Asp Tyr Glu Asn Arg Val Glu Thr Asp Ile Ser Glu Leu Gly Leu Ile
                565                 570                 575
Glu Tyr Glu Ile Glu Glu Asn Asp Thr Asn Pro Asn Tyr Asn Glu Arg
            580                 585                 590
Thr Ile Thr Ile Ser Pro Phe Ser Pro Lys Asp Ile Glu Phe Phe Cys
            595                 600                 605
Phe Cys Asp Asn Thr Glu Lys Val Ile Ser Ser Ile Glu Gly Arg Ser
        610                 615                 620
Ala Met Val His Val Arg Val Leu Lys Tyr Pro His Asn Ile Leu Phe
625                 630                 635                 640
Thr Asn Leu Thr Asn Asp Leu Phe Thr Tyr Leu Pro Lys Thr Tyr Asn
                645                 650                 655
Glu Ser Asn Phe Val Ser Asn Val Leu Glu Val Glu Leu Asn Asp Gly
                660                 665                 670
Glu Leu Phe Val Leu Ala Cys Glu Leu Ile Asn Lys Lys Cys Phe Gln
            675                 680                 685
Glu Gly Lys Glu Lys Ala Leu Tyr Lys Ser Asn Lys Ile Ile Tyr His
            690                 695                 700
Lys Asn Leu Thr Ile Phe Lys Ala Pro Phe Tyr Val Thr Ser Lys Asp
705                 710                 715                 720
Val Asn Thr Glu Cys Thr Cys Lys Phe Lys Asn Asn Tyr Lys Ile
                725                 730                 735
Val Leu Lys Pro Lys Tyr Glu Lys Lys Val Ile His Gly Cys Asn Phe
                740                 745                 750
Ser Ser Asn Val Ser Ser Lys His Thr Phe Thr Asp Ser Leu Asp Ile
            755                 760                 765
Ser Leu Val Asp Asp Ser Ala His Ile Ser Cys Asn Val His Leu Ser
        770                 775                 780
```

```
Glu Pro Lys Tyr Asn His Leu Val Gly Leu Asn Cys Pro Gly Asp Ile
785                 790                 795                 800

Ile Pro Asp Cys Phe Phe Gln Val Tyr Gln Pro Glu Ser Glu Glu Leu
            805                 810                 815

Glu Pro Ser Asn Ile Val Tyr Leu Asp Ser Gln Ile Asn Ile Gly Asp
            820                 825                 830

Ile Glu Tyr Tyr Glu Asp Ala Glu Gly Asp Asp Lys Ile Lys Leu Phe
            835                 840                 845

Gly Ile Val Gly Ser Ile Pro Lys Thr Thr Ser Phe Thr Cys Ile Cys
            850                 855                 860

Lys Lys Asp Lys Lys His His His His His His
865                 870                 875

<210> SEQ ID NO 8
<211> LENGTH: 2724
<212> TYPE: DNA
<213> ORGANISM: Plasmodium falciparum

<400> SEQUENCE: 8
```

| | | | | |
|---|---|---|---|---|
| atgaaattta | ataaaaaaag | agttgcaata | gccacgttta | ttgctttgat atttgtaagt | 60 |
| ttttttacaa | tatcatcaat | ccaagatgct | caagcagccg | aaagatctac aagtgagaat | 120 |
| agaaataaac | gaatcggggg | tcctaaatta | aggggtaatg | ttacaagtaa tataaagttc | 180 |
| ccatcagata | acaaaggtaa | aattataaga | ggttcgaatg | ataaacttaa taaaaactct | 240 |
| gaagatgttt | tagaacaaag | cgaaaaatcg | cttgtttcag | aaaatgttcc tagtggatta | 300 |
| gatatagatg | atatccctaa | agaatctatt | tttattcaag | aagatcaaga aggtcaaact | 360 |
| cattctgaat | taaatcctga | aacatcagaa | catagtaaag | atttaaataa taatggttca | 420 |
| aaaaatgaat | ctagtgatat | tatttcagaa | aataataaat | caaataaagt acaaaatcat | 480 |
| tttgaatcat | tatcagattt | agaattactt | gaaaattcct | cacaagataa tttagacaaa | 540 |
| gatacaattt | caacagaacc | ttttcctaat | caaaaacata | aagacttaca acaagattta | 600 |
| aatgatgaac | ctttagaacc | ctttcctaca | caaatacata | aagattataa agaaaaaaat | 660 |
| ttaataaatg | aagaagattc | agaaccattt | cccagacaaa | agcataaaaa ggtagacaat | 720 |
| cataatgaag | aaaaaaacgt | atttcatgaa | aatggttctg | caaatggtaa tcaaggaagt | 780 |
| ttgaaactta | atcattcga | tgaacattta | aaagatgaaa | aatagaaaa tgaaccactt | 840 |
| gttcatgaaa | atttatccat | accaaatgat | ccaatagaac | aaatattaaa tcaacctgaa | 900 |
| caagaaacaa | atatccagga | caattgtat | aatgaaaaac | aaaatgttga agaaaaacaa | 960 |
| aattctcaaa | taccttcgtt | agatttaaaa | gaaccaacaa | atgaagatat tttaccaaat | 1020 |
| cataatccat | tagaaaatat | aaaacaaagt | gaatcagaaa | taaatcatgt acaagatcat | 1080 |
| gcgctaccaa | aagagaatat | aatagacaaa | cttgataatc | aaaaagaaca catcgatcaa | 1140 |
| tcacaacata | atataaatgt | attacaagaa | ataacataa | acaatcacca attagaacct | 1200 |
| caagagaaac | ctaatattga | atcgtttgaa | cctaaaaata | tagattcaga aattattctt | 1260 |
| cctgaaaatg | ttgaaacaga | agaaataata | gatgatgtgc | cttcccctaa acattctaac | 1320 |
| catgaaacat | ttgaagaaga | aacaagtgaa | tctgaacatg | aagaagccgt atctgaaaaa | 1380 |
| aatgcccacg | aaactgtcga | acatgaagaa | actgtgtctc | aagaaagcaa tcctgaaaaa | 1440 |
| gctgataatg | atgaaatgt | atctcaaaac | agcaacaacg | aattaaatga aaatgaattc | 1500 |
| gttgaatcgg | aaaaaagcga | gcatgaagca | ggaaacaatg | attttttgtaa gcctagctct | 1560 |

```
ttgaatagtg aaatatctgg attcatagga tataagtgta attttttcaaa tgaaggtgtt    1620 cataatttaa agccagatat gcgtgaacgt aggtctattt tttgcaccat ccattcgtat    1680
tttatatatg ataagataag attaataata cctaaaaaaa gttcgtctcc tgagtttaaa    1740
atattaccag aaaaatgttt tcaaaaagta tatactgatt atgagaatag agttgaaact    1800
gatatatcgg aattaggttt aattgaatat gaaatagaag aaaatgatac aaaccctaat    1860
tataatgaaa ggacaataac tatatctcca tttagtccaa aagacattga attttttttgt    1920 ttttgtgata atactgaaaa ggttatatca agtatagaag ggagaagtgc tatggtacat    1980
gtacgtgtat taaaatatcc acataatatt ttatttacta atttaacaaa tgatctttttt   2040 acatatttgc cgaaaacata taatgaatct aatttttgtaa gtaatgtatt agaagtagaa    2100
ttgaatgatg gagaattatt tgttttagct tgtgaactaa ttaataaaaa atgttttcaa    2160
gaaggaaaag aaaaagcctt atataaaagt aataaaataa tttatcataa aaacttaact    2220
atctttaaag ctccattta tgttacatca aaagatgtta atacagaatg tacatgcaaa    2280
tttaaaaata taattataa aatagtttta aaaccaaaat atgaaaaaaa agtcatacac    2340
ggatgtaact tctcttcaaa tgttagttct aaacatactt ttacagatag tttagatatt    2400 tcttagttg atgatagtgc acatatttca tgtaacgtac atttgtctga accaaaaatat   2460 aatcatttgg taggtttaaa ttgtcctggt gatattatac cagattgctt ttttcaagta    2520
tatcaacctg aatcagaaga acttgaacca tccaacattg tttatttaga ttcacaaata    2580
aatataggag atattgaata ttatgaagat gctgaaggag atgataaaat taaattattt    2640
ggtatagttg gaagtatacc aaaaacgaca tcttttactt gtatatgtaa gaaggataaa    2700
aaacatcacc atcatcacca ttag                                          2724
```

<210> SEQ ID NO 9
<211> LENGTH: 641
<212> TYPE: PRT
<213> ORGANISM: Plasmodium falciparum

<400> SEQUENCE: 9

```
Ala Glu Arg Ser Ser Asp Ile Ile Ser Glu Asn Asn Lys Ser Asn
1               5                   10                  15

Lys Val Gln Asn His Phe Glu Ser Leu Ser Asp Leu Glu Leu Leu Glu
                20                  25                  30

Asn Ser Ser Gln Asp Asn Leu Asp Lys Asp Thr Ile Ser Thr Glu Pro
            35                  40                  45

Phe Pro Asn Gln Lys His Lys Asp Leu Gln Gln Asp Leu Asn Asp Glu
        50                  55                  60

Pro Leu Glu Pro Phe Pro Thr Gln Ile His Lys Asp Tyr Lys Glu Lys
65                  70                  75                  80

Asn Leu Ile Asn Glu Glu Asp Ser Glu Pro Phe Pro Arg Gln Lys His
                85                  90                  95

Lys Lys Val Asp Asn His Asn Glu Glu Lys Asn Val Phe His Glu Asn
            100                 105                 110

Gly Ser Ala Asn Gly Asn Gln Gly Ser Leu Lys Leu Lys Ser Phe Asp
        115                 120                 125

Glu His Leu Lys Asp Glu Lys Ile Glu Asn Glu Pro Leu Val His Glu
    130                 135                 140

Asn Leu Ser Ile Pro Asn Asp Pro Ile Glu Gln Ile Leu Asn Gln Pro
145                 150                 155                 160

Glu Gln Glu Thr Asn Ile Gln Gln Gln Leu Tyr Asn Glu Lys Gln Asn
```

-continued

```
                165                 170                 175
Val Glu Glu Lys Gln Asn Ser Gln Ile Pro Ser Leu Asp Leu Lys Glu
            180                 185                 190
Pro Thr Asn Glu Asp Ile Leu Pro Asn His Asn Pro Leu Glu Asn Ile
        195                 200                 205
Lys Gln Ser Glu Ser Glu Ile Asn His Val Gln Asp His Ala Leu Pro
    210                 215                 220
Lys Glu Asn Ile Ile Asp Lys Leu Asp Asn Gln Lys Glu His Ile Asp
225                 230                 235                 240
Gln Ser Gln His Asn Ile Asn Val Leu Gln Glu Asn Asn Ile Asn Asn
            245                 250                 255
His Gln Leu Glu Pro Gln Glu Lys Pro Asn Ile Glu Ser Phe Glu Pro
        260                 265                 270
Lys Asn Ile Asp Ser Glu Ile Ile Leu Pro Glu Asn Val Glu Thr Glu
    275                 280                 285
Glu Ile Ile Asp Asp Val Pro Ser Pro Lys His Ser Asn His Glu Thr
290                 295                 300
Phe Glu Glu Glu Thr Ser Glu Ser Glu His Glu Glu Ala Val Ser Glu
305                 310                 315                 320
Lys Asn Ala His Glu Thr Val Glu His Glu Glu Thr Val Ser Gln Glu
            325                 330                 335
Ser Asn Pro Glu Lys Ala Asp Asn Asp Gly Asn Val Ser Gln Asn Ser
        340                 345                 350
Asn Asn Glu Leu Asn Glu Asn Glu Phe Val Glu Ser Glu Lys Ser Glu
    355                 360                 365
His Glu Ala Asp Asn Thr Glu Lys Val Ile Ser Ser Ile Glu Gly Arg
370                 375                 380
Ser Ala Met Val His Val Arg Val Leu Lys Tyr Pro Asn Ile Leu
385                 390                 395                 400
Phe Thr Asn Leu Thr Asn Asp Leu Phe Thr Tyr Leu Pro Lys Thr Tyr
            405                 410                 415
Asn Glu Ser Asn Phe Val Ser Asn Val Leu Glu Val Glu Leu Asn Asp
        420                 425                 430
Gly Glu Leu Phe Val Leu Ala Cys Glu Leu Ile Asn Lys Lys Cys Phe
    435                 440                 445
Gln Glu Gly Lys Glu Lys Ala Leu Tyr Lys Ser Asn Lys Ile Ile Tyr
    450                 455                 460
His Lys Asn Leu Thr Ile Phe Lys Ala Pro Phe Tyr Val Thr Ser Lys
465                 470                 475                 480
Asp Val Asn Thr Glu Cys Thr Cys Lys Phe Lys Asn Asn Tyr Lys
            485                 490                 495
Ile Val Leu Lys Pro Lys Tyr Glu Lys Lys Val Ile His Gly Cys Asn
        500                 505                 510
Phe Ser Ser Asn Val Ser Ser Lys His Thr Phe Thr Asp Ser Leu Asp
    515                 520                 525
Ile Ser Leu Val Asp Asp Ser Ala His Ile Ser Cys Asn Val His Leu
    530                 535                 540
Ser Glu Pro Lys Tyr Asn His Leu Val Gly Leu Asn Cys Pro Gly Asp
545                 550                 555                 560
Ile Ile Pro Asp Cys Phe Phe Gln Val Tyr Gln Pro Glu Ser Glu Glu
            565                 570                 575
Leu Glu Pro Ser Asn Ile Val Tyr Leu Asp Ser Gln Ile Asn Ile Gly
        580                 585                 590
```

Asp Ile Glu Tyr Tyr Glu Asp Ala Glu Gly Asp Asp Lys Ile Lys Leu
         595                 600                 605

Phe Gly Ile Val Gly Ser Ile Pro Lys Thr Thr Ser Phe Thr Cys Ile
     610                 615                 620

Cys Lys Lys Asp Lys Lys Ser Ala Tyr Met Thr Val Thr Ile Asp Ser
625                 630                 635                 640

Ala

<210> SEQ ID NO 10
<211> LENGTH: 2289
<212> TYPE: DNA
<213> ORGANISM: Plasmodium falciparum

<400> SEQUENCE: 10

```
atgaaattta ataaaaaaag agttgcaata gccacgttta ttgctttgat atttgtaagt    60
tttttacaa tatcatcaat ccaagatgct caagcagccg aaagatctac aagtaatata   120
aagttcccat cagataacaa aggtaaaatt ataagaggtt cgaatgataa acttaataaa   180
aactctgaag atgttttaga acaaagcgaa aaatcgcttg tttcagaaaa tgttcctagt   240
ggattagata tagatgatat ccctaaagaa tctatttta ttcaagaaga tcaagaaggt   300
caaactcatt ctgaattaaa tcctgaaaca tcagaacata gtaaagattt aaataataat   360
ggttcaaaaa atgaatctag tgatattatt tcagaaaata taaatcaaa taagtacaa    420
aatcattttg aatcattatc agatttagaa ttacttgaaa attcctcaca agataattta   480
gacaaagata caatttcaac agaaccttt cctaatcaaa acataaaga cttacaacaa    540
gatttaaatg atgaaccttt agaaccctt cctacacaaa tacataaaga ttataaagaa   600
aaaaatttaa taatgaaga agattcagaa ccatttccca gacaaaagca taaaaaggta   660
gacaatcata tgaagaaaa aaacgtattt catgaaaatg gttctgcaaa tggtaatcaa   720
ggaagtttga aacttaaatc attcgatgaa catttaaaag atgaaaaaat agaaatgaa    780
ccacttgttc atgaaaattt atccatacca aatgatccaa tagaacaaat attaaatcaa   840
cctgaacaag aaacaaatat ccaggaacaa ttgtataatg aaaaacaaaa tgttgaagaa   900
aaacaaaatt ctcaaatacc ttcgttagat ttaaaagaac caacaaatga agatatttta   960
ccaaatcata atccattaga aaatataaaa caaagtgaat cagaaataaa tcatgtacaa  1020
gatcatgcgc taccaaaaga gaatataata gacaaacttg ataatcaaaa agaacacatc  1080
gatcaatcac aacataatat aaatgtatta caagaaaata acataaacaa tcaccaatta  1140
gaacctcaag agaaacctaa tattgaatcg tttgaaccta aaatataga ttcagaaatt    1200
attcttcctg aaaatgttga aacagaagaa ataatagatg atgtgccttc ccctaaacat  1260
tctaaccatg aaacatttga agaagaaaca agtgaatctg aacatgaaga agccgtatct  1320
gaaaaaaatg cccacgaaac tgtcgaacat gaagaaactg tgtctcaaga agcaatcct    1380
gaaaagctg ataatgatgg aaatgtatct caaacagca caacgaatt aaatgaaaat     1440
gaattcgttg aatcggaaaa aagcgagcat gaagcagata tactgaaaa ggttatatca    1500
agtatagaag ggagaagtgc tatggtacat gtacgtgtat aaaatatcc acataatatt   1560
ttatttacta atttaacaaa tgatcttttt acatatttgc cgaaaacata taatgaatct  1620
aattttgtaa gtaatgtatt agaagtagaa ttgaatgatg gagaattatt tgttttagct  1680
tgtgaactaa ttaataaaaa atgttttcaa gaaggaaaag aaaaagcctt atataaaagt  1740
aataaaataa tttatcataa aaacttaact atctttaaag ctccatttta tgttacatca  1800
```

```
aaagatgtta atacagaatg tacatgcaaa tttaaaaata ataattataa aatagtttta    1860
aaaccaaaat atgaaaaaaa agtcatacac ggatgtaact tctcttcaaa tgttagttct    1920
aaacatactt ttacagatag tttagatatt tctttagttg atgatagtgc acatatttca    1980
tgtaacgtac atttgtctga accaaaatat aatcatttgg taggtttaaa ttgtcctggt    2040
gatattatac cagattgctt ttttcaagta tatcaacctg aatcagaaga acttgaacca    2100
tccaacattg tttatttaga ttcacaaata aatataggag atattgaata ttatgaagat    2160
gctgaaggag atgataaaat taaattattt ggtatagttg aagtatacc aaaaacgaca     2220 tcttttactt gtatatgtaa gaaggataaa aaagtgcttt atatgacagt tactatagat    2280
tcagcatag                                                           2289
```

<210> SEQ ID NO 11
<211> LENGTH: 762
<212> TYPE: PRT
<213> ORGANISM: Plasmodium falciparum

<400> SEQUENCE: 11

```
Ala Glu Arg Ser Ser Asp Ile Ile Ser Glu Asn Asn Lys Ser Asn
1               5                   10                  15

Lys Val Gln Asn His Phe Glu Ser Leu Ser Asp Leu Glu Leu Glu
                20                  25                  30

Asn Ser Ser Gln Asp Asn Leu Asp Lys Asp Thr Ile Ser Thr Glu Pro
            35                  40                  45

Phe Pro Asn Gln Lys His Lys Asp Leu Gln Gln Asp Leu Asn Asp Glu
50                  55                  60

Pro Leu Glu Pro Phe Pro Thr Gln Ile His Lys Asp Tyr Lys Glu Lys
65                  70                  75                  80

Asn Leu Ile Asn Glu Glu Asp Ser Glu Pro Phe Pro Arg Gln Lys His
                85                  90                  95

Lys Lys Val Asp Asn His Asn Glu Glu Lys Asn Val Phe His Glu Asn
            100                 105                 110

Gly Ser Ala Asn Gly Asn Gln Gly Ser Leu Lys Leu Lys Ser Phe Asp
        115                 120                 125

Glu His Leu Lys Asp Glu Lys Ile Glu Asn Glu Pro Leu Val His Glu
    130                 135                 140

Asn Leu Ser Ile Pro Asn Asp Pro Ile Glu Gln Ile Leu Asn Gln Pro
145                 150                 155                 160

Glu Gln Glu Thr Asn Ile Gln Glu Gln Leu Tyr Asn Glu Lys Gln Asn
                165                 170                 175

Val Glu Glu Lys Gln Asn Ser Gln Ile Pro Ser Leu Asp Leu Lys Glu
            180                 185                 190

Pro Thr Asn Glu Asp Ile Leu Pro Asn His Asn Pro Leu Glu Asn Ile
        195                 200                 205

Lys Gln Ser Glu Ser Glu Ile Asn His Val Gln Asp His Ala Leu Pro
    210                 215                 220

Lys Glu Asn Ile Ile Asp Lys Leu Asp Asn Gln Lys Glu His Ile Asp
225                 230                 235                 240

Gln Ser Gln His Asn Ile Asn Val Leu Gln Glu Asn Asn Ile Asn Asn
                245                 250                 255

His Gln Leu Glu Pro Gln Glu Lys Pro Asn Ile Glu Ser Phe Glu Pro
            260                 265                 270

Lys Asn Ile Asp Ser Glu Ile Ile Leu Pro Glu Asn Val Glu Thr Glu
```

-continued

```
                275                 280                 285
Glu Ile Ile Asp Asp Val Pro Ser Pro Lys His Ser Asn His Glu Thr
290                 295                 300
Phe Glu Glu Glu Thr Ser Glu Ser Glu His Glu Glu Ala Val Ser Glu
305                 310                 315                 320
Lys Asn Ala His Glu Thr Val Glu His Glu Glu Thr Val Ser Gln Glu
                325                 330                 335
Ser Asn Pro Glu Lys Ala Asp Asn Asp Gly Asn Val Ser Gln Asn Ser
            340                 345                 350
Asn Asn Glu Leu Asn Glu Asn Glu Phe Val Glu Ser Glu Lys Ser Glu
                355                 360                 365
His Glu Ala Gly Asn Asn Asp Phe Cys Lys Pro Ser Ser Leu Asn Ser
            370                 375                 380
Glu Ile Ser Gly Phe Ile Gly Tyr Lys Cys Asn Phe Ser Asn Glu Gly
385                 390                 395                 400
Val His Asn Leu Lys Pro Asp Met Arg Glu Arg Arg Ser Ile Phe Cys
                405                 410                 415
Thr Ile His Ser Tyr Phe Ile Tyr Asp Lys Ile Arg Leu Ile Ile Pro
            420                 425                 430
Lys Lys Ser Ser Ser Pro Glu Phe Lys Ile Leu Pro Glu Lys Cys Phe
                435                 440                 445
Gln Lys Val Tyr Thr Asp Tyr Glu Asn Arg Val Glu Thr Asp Ile Ser
450                 455                 460
Glu Leu Gly Leu Ile Glu Tyr Glu Ile Glu Glu Asn Asp Thr Asn Pro
465                 470                 475                 480
Asn Tyr Asn Glu Arg Thr Ile Thr Ile Ser Pro Phe Ser Pro Lys Asp
                485                 490                 495
Ile Glu Phe Phe Cys Phe Cys Asp Asn Thr Glu Lys Val Ile Ser Ser
            500                 505                 510
Ile Glu Gly Arg Ser Ala Met Val His Val Arg Val Leu Lys Tyr Pro
                515                 520                 525
His Asn Ile Leu Phe Thr Asn Leu Thr Asn Asp Leu Phe Thr Tyr Leu
            530                 535                 540
Pro Lys Thr Tyr Asn Glu Ser Asn Phe Val Ser Asn Val Leu Glu Val
545                 550                 555                 560
Glu Leu Asn Asp Gly Glu Leu Phe Val Leu Ala Cys Glu Leu Ile Asn
                565                 570                 575
Lys Lys Cys Phe Gln Glu Gly Lys Glu Lys Ala Leu Tyr Lys Ser Asn
            580                 585                 590
Lys Ile Ile Tyr His Lys Asn Leu Thr Ile Phe Lys Ala Pro Phe Tyr
                595                 600                 605
Val Thr Ser Lys Asp Val Asn Thr Glu Cys Thr Cys Lys Phe Lys Asn
            610                 615                 620
Asn Asn Tyr Lys Ile Val Leu Lys Pro Lys Tyr Glu Lys Lys Val Ile
625                 630                 635                 640
His Gly Cys Asn Phe Ser Ser Asn Val Ser Ser Lys His Thr Phe Thr
                645                 650                 655
Asp Ser Leu Asp Ile Ser Leu Val Asp Asp Ser Ala His Ile Ser Cys
            660                 665                 670
Asn Val His Leu Ser Glu Pro Lys Tyr Asn His Leu Val Gly Leu Asn
                675                 680                 685
Cys Pro Gly Asp Ile Ile Pro Asp Cys Phe Phe Gln Val Tyr Gln Pro
            690                 695                 700
```

```
Glu Ser Glu Glu Leu Glu Pro Ser Asn Ile Val Tyr Leu Asp Ser Gln
705                 710                 715                 720

Ile Asn Ile Gly Asp Ile Glu Tyr Tyr Glu Asp Ala Glu Gly Asp Asp
            725                 730                 735

Lys Ile Lys Leu Phe Gly Ile Val Gly Ser Ile Pro Thr Thr Ser
        740                 745                 750

Phe Thr Cys Ile Cys Lys Lys Asp Lys Lys
        755                 760

<210> SEQ ID NO 12
<211> LENGTH: 2652
<212> TYPE: DNA
<213> ORGANISM: Plasmodium falciparum

<400> SEQUENCE: 12
```

| | | | | | |
|---|---|---|---|---|---|
| atgaaattta | ataaaaaaag | agttgcaata | gccacgttta | ttgctttgat | atttgtaagt | 60 |
| ttttttacaa | tatcatcaat | ccaagatgct | caagcagccg | aaagatctac | aagtaatata | 120 |
| aagttcccat | cagataacaa | aggtaaaatt | ataagaggtt | cgaatgataa | acttaataaa | 180 |
| aactctgaag | atgttttaga | acaaagcgaa | aaatcgcttg | tttcagaaaa | tgttcctagt | 240 |
| ggattagata | tagatgatat | ccctaaagaa | tctattttta | ttcaagaaga | tcaagaaggt | 300 |
| caaactcatt | ctgaattaaa | tcctgaaaca | tcagaacata | gtaaagattt | aaataataat | 360 |
| ggttcaaaaa | atgaatctag | tgatattatt | tcagaaaata | taaatcaaa | taagtacaa | 420 |
| aatcattttg | aatcattatc | agatttagaa | ttacttgaaa | attcctcaca | agataattta | 480 |
| gacaaagata | caatttcaac | agaacctttt | cctaatcaaa | acataaaga | cttacaacaa | 540 |
| gatttaaatg | atgaaccttt | agaaccctttt | cctacacaaa | tacataaaga | ttataaagaa | 600 |
| aaaaatttaa | taatgaaga | agattcagaa | ccatttccca | gacaaaagca | taaaaaggta | 660 |
| gacaatcata | tgaagaaaa | aaacgtattt | catgaaaatg | gttctgcaaa | tggtaatcaa | 720 |
| ggaagtttga | aacttaaatc | attcgatgaa | catttaaaag | atgaaaaaat | agaaaatgaa | 780 |
| ccacttgttc | atgaaaattt | atccatacca | aatgatccaa | tagaacaaat | attaaatcaa | 840 |
| cctgaacaag | aaacaaatat | ccaggaacaa | ttgtataatg | aaaaacaaaa | tgttgaagaa | 900 |
| aaacaaaatt | ctcaaatacc | ttcgttagat | ttaaaagaac | caacaaatga | agatattta | 960 |
| ccaaatcata | atccattaga | aaatataaaa | caagtgaat | cagaaataaa | tcatgtacaa | 1020 |
| gatcatgcgc | taccaaaaga | gaatataata | gacaaacttg | ataatcaaaa | agaacacatc | 1080 |
| gatcaatcac | aacataatat | aaatgtatta | caagaaaata | acataaacaa | tcaccaatta | 1140 |
| gaacctcaag | agaaacctaa | tattgaatcg | tttgaaccta | aaatatagaa | ttcagaaatt | 1200 |
| attcttcctg | aaaatgttga | aacagaagaa | ataatagatg | atgtgccttc | ccctaaacat | 1260 |
| tctaaccatg | aaacatttga | agaagaaaca | agtgaatctg | aacatgaaga | agccgtatct | 1320 |
| gaaaaaaatg | cccacgaaac | tgtcgaacat | gaagaaactg | tgtctcaaga | aagcaatcct | 1380 |
| gaaaaagctg | ataatgatgg | aaatgtatct | caaaacagca | caacgaatt | aaatgaaaat | 1440 |
| gaattcgttg | aatcggaaaa | aagcgagcat | gaagcaggaa | acaatgattt | ttgtaagcct | 1500 |
| agctctttga | atagtgaaat | atctggattc | ataggatata | agtgtaattt | ttcaaatgaa | 1560 |
| ggtgttcata | atttaaagcc | agatatgcgt | gaacgtaggt | ctattttttg | caccatccat | 1620 |
| tcgtatttta | tatatgataa | gataagatta | ataaaccta | aaaaaagttc | gtctcctgag | 1680 |
| tttaaaatat | taccagaaaa | atgttttcaa | aaagtatata | ctgattatga | aatagagtt | 1740 |

```
gaaactgata tatcggaatt aggtttaatt gaatatgaaa tagaagaaaa tgatacaaac    1800
cctaattata atgaaaggac aataactata tctccattta gtccaaaaga cattgaattt    1860
ttttgttttt gtgataatac tgaaaaggtt atatcaagta tagaagggag aagtgctatg    1920
gtacatgtac gtgtattaaa atatccacat aatattttat ttactaattt aacaaatgat    1980 cttttacat atttgccgaa acatataat gaatctaatt ttgtaagtaa tgtattagaa      2040
gtagaattga atgatggaga attatttgtt ttagcttgtg aactaattaa taaaaaatgt    2100
tttcaagaag gaaaagaaaa agccttatat aaaagtaata aataatttta tcataaaaac    2160
ttaactatct ttaaagctcc attttatgtt acatcaaaag atgttaatac agaatgtaca    2220
tgcaaattta aaaataataa ttataaaata gttttaaaac caaatatga aaaaaaagtc    2280 atacacggat gtaacttctc ttcaaatgtt agttctaaac atactttac agatagttta    2340 gatatttctt tagttgatga tagtgcacat atttcatgta acgtacattt gtctgaacca    2400
aaatataatc atttggtagg tttaaattgt cctggtgata ttataccaga ttgctttttt    2460
caagtatatc aacctgaatc agaagaactt gaaccatcca acattgttta tttagattca    2520
caaataaata taggagatat tgaatattat gaagatgctg aaggagatga taaaattaaa    2580
ttatttggta tagttggaag tataccaaaa acgacatctt ttacttgtat atgtaagaag    2640 gataaaaat ag                                                        2652
```

<210> SEQ ID NO 13
<211> LENGTH: 1502
<212> TYPE: PRT
<213> ORGANISM: Plasmodium falciparum

<400> SEQUENCE: 13

```
Met Lys Cys Asn Ile Ser Ile Tyr Phe Phe Ala Ser Phe Phe Val Leu
1               5                   10                  15

Tyr Phe Ala Lys Ala Arg Asn Glu Tyr Asp Ile Lys Glu Asn Glu Lys
            20                  25                  30

Phe Leu Asp Val Tyr Lys Glu Lys Phe Asn Glu Leu Asp Lys Lys Lys
        35                  40                  45

Tyr Gly Asn Val Gln Lys Thr Asp Lys Lys Ile Phe Thr Phe Ile Glu
    50                  55                  60

Asn Lys Leu Asp Ile Leu Asn Asn Ser Lys Phe Asn Lys Arg Trp Lys
65                  70                  75                  80

Ser Tyr Gly Thr Pro Asp Asn Ile Asp Lys Asn Met Ser Leu Ile Asn
                85                  90                  95

Lys His Asn Asn Glu Glu Met Phe Asn Asn Tyr Gln Ser Phe Leu
            100                 105                 110

Ser Thr Ser Ser Leu Ile Lys Gln Asn Lys Tyr Val Pro Ile Asn Ala
        115                 120                 125

Val Arg Val Ser Arg Ile Leu Ser Phe Leu Asp Ser Arg Ile Asn Asn
    130                 135                 140

Gly Arg Asn Thr Ser Ser Asn Asn Glu Val Leu Ser Asn Cys Arg Glu
145                 150                 155                 160

Lys Arg Lys Gly Met Lys Trp Asp Cys Lys Lys Asn Asp Arg Ser
                165                 170                 175

Asn Tyr Val Cys Ile Pro Asp Arg Arg Ile Gln Leu Cys Ile Val Asn
            180                 185                 190

Leu Ser Ile Ile Lys Thr Tyr Thr Lys Glu Thr Met Lys Asp His Phe
        195                 200                 205
```

```
Ile Glu Ala Ser Lys Lys Glu Ser Gln Leu Leu Lys Lys Asn Asp
    210                 215                 220

Asn Lys Tyr Asn Ser Lys Phe Cys Asn Asp Leu Lys Asn Ser Phe Leu
225                 230                 235                 240

Asp Tyr Gly His Leu Ala Met Gly Asn Asp Met Asp Phe Gly Tyr
                245                 250                 255

Ser Thr Lys Ala Glu Asn Lys Ile Gln Glu Val Phe Lys Gly Ala His
                260                 265                 270

Gly Glu Ile Ser Glu His Lys Ile Lys Asn Phe Arg Lys Lys Trp Trp
            275                 280                 285

Asn Glu Phe Arg Glu Lys Leu Trp Glu Ala Met Leu Ser Glu His Lys
290                 295                 300

Asn Asn Ile Asn Asn Cys Lys Asn Ile Pro Gln Glu Glu Leu Gln Ile
305                 310                 315                 320

Thr Gln Trp Ile Lys Glu Trp His Gly Glu Phe Leu Leu Glu Arg Asp
                325                 330                 335

Asn Arg Ser Lys Leu Pro Lys Ser Lys Cys Lys Asn Asn Thr Leu Tyr
                340                 345                 350

Glu Ala Cys Glu Lys Glu Cys Ile Asp Pro Cys Met Lys Tyr Arg Asp
                355                 360                 365

Trp Ile Ile Arg Ser Lys Phe Glu Trp His Thr Leu Ser Lys Glu Tyr
370                 375                 380

Glu Thr Gln Lys Val Pro Lys Glu Asn Ala Glu Asn Tyr Leu Ile Lys
385                 390                 395                 400

Ile Ser Glu Asn Lys Asn Asp Ala Lys Val Ser Leu Leu Asn Asn
                405                 410                 415

Cys Asp Ala Glu Tyr Ser Lys Tyr Cys Asp Cys Lys His Thr Thr Thr
                420                 425                 430

Leu Val Lys Ser Val Leu Asn Gly Asn Asp Asn Thr Ile Lys Glu Lys
            435                 440                 445

Arg Glu His Ile Asp Leu Asp Asp Phe Ser Lys Phe Gly Cys Asp Lys
    450                 455                 460

Asn Ser Val Asp Thr Asn Thr Lys Val Trp Glu Cys Lys Lys Pro Tyr
465                 470                 475                 480

Lys Leu Ser Thr Lys Asp Val Cys Val Pro Pro Arg Arg Gln Glu Leu
                485                 490                 495

Cys Leu Gly Asn Ile Asp Arg Ile Tyr Asp Lys Asn Leu Leu Met Ile
                500                 505                 510

Lys Glu His Ile Leu Ala Ile Ala Ile Tyr Glu Ser Arg Ile Leu Lys
            515                 520                 525

Arg Lys Tyr Lys Asn Lys Asp Asp Lys Glu Val Cys Lys Ile Ile Asn
    530                 535                 540

Lys Thr Phe Ala Asp Ile Arg Asp Ile Ile Gly Gly Thr Asp Tyr Trp
545                 550                 555                 560

Asn Asp Leu Ser Asn Arg Lys Leu Val Gly Lys Ile Asn Thr Asn Ser
                565                 570                 575

Asn Tyr Val His Arg Asn Lys Gln Asn Asp Lys Leu Phe Arg Asp Glu
            580                 585                 590

Trp Trp Lys Val Ile Lys Lys Asp Val Trp Asn Val Ile Ser Trp Val
        595                 600                 605

Phe Lys Asp Lys Thr Val Cys Lys Glu Asp Ile Glu Asn Ile Pro
610                 615                 620

Gln Phe Phe Arg Trp Phe Ser Glu Trp Gly Asp Asp Tyr Cys Gln Asp
```

```
              625                 630                 635                 640
Lys Thr Lys Met Ile Glu Thr Leu Lys Val Glu Cys Lys Glu Lys Pro
                    645                 650                 655

Cys Glu Asp Asp Asn Cys Lys Arg Lys Cys Asn Ser Tyr Lys Glu Trp
                    660                 665                 670

Ile Ser Lys Lys Lys Glu Glu Tyr Asn Lys Gln Ala Lys Gln Tyr Gln
                    675                 680                 685

Glu Tyr Gln Lys Gly Asn Asn Tyr Lys Met Tyr Ser Glu Phe Lys Ser
                    690                 695                 700

Ile Lys Pro Glu Val Tyr Leu Lys Lys Tyr Ser Glu Lys Cys Ser Asn
705                 710                 715                 720

Leu Asn Phe Glu Asp Glu Phe Lys Glu Glu Leu His Ser Asp Tyr Lys
                    725                 730                 735

Asn Lys Cys Thr Met Cys Pro Glu Val Lys Asp Val Pro Ile Ser Ile
                    740                 745                 750

Ile Arg Asn Asn Glu Gln Thr Ser Gln Glu Ala Val Pro Glu Glu Ser
                    755                 760                 765

Thr Glu Ile Ala His Arg Thr Glu Thr Arg Thr Asp Glu Arg Lys Asn
770                 775                 780

Gln Glu Pro Ala Asn Lys Asp Leu Lys Asn Pro Gln Gln Ser Val Gly
785                 790                 795                 800

Glu Asn Gly Thr Lys Asp Leu Leu Gln Glu Asp Leu Gly Gly Ser Arg
                    805                 810                 815

Ser Glu Asp Glu Val Thr Gln Glu Phe Gly Val Asn His Gly Ile Pro
                    820                 825                 830

Lys Gly Glu Asp Gln Thr Leu Gly Lys Ser Asp Ala Ile Pro Asn Ile
                    835                 840                 845

Gly Glu Pro Glu Thr Gly Ile Ser Thr Thr Glu Ser Arg His Glu
                    850                 855                 860

Glu Gly His Asn Lys Gln Ala Leu Ser Thr Ser Val Asp Glu Pro Glu
865                 870                 875                 880

Leu Ser Asp Thr Leu Gln Leu His Glu Asp Thr Lys Glu Asn Asp Lys
                    885                 890                 895

Leu Pro Leu Glu Ser Ser Thr Ile Thr Ser Pro Thr Glu Ser Gly Ser
                    900                 905                 910

Ser Asp Thr Glu Glu Thr Pro Ser Ile Ser Glu Gly Pro Lys Gly Asn
                    915                 920                 925

Glu Gln Lys Lys Arg Asp Asp Ser Leu Ser Lys Ile Ser Val Ser
930                 935                 940

Pro Glu Asn Ser Arg Pro Glu Thr Asp Ala Lys Asp Thr Ser Asn Leu
945                 950                 955                 960

Leu Lys Leu Lys Gly Asp Val Asp Ile Ser Met Pro Lys Ala Val Ile
                    965                 970                 975

Gly Ser Ser Pro Asn Asp Asn Ile Asn Val Thr Glu Gln Gly Asp Asn
                    980                 985                 990

Ile Ser Gly Val Asn Ser Lys Pro Leu Ser Asp Asp Val Arg Pro Asp
                    995                1000                1005

Lys Asn His Glu Glu Val Lys Glu His Thr Ser Asn Ser Asp Asn
                    1010                1015                1020

Val Gln Gln Ser Gly Gly Ile Val Asn Met Asn Val Glu Lys Glu
                    1025                1030                1035

Leu Lys Asp Thr Leu Glu Asn Pro Ser Ser Ser Leu Asp Glu Gly
                    1040                1045                1050
```

```
Lys Ala His Glu Glu Leu Ser Glu Pro Asn Leu Ser Ser Asp Gln
1055                1060                1065
Asp Met Ser Asn Thr Pro Gly Pro Leu Asp Asn Thr Ser Glu Glu
1070                1075                1080
Thr Thr Glu Arg Ile Ser Asn Asn Glu Tyr Lys Val Asn Glu Arg
1085                1090                1095
Glu Gly Glu Arg Thr Leu Thr Lys Glu Tyr Glu Asp Ile Val Leu
1100                1105                1110
Lys Ser His Met Asn Arg Glu Ser Asp Asp Gly Glu Leu Tyr Asp
1115                1120                1125
Glu Asn Ser Asp Leu Ser Thr Val Asn Asp Glu Ser Glu Asp Ala
1130                1135                1140
Glu Ala Lys Met Lys Gly Asn Asp Thr Ser Glu Met Ser His Asn
1145                1150                1155
Ser Ser Gln His Ile Glu Ser Asp Gln Gln Lys Asn Asp Met Lys
1160                1165                1170
Thr Val Gly Asp Leu Gly Thr Thr His Val Gln Asn Glu Ile Ser
1175                1180                1185
Val Pro Val Thr Gly Glu Ile Asp Glu Lys Leu Arg Glu Ser Lys
1190                1195                1200
Glu Ser Lys Ile His Lys Ala Glu Glu Glu Arg Leu Ser His Thr
1205                1210                1215
Asp Ile His Lys Ile Asn Pro Glu Asp Arg Asn Ser Asn Thr Leu
1220                1225                1230
His Leu Lys Asp Ile Arg Asn Glu Glu Asn Glu Arg His Leu Thr
1235                1240                1245
Asn Gln Asn Ile Asn Ile Ser Gln Glu Arg Asp Leu Gln Lys His
1250                1255                1260
Gly Phe His Thr Met Asn Asn Leu His Gly Asp Gly Val Ser Glu
1265                1270                1275
Arg Ser Gln Ile Asn His Ser His His Gly Asn Arg Gln Asp Arg
1280                1285                1290
Gly Gly Asn Ser Gly Asn Val Leu Asn Met Arg Ser Asn Asn Asn
1295                1300                1305
Asn Phe Asn Asn Ile Pro Ser Arg Tyr Asn Leu Tyr Asp Lys Lys
1310                1315                1320
Leu Asp Leu Asp Leu Tyr Glu Asn Arg Asn Asp Ser Thr Thr Lys
1325                1330                1335
Glu Leu Ile Lys Lys Leu Ala Glu Ile Asn Lys Cys Glu Asn Glu
1340                1345                1350
Ile Ser Val Lys Tyr Cys Asp His Met Ile His Glu Glu Ile Pro
1355                1360                1365
Leu Lys Thr Cys Thr Lys Glu Lys Thr Arg Asn Leu Cys Cys Ala
1370                1375                1380
Val Ser Asp Tyr Cys Met Ser Tyr Phe Thr Tyr Asp Ser Glu Glu
1385                1390                1395
Tyr Tyr Asn Cys Thr Lys Arg Glu Phe Asp Asp Pro Ser Tyr Thr
1400                1405                1410
Cys Phe Arg Lys Glu Ala Phe Ser Ser Met Pro Tyr Tyr Ala Gly
1415                1420                1425
Ala Gly Val Leu Phe Ile Ile Leu Val Ile Leu Gly Ala Ser Gln
1430                1435                1440
```

| Ala | Lys | Tyr | Gln | Ser | Ser | Glu | Gly | Val | Met | Asn | Glu | Asn | Asn | Glu |
|---|---|---|---|---|---|---|---|---|---|---|---|---|---|---|
| 1445 | | | | | 1450 | | | | | 1455 | | | | |

Asn Asn Phe Leu Phe Glu Val Thr Asp Asn Leu Asp Lys Leu Ser
 1460                    1465                    1470

Asn Met Phe Asn Gln Gln Val Gln Glu Thr Asn Ile Asn Asp Phe
 1475                    1480                    1485

Ser Glu Tyr His Glu Asp Ile Asn Asp Ile Asn Phe Lys Lys
 1490                    1495                    1500

```
<210> SEQ ID NO 14
<211> LENGTH: 4509
<212> TYPE: DNA
<213> ORGANISM: Plasmodium falciparum

<400> SEQUENCE: 14
atgaaatgta atattagtat atatttttt gcttccttct ttgtgttata ttttgcaaaa      60
gctaggaatg aatatgatat aaaagagaat gaaaatttt tagacgtgta taaagaaaaa     120
tttaatgaat tagataaaaa gaaatatgga aatgttcaaa aaactgataa gaaaatattt     180
acttttatag aaaataaatt agatatttta aataattcaa aatttaataa agatggaag      240 agttatggaa ctccagataa tatagataaa aatatgtctt taataaataa acataataat     300
gaagaaatgt ttaacaacaa ttatcaatca ttttttatcga caagttcatt aataaagcaa     360
aataaatatg ttcctattaa cgctgtacgt gtgtctagga tattaagttt cctggattct     420
agaattaata tggaagaaa tacttcatct aataacgaag ttttaagtaa ttgtagggaa     480
aaaaggaaag gaatgaaatg ggattgtaaa agaaaaatg atagaagcaa ctatgtatgt     540
attcctgatc gtagaatcca attatgcatt gttaatctta gcattattaa aacatataca     600
aaagagacca tgaaggatca tttcattgaa gcctctaaaa aagaatctca acttttgctt     660
aaaaaaaatg ataacaaata taattctaaa ttttgtaatg atttgaagaa tagttttta     720 gattatggac atcttgctat gggaaatgat atggattttg gaggttattc aactaaggca     780
gaaaacaaaa ttcaagaagt ttttaagggg gctcatgggg aataagtga acataaaatt     840 aaaaatttta gaaaaaatg gtggaatgaa tttagagaga aactttggga agctatgtta     900
tctgagcata aaaataatat aaataattgt aaaaatattc cccaagaaga attacaaatt     960
actcaatgga taaagaatg gcatggagaa tttttgcttg aaagagataa tagatcaaaa    1020
ttgccaaaaa gtaaatgtaa aaataataca ttatatgaag catgtgagaa ggaatgtatt    1080
gatccatgta tgaaatatag agattggatt attagaagta aatttgaatg gcatacgtta    1140
tcgaaagaat atgaaactca aaaagttcca aaggaaaatg cggaaaatta tttaatcaaa    1200
atttcagaaa acaagaatga tgctaaagta agtttattat tgaataattg tgatgctgaa    1260
tattcaaaat attgtgattg taaacatact actactctcg ttaaaagcgt tttaaatggt    1320
aacgacaata caattaagga aaagcgtgaa catattgatt tagatgattt ttctaaattt    1380
ggatgtgata aaaattccgt tgatacaaac acaaggtgt gggaatgtaa aaaaccttat    1440
aaattatcca ctaaagatgt atgtgtacct ccgaggaggc aagaattatg tcttggaaac    1500
attgatagaa tatacgataa aaacctatta atgataaaag agcatattct tgctattgca    1560
atatatgaat caagaatatt gaaacgaaaa tataagaata aagatgataa agaagtttgt    1620
aaaatcataa ataaaacttt cgctgatata agagatatta taggaggtac tgattattgg    1680
aatgatttga gcaatagaaa attagtagga aaaattaaca caaattcaaa ttatgttcac    1740
aggaataaac aaaatgataa gcttttttcgt gatgagtggt ggaaagttat taaaaaagat    1800
```

```
gtatggaatg tgatatcatg ggtattcaag gataaaactg tttgtaaaga agatgatatt    1860
gaaaatatac cacaattctt cagatggttt agtgaatggg gtgatgatta ttgccaggat    1920
aaaacaaaaa tgatagagac tctgaaggtt gaatgcaaag aaaaaccttg tgaagatgac    1980
aattgtaaac gtaaatgtaa ttcatataaa gaatggatat caaaaaaaaa agaagagtat    2040
aataaacaag ccaaacaata ccaagaatat caaaaaggaa ataattacaa aatgtattct    2100
gaatttaaat ctataaaacc agaagtttat ttaaagaaat actcggaaaa atgttctaac    2160
ctaaatttcg aagatgaatt taaggaagaa ttacattcag attataaaaa taaatgtacg    2220
atgtgtccag aagtaaagga tgtaccaatt tctataataa gaataatga acaaacttcg    2280 caagaagcag ttcctgagga aagcactgaa atagcacaca gaacggaaac tcgtacggat    2340
gaacgaaaaa atcaggaacc agcaaataag gatttaaaga atccacaaca aagtgtagga    2400
gagaacggaa ctaaagattt attacaagaa gatttaggag gatcacgaag tgaagacgaa    2460
gtgacacaag aatttggagt aaatcatgga ataacctaagg gtgaggatca aacgttagga    2520
aaatctgacg ccattccaaa cataggcgaa cccgaaacgg gaatttccac tacagaagaa    2580
agtagacatg aagaaggcca caataaacaa gcattgtcta cttcagtcga tgagcctgaa    2640
ttatctgata cacttcaatt gcatgaagat actaaagaaa atgataaact accccctagaa    2700 tcatctacaa tcacatctcc tacggaaagt ggaagttctg atacagagga aactccatct    2760
atctctgaag gaccaaaagg aaatgaacaa aaaaaacgtg atgacgatag tttgagtaaa    2820
ataagtgtat caccagaaaa ttcaagacct gaaactgatg ctaaagatac ttctaacttg    2880
ttaaaattaa aaggagatgt tgatattagt atgcctaaag cagttattgg gagcagtcct    2940
aatgataata taaatgttac tgaacaaggg gataatattt ccgggggtgaa ttctaaacct    3000 ttatctgatg atgtacgtcc agataaaaat catgaagagg tgaaagaaca tactagtaat    3060
tctgataatg ttcaacagtc tggaggaatt gttaatatga atgttgagaa agaactaaaa    3120
gatactttag aaaatccttc tagtagcttg gatgaaggaa aagcacatga agaattatca    3180
gaaccaaatc taagcagtga ccaagatatg tctaatacac ctggaccttt ggataacacc    3240
agtgaagaaa ctacagaaag aattagtaat aatgaatata aagttaacga gagggaaggt    3300
gagagaacgc ttactaagga atatgaagat attgttttga aaagtcatat gaatagagaa    3360
tcagacgatg gtgaattata tgacgaaaat tcagacttat ctactgtaaa tgatgaatca    3420
gaagacgctg aagcaaaaat gaaaggaaat gatacatctg aaatgtcgca taatagtagt    3480
caacatattg agagtgatca acagaaaaac gatatgaaaa ctgttggtga tttgggaacc    3540
acacatgtac aaaacgaaat tagtgttcct gttacaggag aaattgatga aaaattaagg    3600
gaaagtaaag aatcaaaaat tcataaggct gaagaggaaa gattaagtca tacagatata    3660
cataaaatta tcctgaaga tagaaatagt aatacattac atttaaaaga tataagaaat    3720
gaggaaaacg aaagacactt aactaatcaa aacattaata ttagtcaaga aagggatttg    3780
caaaaacatg gattccatac catgaataat ctacatggag atggagtttc cgaaagaagt    3840
caaattaatc atagtcatca tggaaacaga caagatcggg ggggaaattc tgggaatgtt    3900
ttaaatatga gatctaataa taataatttt aataatattc caagtagata taatttatat    3960
gataaaaaat tagatttaga tctttatgaa aacagaaatg atagtacaac aaaagaatta    4020
ataaagaaat tagcagaaat aaataaatgt gagaacgaaa tttctgtaaa atattgtgac    4080
catatgattc atgaagaaat cccattaaaa acatgcacta aagaaaaaac aagaaatctg    4140
```

-continued

```
tgttgtgcag tatcagatta ctgtatgagc tattttacat atgattcaga ggaatattat    4200
aattgtacga aaagggaatt tgatgatcca tcttatacat gtttcagaaa ggaggctttt    4260
tcaagtatgc catattatgc aggagcaggt gtgttattta ttatattggt tattttaggt    4320
gcttcacaag ccaaatatca aagttctgaa ggagttatga atgagaataa tgagaataat    4380
tttttatttg aagttactga taattagat aaattatcca atatgttcaa tcaacaagta    4440
caggaaacta atatcaacga ttttctgaa taccatgagg atataaatga tattaatttt    4500
aagaaatga                                                            4509
```

<210> SEQ ID NO 15
<211> LENGTH: 2747
<212> TYPE: PRT
<213> ORGANISM: Plasmodium falciparum

<400> SEQUENCE: 15

```
Met Asp Ser Thr Ser Thr Ile Ala Asn Lys Ile Glu Glu Tyr Leu Gly
1               5                   10                  15

Ala Lys Ser Asp Asp Ser Lys Ile Asp Glu Leu Leu Lys Ala Asp Pro
            20                  25                  30

Ser Glu Val Glu Tyr Tyr Arg Ser Gly Gly Asp Gly Asp Tyr Leu Lys
        35                  40                  45

Asn Asn Ile Cys Lys Ile Thr Val Asn His Ser Asp Ser Gly Lys Tyr
    50                  55                  60

Asp Pro Cys Glu Lys Lys Leu Pro Pro Tyr Asp Asn Asp Gln Trp
65                  70                  75                  80

Lys Cys Gln Gln Asn Ser Ser Asp Gly Ser Gly Lys Pro Glu Asn Ile
                85                  90                  95

Cys Val Pro Pro Arg Arg Glu Arg Leu Cys Thr Tyr Asn Leu Glu Asn
            100                 105                 110

Leu Lys Phe Asp Lys Ile Arg Asp Asn Asn Ala Phe Leu Ala Asp Val
        115                 120                 125

Leu Leu Thr Ala Arg Asn Glu Gly Glu Lys Ile Val Gln Asn His Pro
    130                 135                 140

Asp Thr Asn Ser Ser Asn Val Cys Asn Ala Leu Glu Arg Ser Phe Ala
145                 150                 155                 160

Asp Leu Ala Asp Ile Ile Arg Gly Thr Asp Gln Trp Lys Gly Thr Asn
                165                 170                 175

Ser Asn Leu Glu Lys Asn Leu Lys Gln Met Phe Ala Lys Ile Arg Glu
            180                 185                 190

Asn Asp Lys Val Leu Gln Asp Lys Tyr Pro Lys Asp Gln Lys Tyr Thr
        195                 200                 205

Lys Leu Arg Glu Ala Trp Trp Asn Ala Asn Arg Gln Lys Val Trp Glu
    210                 215                 220

Val Ile Thr Cys Gly Ala Arg Ser Asn Asp Leu Leu Ile Lys Arg Gly
225                 230                 235                 240

Trp Arg Thr Ser Gly Lys Ser Asp Arg Lys Lys Asn Phe Glu Leu Cys
                245                 250                 255

Arg Lys Cys Gly His Tyr Glu Lys Glu Val Pro Thr Lys Leu Asp Tyr
            260                 265                 270

Val Pro Gln Phe Leu Arg Trp Leu Thr Glu Trp Ile Glu Asp Phe Tyr
        275                 280                 285

Arg Glu Lys Gln Asn Leu Ile Asp Asp Met Glu Arg His Arg Glu Glu
    290                 295                 300
```

-continued

```
Cys Thr Arg Glu Asp His Lys Ser Lys Glu Gly Thr Ser Tyr Cys Ser
305                 310                 315                 320

Thr Cys Lys Asp Lys Cys Lys Lys Tyr Cys Glu Cys Val Lys Lys Trp
            325                 330                 335

Lys Thr Glu Trp Glu Asn Gln Glu Asn Lys Tyr Lys Asp Leu Tyr Glu
        340                 345                 350

Gln Asn Lys Asn Lys Thr Ser Gln Lys Asn Thr Ser Arg Tyr Asp Asp
            355                 360                 365

Tyr Val Lys Asp Phe Phe Glu Lys Leu Glu Ala Asn Tyr Ser Ser Leu
    370                 375                 380

Glu Asn Tyr Ile Lys Gly Asp Pro Tyr Phe Ala Glu Tyr Ala Thr Lys
385                 390                 395                 400

Leu Ser Phe Ile Leu Asn Pro Ser Asp Ala Asn Asn Pro Ser Gly Glu
                405                 410                 415

Thr Ala Asn His Asn Asp Glu Ala Cys Asn Cys Asn Glu Ser Gly Ile
            420                 425                 430

Ser Ser Val Gly Gln Ala Gln Thr Ser Gly Pro Ser Ser Asn Lys Thr
            435                 440                 445

Cys Ile Thr His Ser Ser Ile Lys Thr Asn Lys Lys Glu Cys Lys
450                 455                 460

Asp Val Lys Leu Gly Val Arg Glu Asn Asp Lys Asp Leu Lys Ile Cys
465                 470                 475                 480

Val Ile Glu Asp Thr Ser Leu Ser Gly Val Asp Asn Cys Cys Cys Gln
                485                 490                 495

Asp Leu Leu Gly Ile Leu Gln Glu Asn Cys Ser Asp Asn Lys Arg Gly
                500                 505                 510

Ser Ser Ser Asn Asp Ser Cys Asp Asn Lys Asn Gln Asp Glu Cys Gln
            515                 520                 525

Lys Lys Leu Glu Lys Val Phe Ala Ser Leu Thr Asn Gly Tyr Lys Cys
    530                 535                 540

Asp Lys Cys Lys Ser Gly Thr Ser Arg Ser Lys Lys Trp Ile Trp
545                 550                 555                 560

Lys Lys Ser Ser Gly Asn Glu Glu Gly Leu Gln Glu Glu Tyr Ala Asn
                565                 570                 575

Thr Ile Gly Leu Pro Pro Arg Thr Gln Ser Leu Tyr Leu Gly Asn Leu
            580                 585                 590

Pro Lys Leu Glu Asn Val Cys Glu Asp Val Lys Asp Ile Asn Phe Asp
        595                 600                 605

Thr Lys Glu Lys Phe Leu Ala Gly Cys Leu Ile Val Ser Phe His Glu
    610                 615                 620

Gly Lys Asn Leu Lys Lys Arg Tyr Pro Gln Asn Lys Asn Ser Gly Asn
625                 630                 635                 640

Lys Glu Asn Leu Cys Lys Ala Leu Glu Tyr Ser Phe Ala Asp Tyr Gly
                645                 650                 655

Asp Leu Ile Lys Gly Thr Ser Ile Trp Asp Asn Glu Tyr Thr Lys Asp
            660                 665                 670

Leu Glu Leu Asn Leu Gln Asn Asn Phe Gly Lys Leu Phe Gly Lys Tyr
        675                 680                 685

Ile Lys Lys Asn Asn Thr Ala Glu Gln Asp Thr Ser Tyr Ser Ser Leu
    690                 695                 700

Asp Glu Leu Arg Glu Ser Trp Trp Asn Thr Asn Lys Lys Tyr Ile Trp
705                 710                 715                 720

Thr Ala Met Lys His Gly Ala Glu Met Asn Ile Thr Thr Cys Asn Ala
```

```
            725                 730                 735
Asp Gly Ser Val Thr Gly Ser Ser Cys Asp Ile Pro Thr
            740                 745                 750

Ile Asp Leu Ile Pro Gln Tyr Leu Arg Phe Leu Gln Glu Trp Val Glu
            755                 760                 765

Asn Phe Cys Glu Gln Arg Gln Ala Lys Val Lys Asp Val Ile Thr Asn
            770                 775                 780

Cys Lys Ser Cys Lys Glu Ser Gly Asn Lys Cys Lys Thr Glu Cys Lys
785                 790                 795                 800

Thr Lys Cys Lys Asp Glu Cys Glu Lys Tyr Lys Lys Phe Ile Glu Ala
            805                 810                 815

Cys Gly Thr Ala Gly Gly Gly Ile Gly Thr Ala Gly Ser Pro Trp Ser
            820                 825                 830

Lys Arg Trp Asp Gln Ile Tyr Lys Arg Tyr Ser Lys His Ile Glu Asp
            835                 840                 845

Ala Lys Arg Asn Arg Lys Ala Gly Thr Lys Asn Cys Gly Thr Ser Ser
            850                 855                 860

Thr Thr Asn Ala Ala Ala Ser Thr Asp Glu Asn Lys Cys Val Gln Ser
865                 870                 875                 880

Asp Ile Asp Ser Phe Phe Lys His Leu Ile Asp Ile Gly Leu Thr Thr
                885                 890                 895

Pro Ser Ser Tyr Leu Ser Asn Val Leu Asp Asp Asn Ile Cys Gly Ala
            900                 905                 910

Asp Lys Ala Pro Trp Thr Thr Tyr Thr Thr Tyr Thr Thr Thr Glu Lys
            915                 920                 925

Cys Asn Lys Glu Arg Asp Lys Ser Lys Ser Gln Ser Ser Asp Thr Leu
930                 935                 940

Val Val Val Asn Val Pro Ser Pro Leu Gly Asn Thr Pro Tyr Arg Tyr
945                 950                 955                 960

Lys Tyr Ala Cys Gln Cys Lys Ile Pro Thr Asn Glu Glu Thr Cys Asp
            965                 970                 975

Asp Arg Lys Glu Tyr Met Asn Gln Trp Ser Cys Gly Ser Ala Arg Thr
            980                 985                 990

Met Lys Arg Gly Tyr Lys Asn Asp Asn Tyr Glu Leu Cys Lys Tyr Asn
            995                 1000                1005

Gly Val Asp Val Lys Pro Thr Thr Val Arg Ser Asn Ser Ser Lys
            1010                1015                1020

Leu Asp Gly Asn Asp Val Thr Phe Phe Asn Leu Phe Glu Gln Trp
            1025                1030                1035

Asn Lys Glu Ile Gln Tyr Gln Ile Glu Gln Tyr Met Thr Asn Ala
            1040                1045                1050

Asn Ile Ser Cys Ile Asp Glu Lys Glu Val Leu Asp Ser Val Ser
            1055                1060                1065

Asp Glu Gly Thr Pro Lys Val Arg Gly Gly Tyr Glu Asp Gly Arg
            1070                1075                1080

Asn Asn Asn Thr Asp Gln Gly Thr Asn Cys Lys Glu Lys Cys Lys
            1085                1090                1095

Cys Tyr Lys Leu Trp Ile Glu Lys Ile Asn Asp Gln Trp Gly Lys
            1100                1105                1110

Gln Lys Asp Asn Tyr Asn Lys Phe Arg Ser Lys Gln Ile Tyr Asp
            1115                1120                1125

Ala Asn Lys Gly Ser Gln Asn Lys Lys Val Val Ser Leu Ser Asn
            1130                1135                1140
```

```
Phe Leu Phe Phe Ser Cys Trp Glu Glu Tyr Ile Gln Lys Tyr Phe
1145                1150                1155

Asn Gly Asp Trp Ser Lys Ile Lys Asn Ile Gly Ser Asp Thr Phe
    1160                1165                1170

Glu Phe Leu Ile Lys Lys Cys Gly Asn Asn Ser Ala His Gly Glu
    1175                1180                1185

Glu Ile Phe Ser Glu Lys Leu Lys Asn Ala Glu Lys Lys Cys Lys
    1190                1195                1200

Glu Asn Glu Ser Thr Asp Thr Asn Ile Asn Lys Ser Glu Thr Ser
1205                1210                1215

Cys Asp Leu Asn Ala Thr Asn Tyr Ile Arg Gly Cys Gln Ser Lys
1220                1225                1230

Thr Tyr Asp Gly Lys Ile Phe Pro Gly Lys Gly Glu Lys Gln
1235                1240                1245

Trp Ile Cys Lys Asp Thr Ile Ile His Gly Asp Thr Asn Gly Ala
1250                1255                1260

Cys Ile Pro Pro Arg Thr Gln Asn Leu Cys Val Gly Glu Leu Trp
1265                1270                1275

Asp Lys Ser Tyr Gly Gly Arg Ser Asn Ile Lys Asn Asp Thr Lys
1280                1285                1290

Glu Leu Leu Lys Glu Lys Ile Lys Asn Ala Ile His Lys Glu Thr
1295                1300                1305

Glu Leu Leu Tyr Glu Tyr His Asp Thr Gly Thr Ala Ile Ile Ser
1310                1315                1320

Lys Asn Asp Lys Lys Gly Gln Lys Gly Lys Asn Asp Pro Asn Gly
1325                1330                1335

Leu Pro Lys Gly Phe Cys His Ala Val Gln Arg Ser Phe Ile Asp
1340                1345                1350

Tyr Lys Asn Met Ile Leu Gly Thr Ser Val Asn Ile Tyr Glu His
1355                1360                1365

Ile Gly Lys Leu Gln Glu Asp Ile Lys Lys Ile Ile Glu Lys Gly
1370                1375                1380

Thr Pro Gln Gln Lys Asp Lys Ile Gly Gly Val Gly Ser Ser Thr
1385                1390                1395

Glu Asn Val Asn Ala Trp Trp Lys Gly Ile Glu Arg Glu Met Trp
1400                1405                1410

Asp Ala Val Arg Cys Ala Ile Thr Lys Ile Asn Lys Lys Asn Asn
1415                1420                1425

Asn Ser Ile Phe Asn Gly Asp Glu Cys Gly Val Ser Pro Pro Thr
1430                1435                1440

Gly Asn Asp Glu Asp Gln Ser Val Ser Trp Phe Lys Glu Trp Gly
1445                1450                1455

Glu Gln Phe Cys Ile Glu Arg Leu Arg Tyr Glu Gln Asn Ile Arg
1460                1465                1470

Glu Ala Cys Thr Ile Asn Gly Lys Asn Glu Lys Lys Cys Ile Asn
1475                1480                1485

Ser Lys Ser Gly Gln Gly Asp Lys Ile Gln Gly Ala Cys Lys Arg
1490                1495                1500

Lys Cys Glu Lys Tyr Lys Lys Tyr Ile Ser Glu Lys Lys Gln Glu
1505                1510                1515

Trp Asp Lys Gln Lys Thr Lys Tyr Glu Asn Lys Tyr Val Gly Lys
1520                1525                1530
```

```
Ser Ala Ser Asp Leu Leu Lys Glu Asn Tyr Pro Glu Cys Ile Ser
1535                1540                1545

Ala Asn Phe Asp Phe Ile Phe Asn Asp Asn Ile Glu Tyr Lys Thr
1550                1555                1560

Tyr Tyr Pro Tyr Gly Asp Tyr Ser Ser Ile Cys Ser Cys Glu Gln
1565                1570                1575

Val Lys Tyr Tyr Lys Tyr Asn Asn Ala Glu Lys Lys Asn Asn Lys
1580                1585                1590

Ser Leu Cys Tyr Glu Lys Asp Asn Asp Met Thr Trp Ser Lys Lys
1595                1600                1605

Tyr Ile Lys Lys Leu Glu Asn Gly Arg Ser Leu Glu Gly Val Tyr
1610                1615                1620

Val Pro Pro Arg Arg Gln Gln Leu Cys Leu Tyr Glu Leu Phe Pro
1625                1630                1635

Ile Ile Ile Lys Asn Glu Glu Gly Met Glu Lys Ala Lys Glu Glu
1640                1645                1650

Leu Leu Glu Thr Leu Gln Ile Val Ala Glu Arg Glu Ala Tyr Tyr
1655                1660                1665

Leu Trp Lys Gln Tyr Asn Pro Thr Gly Lys Gly Ile Asp Asp Ala
1670                1675                1680

Asn Lys Lys Ala Cys Cys Ala Ile Arg Gly Ser Phe Tyr Asp Leu
1685                1690                1695

Glu Asp Ile Ile Lys Gly Asn Asp Leu Val His Asp Glu Tyr Thr
1700                1705                1710

Lys Tyr Ile Asp Ser Lys Leu Asn Glu Ile Phe Gly Ser Ser Asn
1715                1720                1725

Thr Asn Asp Ile Asp Thr Lys Arg Ala Arg Thr Asp Trp Trp Glu
1730                1735                1740

Asn Glu Thr Ile Thr Asn Gly Thr Asp Arg Lys Thr Ile Arg Gln
1745                1750                1755

Leu Val Trp Asp Ala Met Gln Ser Gly Val Arg Tyr Ala Val Glu
1760                1765                1770

Glu Lys Asn Glu Asn Phe Pro Leu Cys Met Gly Val Glu His Ile
1775                1780                1785

Gly Ile Ala Lys Pro Gln Phe Ile Arg Trp Leu Glu Glu Trp Thr
1790                1795                1800

Asn Glu Phe Cys Glu Lys Tyr Thr Lys Tyr Phe Glu Asp Met Lys
1805                1810                1815

Ser Lys Cys Asp Pro Pro Lys Arg Ala Asp Thr Cys Gly Asp Asn
1820                1825                1830

Ser Asn Ile Glu Cys Lys Lys Ala Cys Ala Asn Tyr Thr Asn Trp
1835                1840                1845

Leu Asn Pro Lys Arg Ile Glu Trp Asn Gly Met Ser Asn Tyr Tyr
1850                1855                1860

Asn Lys Ile Tyr Arg Lys Ser Asn Lys Glu Ser Glu Asp Gly Lys
1865                1870                1875

Asp Tyr Ser Met Ile Met Ala Pro Thr Val Ile Asp Tyr Leu Asn
1880                1885                1890

Lys Arg Cys His Gly Glu Ile Asn Gly Asn Tyr Ile Cys Cys Ser
1895                1900                1905

Cys Lys Asn Ile Gly Ala Tyr Asn Thr Thr Ser Gly Thr Val Asn
1910                1915                1920

Lys Lys Leu Gln Lys Lys Glu Thr Glu Cys Glu Glu Glu Lys Gly
```

-continued

```
            1925                1930                1935

Pro Leu Asp Leu Met Asn Glu Val Leu Asn Lys Met Asp Lys Lys
        1940                1945                1950

Tyr Ser Ala His Lys Met Lys Cys Thr Glu Val Tyr Leu Glu His
    1955                1960                1965

Val Glu Gln Leu Asn Glu Ile Asp Asn Ala Ile Lys Asp Tyr
    1970                1975                1980

Lys Leu Tyr Pro Leu Asp Arg Cys Phe Asp Asp Gln Thr Lys Met
    1985                1990                1995

Lys Val Cys Asp Leu Ile Ala Asp Ala Ile Gly Cys Lys Asp Lys
    2000                2005                2010

Thr Lys Leu Asp Glu Leu Asp Glu Trp Asn Asp Met Asp Leu Arg
    2015                2020                2025

Gly Thr Tyr Asn Lys His Lys Gly Val Leu Ile Pro Pro Arg Arg
    2030                2035                2040

Arg Gln Leu Cys Phe Ser Arg Ile Val Arg Gly Pro Ala Asn Leu
    2045                2050                2055

Arg Ser Leu Asn Glu Phe Lys Glu Glu Ile Leu Lys Gly Ala Gln
    2060                2065                2070

Ser Glu Gly Lys Phe Leu Gly Asn Tyr Tyr Lys Glu His Lys Asp
    2075                2080                2085

Lys Glu Lys Ala Leu Glu Ala Met Lys Asn Ser Phe Tyr Asp Tyr
    2090                2095                2100

Glu Asp Ile Ile Lys Gly Thr Asp Met Leu Thr Asn Ile Glu Phe
    2105                2110                2115

Lys Asp Ile Lys Ile Lys Leu Asp Arg Leu Leu Glu Lys Glu Thr
    2120                2125                2130

Asn Asn Thr Lys Lys Ala Glu Asp Trp Trp Lys Thr Asn Lys Lys
    2135                2140                2145

Ser Ile Trp Asn Ala Met Leu Cys Gly Tyr Lys Lys Ser Gly Asn
    2150                2155                2160

Lys Ile Ile Asp Pro Ser Trp Cys Thr Ile Pro Thr Thr Glu Thr
    2165                2170                2175

Pro Pro Gln Phe Leu Arg Trp Ile Lys Glu Trp Gly Thr Asn Val
    2180                2185                2190

Cys Ile Gln Lys Gln Glu His Lys Glu Tyr Val Lys Ser Lys Cys
    2195                2200                2205

Ser Asn Val Thr Asn Leu Gly Ala Gln Ala Ser Glu Ser Asn Asn
    2210                2215                2220

Cys Thr Ser Glu Ile Lys Lys Tyr Gln Glu Trp Ser Arg Lys Arg
    2225                2230                2235

Ser Ile Gln Trp Glu Thr Ile Ser Lys Arg Tyr Lys Lys Tyr Lys
    2240                2245                2250

Arg Met Asp Ile Leu Lys Asp Val Lys Glu Pro Asp Ala Asn Thr
    2255                2260                2265

Tyr Leu Arg Glu His Cys Ser Lys Cys Pro Cys Gly Phe Asn Asp
    2270                2275                2280

Met Glu Glu Met Asn Asn Asn Glu Asp Asn Glu Lys Glu Ala Phe
    2285                2290                2295

Lys Gln Ile Lys Glu Gln Val Lys Ile Pro Ala Glu Leu Glu Asp
    2300                2305                2310

Val Ile Tyr Arg Ile Lys His His Glu Tyr Asp Lys Gly Asn Asp
    2315                2320                2325
```

-continued

```
Tyr Ile Cys Asn Lys Tyr Lys Asn Ile His Asp Arg Met Lys Lys
    2330                2335                2340

Asn Asn Gly Asn Phe Val Thr Asp Asn Phe Val Lys Lys Ser Trp
    2345                2350                2355

Glu Ile Ser Asn Gly Val Leu Ile Pro Pro Arg Arg Lys Asn Leu
    2360                2365                2370

Phe Leu Tyr Ile Asp Pro Ser Lys Ile Cys Glu Tyr Lys Lys Asp
    2375                2380                2385

Pro Lys Leu Phe Lys Asp Phe Ile Tyr Trp Ser Ala Phe Thr Glu
    2390                2395                2400

Val Glu Arg Leu Lys Lys Ala Tyr Gly Gly Ala Arg Ala Lys Val
    2405                2410                2415

Val His Ala Met Lys Tyr Ser Phe Thr Asp Ile Gly Ser Ile Ile
    2420                2425                2430

Lys Gly Asp Asp Met Met Glu Lys Asn Ser Ser Asp Lys Ile Gly
    2435                2440                2445

Lys Ile Leu Gly Asp Thr Asp Gly Gln Asn Glu Lys Arg Lys Lys
    2450                2455                2460

Trp Trp Asp Met Asn Lys Tyr His Ile Trp Glu Ser Met Leu Cys
    2465                2470                2475

Gly Tyr Arg Glu Ala Glu Gly Asp Thr Glu Thr Asn Glu Asn Cys
    2480                2485                2490

Arg Phe Pro Asp Ile Glu Ser Val Pro Gln Phe Leu Arg Trp Phe
    2495                2500                2505

Gln Glu Trp Ser Glu Asn Phe Cys Asp Arg Arg Gln Lys Leu Tyr
    2510                2515                2520

Asp Lys Leu Asn Ser Glu Cys Ile Ser Ala Glu Cys Thr Asn Gly
    2525                2530                2535

Ser Val Asp Asn Ser Lys Cys Thr His Ala Cys Val Asn Tyr Lys
    2540                2545                2550

Asn Tyr Ile Leu Thr Lys Lys Thr Glu Tyr Glu Ile Gln Thr Asn
    2555                2560                2565

Lys Tyr Asp Asn Glu Phe Lys Asn Lys Asn Ser Asn Asp Lys Asp
    2570                2575                2580

Ala Pro Asp Tyr Leu Lys Glu Lys Cys Asn Asp Asn Lys Cys Glu
    2585                2590                2595

Cys Leu Asn Lys His Ile Asp Asp Lys Asn Lys Thr Trp Lys Asn
    2600                2605                2610

Pro Tyr Glu Thr Leu Glu Asp Thr Phe Lys Ser Lys Cys Asp Cys
    2615                2620                2625

Pro Lys Pro Leu Pro Ser Pro Ile Lys Pro Asp Asp Leu Pro Pro
    2630                2635                2640

Gln Ala Asp Glu Pro Phe Asp Pro Thr Ile Leu Gln Thr Thr Ile
    2645                2650                2655

Pro Phe Gly Ile Ala Leu Ala Leu Gly Ser Ile Ala Phe Leu Phe
    2660                2665                2670

Met Lys Val Ile Tyr Ile Tyr Ile Tyr Ile Cys Val Val Tyr Val
    2675                2680                2685

Cys Met Tyr Val Cys Met Tyr Val Cys Met Tyr Val Cys Met Tyr
    2690                2695                2700

Val Cys Met Tyr Val Cys Met Tyr Val Cys Tyr Val Tyr Met Leu
    2705                2710                2715
```

| Tyr | Met | Tyr | Leu | Lys | Tyr | Val | Phe | Ile | Leu | Lys | Lys | Lys | Gly |
| | 2720 | | | | 2725 | | | | 2730 | | | | |

| Lys | Ser | Asn | Ile | Gly | Ile | Tyr | Leu | Leu | Lys | Lys | Lys | Arg | Glu |
| | 2735 | | | | 2740 | | | | 2745 | | | | |

<210> SEQ ID NO 16
<211> LENGTH: 8244
<212> TYPE: DNA
<213> ORGANISM: Plasmodium falciparum

<400> SEQUENCE: 16

```
atggatagta caagcactat tgctaacaaa attgaagaat atttaggtgc aaaatccgat      60
gattctaaaa tagcgaatt gttgaaagct gatcctagtg aagtggaata ctatagaagt     120
ggaggtgatg gagattactt aaaaaataat atttgtaaaa ttaccgtgaa tcattcagat     180
tctggaaagt atgatccttg tgaaaaaaaa ttacctcctt atgatgataa tgaccaatgg     240
aaatgtcagc aaaattcatc tgatggaagt ggaaaacctg aaaatatatg tgtccctccg     300
agaagagaaa gattatgtac gtataattta gaaaacttaa atttgataa aattagggat      360
aataatgcat ttttggctga tgtattactt acagctagaa atgaaggaga aaaaatagtg     420
cagaatcatc cagatacaaa tagttccaat gtttgtaatg ctttagaaag aagttttgct     480
gatcttgcag atattattag aggtacagat caatggaaag gtactaatag taatttagaa     540
aaaaatttaa aacaaatgtt tgcaaaaata cgagaaacg acaaggtact tcaagataaa      600
tacccaaagg accaaaaata tacaaaatta cgagaagctt ggtggaatgc taatagacaa     660
aaggtgtggg aagttattac ttgcggtgca cgaagtaacg atttactcat aaaacgtgga     720
tggagaacat ctggaaaatc tgatagaaaa aagaacttcg aattgtgccg caaatgtggc     780
cattatgaaa aagaggttcc taccaaatta gattatgtcc ctcaattctt aaggtggtta     840
acagaatgga tagaggattt ttatagagag aagcaaaatc tgatcgatga catggagagg     900
caccgtgaag agtgtacaag agaggatcat aaatctaaag aaggtacatc atattgtagt     960
acctgtaaag acaaatgtaa gaaatattgt gaatgtgtga agaaatggaa gaccgaatgg    1020
gaaaatcaag aaaataaata taagattta tatgaacaaa acaaaaacaa aacttcgcaa     1080
aaaaatacat caagatatga tgattatgtt aaagattttt ttgaaaaact tgaagctaat    1140
tattcgtctc ttgaaaatta tataaagggt gatccttatt tcgcagaata tgcaaccaaa    1200
ttatcattta ttttaaatcc atcagatgct aataatccgt ctggagaaac agcaaaccat    1260
aatgatgaag catgtaactg taatgaatca ggaatttcat cagttggaca ggcacaaaca    1320
tcgggtccgt cgtcgaataa aacatgtatc acacatagct ctataaaaac taataagaaa    1380
aaagaatgta agatgtaaa gttgggtgtt cgtgaaaatg ataaagattt gaaaatatgc     1440
gtaattgagg acacttcctt aagtggtgtt gataattgtt gttgccaaga tttattggga    1500
attcttcaag aaaattgtag tgataataaa cgtggatcta gttctaatga tagttgtgat    1560
aacaaaaatc aggatgaatg tcaaaagaaa ttagaaaaag tatttgcatc tttaacgaat    1620
ggttataaat gcgacaaatg taaatctgga acatcaagaa gtaaaaaaaa atggatatgg    1680
aaaaaatcct ctggtaatga agaaggatta caagaagaat atgctaacac cataggttta    1740
cccccaagaa cacaatcgtt atatttagga aatctaccta aacttgaaaa tgtgtgcgaa    1800
gatgtaaagg atattaattt tgatacaaaa gagaaatttc tagcaggatg cttaattgtt    1860
tcttttcatg aaggaaaaaa tttaaaaaaa agatacctc aaaataaaaa ttctggaaat    1920
aaagaaaatt tatgcaaagc tttagaatat agttttgctg attatggaga tttaattaaa    1980
```

```
ggtacaagta tatgggataa tgaatataca aaagatctgg aactaaattt acaaaacaat    2040
tttggaaaac tttttggtaa atatataaaa aagaataata ctgctgaaca agatacttca    2100
tattcttctc ttgatgaatt aagagaatca tggtggaaca cgaacaaaaa atatatttgg    2160
acagcaatga aacatggtgc agaaatgaat attactacgt gtaatgctga tggtagtgtc    2220
actggtagtg gtagtagttg tgatgatatt cctacgattg atttgatccc gcaatattta    2280
cgttttttgc aagaatgggt agaaaatttt tgcgaacaac gtcaagcaaa agtaaaagat    2340
gtgataacga actgtaagtc gtgtaaggaa agtggaaaca aatgtaaaac tgaatgtaaa    2400
acaaaatgta aagacgagtg tgaaaaatac aaaaaattta ttgaagcgtg tggtacagct    2460
ggtggtggta ttggtactgc tggatctcca tggagcaaaa ggtgggacca aatatataag    2520
aggtattcca aacatataga agacgcgaaa cgaaaccgta aagcgggcac aaaaaattgt    2580
ggtacaagta gtactacaaa tgctgccgca agtactgatg aaaataaatg tgtacaatca    2640
gatatcgatt cgttttttcaa acacttaatt gatataggat tgaccacacc gtcttcttat    2700
ttatcaaatg tacttgatga caacatatgt ggcgcggaca aagctccatg gacaacatac    2760
acgacataca cgacaacaga aaaatgtaat aaagaaagag ataaatcaaa gtcacaatca    2820
agtgatacgc ttgtggttgt aaatgttccg tctccactgg gcaacactcc ataccgatat    2880
aaatacgcat gccagtgtaa aataccaact aatgaagaaa catgtgatga tagaaaagaa    2940
tatatgaatc aatggagttg tggtagcgca cgaactatga aacgtggtta taaaaatgac    3000
aactacgaat tatgtaaata taatggtgta gatgtaaaac cgacaacagt tagatcaaat    3060
agctctaaat tagatggaaa tgatgtgacg ttctttaatt tgtttgaaca gtggaacaaa    3120
gaaatacaat atcagataga gcagtatatg acaaatgcga atatatcgtg cattgacgaa    3180
aaagaagtat tggatagtgt gtcagacgaa ggtactccta agtacgtggg tggttatgaa    3240
gatggtagaa ataacaatac cgatcagggt acgaactgca aagaaaaatg taaatgttac    3300
aaattatgga tagaaaaaat taatgatcag tggggaaaac agaaagacaa ttataataaa    3360
tttcgaagta aacaaattta tgatgcaaat aaaggttctc agaataaaaa agttgttagt    3420
ttatctaatt ttttgttttt ttcatgttgg gaagaatata tacaaaaata tttcaatggc    3480
gattggagta aaattaagaa tataggatct gatacgtttg agtttttaat aaaaaaatgt    3540
ggaaacaatt cagctcatgg agaagaaata tttagtgaaa aattgaaaaa tgcagaaaaa    3600
aaatgtaagg aaaatgaaag tacagatacc aatattaata aaagtgaaac atcatgtgac    3660
cttaacgcaa ccaattatat tcgtgggtgt caatcaaaaa cttacgatgg aaaaatattt    3720
ccaggtaaag gaggcgagaa acaatggata tgtaaagata ctataataca tggagataca    3780
aatggtgcct gtatcccgcc aagaacacaa aattatgtg ttggagagtt atgggataaa    3840
agttatggtg gaaggagtaa cattaaaaat gatacaaagg aattattaaa agagaaaata    3900
aaaaatgcta tacacaaaga aacagaatta ttgtatgaat accacgatac aggtacagca    3960
attatatcaa aaaatgataa aaaaggacaa aaaggaaaaa atgatcctaa tggattgcca    4020
aaaggttttt gtcatgctgt tcaaagaagt tttattgatt ataagaatat gattttgggt    4080
acaagtgtaa atatatatga acacattgga aaattacaag aagatataaa aaaaattatc    4140
gaaaaaggaa cacctcaaca aaaagacaaa ataggtggtg ttggtagtag tacagaaaac    4200
gtaaatgctt ggtggaaagg aattgaaagg gagatgtggg atgcagtaag atgtgctata    4260
acaaaaataa ataaaaaaaa taataatagt atatttaatg gtgatgagtg tggggtatcc    4320
```

```
cccccaacag gaaatgatga ggatcagtcc gtttcgtggt ttaaagaatg gggcgaacag    4380
ttttgtatag aacgattacg atatgaacaa aatatacgtg aagcttgtac tattaatggt    4440
aagaatgaaa agaaatgtat taattcaaaa agtggtcaag gagataaaat acaaggagca    4500
tgtaaaagaa aatgtgaaaa atataaaaaa tatatttctg aaaaaaaaca gaatgggac     4560 aaacaaaaaa caaaatatga aaataaatat gtaggaaaat ctgcgagtga tttattgaaa    4620
gaaaattatc ctgaatgtat atcagcaaat tttgatttta tatttaacga taatattgaa    4680
tataagacat attatccata tggagattat agcagtatat gttcgtgcga acaagtaaaa    4740
tattacaaat ataataatgc tgagaaaaaa aataataaat cgctttgtta tgaaaaagat    4800
aatgatatga catggagtaa aaaatatata aaaaaattgg aaaatggtcg atcattagag    4860
ggagtatacg tcccccccaag acggcaacaa ttatgtcttt atgaactatt ccaataatt    4920 ataaaaaacg aagaaggtat ggaaaaggca aagaagaat tattggaaac attacaaata    4980
gttgcagaga gagaagcata ttatttatgg aaacagtata atccaactgg taaaggaatt    5040
gatgatgcga ataagaaagc ttgttgtgcc attcgtggaa gttttatga tttgaagat     5100 attattaaag gcaacgattt agtgcatgac gaatacacga aatatataga cagtaaatta    5160
aacgaaattt tcggtagtag taatacaaat gatatagata caaaacgtgc gcgtacagat    5220
tggtgggaaa acgaaaccat tactaatgga actgatcgta aaacaattag gcagctagta    5280
tgggatgcta tgcaatctgg agtaagatat gcagtagaag agaaaacga aattttcct     5340 ctatgtatgg gagttgaaca tataggaata gccaaacctc aatttataag atggttggaa    5400
gaatggacaa atgagttttg tgagaaatat acaaatatt tcgaagatat gaaatccaaa    5460
tgtgatcccc ccaaacgtgc tgatacttgt ggtgataata gtaatatcga atgtaaaaaa    5520
gcatgtgcaa attatacgaa ttggtttaaat ccaaaaagga tagaatgaa tggaatgagc    5580 aattattata taaaaatata ccgtaaaagt aacaaagaat cggaagatgg aaaagattat    5640
tcaatgatta tggcacctac agtcattgac tatttgaaca aaagatgcca tggcgaaatt    5700
aatgggaact acatttgttg tagttgtaaa aatataggtg catataacac cacttcaggt    5760
acagttaata aaaaactaca aaaaaaggaa acagaatgtg aagaagaaaa aggacctcta    5820
gatttaatga acgaggtatt aaataaaatg gacaaaaaat atagcgcgca aagatgaag    5880 tgcacagaag tttacttgga acatgttgaa gaacaattaa acgaaattga caatgcaata    5940
aaagattaca agttatatcc tttagataga tgttttgatg atcagacaaa aatgaaggtg    6000
tgtgatttaa ttgcagatgc tataggatgt aaggataaaa caaaactgga tgaactggat    6060
gaatggaatg atatggacct gcgaggtact tataataagc ataaggtgt tttaattcct     6120 cctagacgta gacaattatg tttctcaagg attgtgagag gtcccgcaaa tttaagaagc    6180
ttaaatgaat ttaagaaga aattttaaaa ggagcccaat cggaaggtaa gtttttgggt    6240
aattattata agaacataa agataaagaa aaggcgctag aagctatgaa aaacagtttt    6300
tacgattatg aagatataat aaaaggtact gatatgttaa caaatataga attcaaggat    6360
attaaaataa aactagacag attactagaa aaagagacta ataataccaa aaaagctgaa    6420
gattggtgga aaacaaataa gaaatctata tggaatgcta tgttatgtgg gtacaagaaa    6480
tctgggaata aaataataga tccatcatgg tgtaccatac ctactacaga aacccctccg    6540 caattttac gatggataaa agaatgggga acaaatgtgt gtatacaaaa acaagagcat    6600
aaagaatacg ttaaatcaaa atgttctaat gttactaatt taggggcaca agcatcgaaa    6660
tcaaataatt gtacatcaga aattaaaaaaa tatcaagaat ggagcaggaa aaggtctatt    6720
```

```
cagtgggaaa ctatatcgaa aagatataaa aaatataaac gtatggatat attaaaagat    6780
gtaaaggaac cagatgctaa tacatattta agggaacatt gttctaaatg tccgtgtgga    6840
tttaatgata tggaagaaat gaataacaat gaagacaacg aaaagaagc atttaagcaa     6900 ataaaagaac aagttaagat tccagctgaa cttgaagacg ttatttaccg aataaaacat    6960
catgagtatg ataaaggtaa tgattatatt tgtaataaat ataaaaatat acacgatcgt    7020
atgaaaaaaa ataatggtaa ttttgtgact gataatttcg ttaaaaaatc ttgggaaatt    7080
agtaatggtg tgctaatacc tccacgaaga aaaaatttgt ttctgtacat tgatccatca    7140
aaaatatgtg aatataaaaa ggatcctaaa ttgtttaaag atttcattta ttggtcggca    7200
tttactgaag ttgaaaggtt aaaaaaagcg tatggtgggg ctagagcgaa agttgttcat    7260
gcaatgaaat atagttttac cgatatagga agtattatca aaggtgatga tatgatggaa    7320
aagaattcgt ctgataagat aggtaaaatt ttgggagata cagatggaca gaatgaaaaa    7380
cgtaaaaaat ggtgggacat gaataaatat cacatatggg aatccatgtt atgcggatat    7440
agagaagctg agggcgacac agaaacgaac gaaaattgca ggtttcctga tattgaatct    7500
gttccccaat ttctacgatg gtttcaagaa tggagcgaaa atttctgtga tagacgacaa    7560
aaattatatg ataaattgaa tagtgaatgt atatctgctg aatgcactaa tggatctgtt    7620
gataattcta aatgtactca tgcatgtgta aattataaaa attatatttt aacaaaaaaa    7680
acagaatatg aaattcaaac aaataaatat gataatgaat ttaaaaacaa aaatagtaat    7740
gataaagacg ccccagatta cttaaaagag aaatgtaatg ataataaatg tgaatgtctc    7800
aataaacata ttgatgataa aaacaaaaca tggaaaaatc cttatgaaac tctggaggac    7860
actttcaaaa gcaaatgtga ttgcccaaaa ccttttaccat cccctataaa acctgatgac    7920
ttaccccccc aagccgatga accgtttgac ccaactatac tacaaacaac cattccttttt   7980 ggtattgcgt tggcgttagg gtcgatcgct ttccttttca tgaaggtaat atatatatat    8040 atatatat gtgttgtata tgtatgtatg tatgtatgta tgtatgtatg tatgtatgta     8100
tgtatgtatg tatgtatgta tgtatgtatg tatgtatgtt atgtgtatat gttatatatg   8160
tatttaaaat atgtatttat attgaaaaag aaaaaaggaa aaagtaatat aggaatatat   8220
ctattaaaaa aaaaaagaga gtga                                          8244
```

<210> SEQ ID NO 17
<211> LENGTH: 362
<212> TYPE: PRT
<213> ORGANISM: Plasmodium falciparum

<400> SEQUENCE: 17

Glu His Ile Cys Asp Phe Thr Lys Glu Lys Tyr Leu Leu Gly Lys Asn
1               5                   10                  15

Glu Lys Glu Tyr Cys Val Val Asn Ala Lys Pro Phe Asp Ser Val Thr
            20                  25                  30

Phe Ile Cys Pro Lys Lys Ile Gly Ala Gln Cys Phe Gln Asn Val Asn
        35                  40                  45

Thr Leu Asp Asp Ile Ser Ala Asp Lys Met Glu Ser Ser Lys Leu Ser
    50                  55                  60

Ile Asp Glu Leu Leu Tyr Gly Ser Thr Leu Tyr Gly Asp Thr Leu Leu
65                  70                  75                  80

Ile Ser Pro Thr Val Lys Gln Ser Thr Thr Phe Tyr Cys Phe Cys Asn
                85                  90                  95

| | | | | | | | | | | | |
|---|---|---|---|---|---|---|---|---|---|---|---|
|Leu|Gln|Met|Glu|Asp|Leu|Lys|Lys|Tyr|Leu|Lys|Lys|Arg|Arg|Leu|Thr|
| | |100| | | |105| | | |110| |

Lys Glu Lys Glu Asn Ala Lys Lys Lys Ser Thr Val Asn Val Asn Asp
     115             120              125

Leu Lys Asn Ala Asp Glu Asp Met Glu Val Val Val Pro Glu Lys Gln
     130             135              140

Ile Asp Glu His Leu Val Arg Ala Leu Tyr Arg Val Lys Lys Ile Arg
145             150              155              160

Asn Ile Ile Glu Arg Glu Lys Asn Lys Gly Glu Gly Asp Lys Pro Thr
     165             170              175

Asn Pro Glu Asp Glu Glu Glu Leu Val Ile Glu Glu Gln Glu Glu
     180             185              190

Glu Asp Gly Glu Gly Asp Glu Glu Asp Glu Ser Lys Val Glu Lys Ile
     195             200              205

Ile Thr Lys Tyr Gly Ile Met Lys Val Val Val Ser Thr Asn Asn Thr
     210             215              220

Ile Thr Lys Gly Cys Asp Phe Gly Asn Asn Val Val Asn Tyr Phe Ser
225             230              235              240

Lys Pro Tyr Pro Val Glu Arg Tyr Gly Gly Ser Lys Val Cys Arg Ile
             245              250              255

Glu Ala Lys Pro Gly Glu Phe Val Gly Phe Lys Cys Ile Tyr Asp Asn
     260             265              270

Gln Gly Thr Val Glu Pro His Asn Cys Phe Asp Lys Val Phe Tyr Glu
             275              280              285

Gly Lys Glu Thr Asp Leu Gln Thr Leu Met Pro Gly Tyr Ile Ser Tyr
     290             295              300

Gly Asn Lys Gln Lys Gly Lys Tyr Ala Phe Tyr Leu Lys Leu Pro His
305             310              315              320

Phe Val Gln His Ser Tyr Thr Val Gln Cys Lys Cys Met Ser Thr Val
             325              330              335

Ser Gln Phe Asp Asn Tyr Val Phe Glu Leu Ala Val Glu Gly Gly Glu
     340             345              350

Ser Asp Ile Val Ala Lys Ser Phe Gln Glu
     355             360

<210> SEQ ID NO 18
<211> LENGTH: 1086
<212> TYPE: DNA
<213> ORGANISM: Plasmodium falciparum

<400> SEQUENCE: 18

```
gaacacatct gcgattttac gaaggagaag taccttctgg ggaagaatga aaaggaatac     60
tgcgtggtga acgcgaagcc gtttgacagc gtaacattta tatgcccgaa gaaaatagga    120
gcacagtgct ttcagaatgt taacacgcta gacgatataa gtgcagacaa aatggaatcg    180
tccaagctgt ccatagatga gctgctatac gggtcgaccc tgtatggaga cacgctgctc    240
atatcgccca cggtgaagca gagcacaacc ttctactgtt tctgtaactt gcaaatggag    300
gacctgaaaa agtacctaaa gaagaggaga ctaaccaagg aaaaggaaaa tgcgaaaaag    360
aaatccactg tcaatgtgaa cgatttgaaa aatgcagacg aagatatgga ggtggtagtc    420
ccggagaagc aaatagatga acacctagtt agagcattat atagggtaaa aaaaattagg    480
aatataatag agcgtgaaaa gaacaaaggg gagggagata agcccacaaa tccggaagac    540
gaagaagaac tcgtaattga ggaggagcag gaagaagagg atggagaagg ggatgaagag    600
```

```
gatgaaagta aagttgaaaa aatcattaca aagtatggaa taatgaaagt tgttgtttct    660
acgaataata caattactaa gggatgcgat tcggaaata atgtggtgaa ttattttct     720 aagccctacc ctgttgagag gtatggaggt agtaaagtct gcagaattga ggcgaagcca   780
ggagagtttg tcggcttcaa gtgcatatat gataaccagg gtaccgtcga accgcacaat   840
tgctttgata aggtctttta cgagggtaaa gaaaccgatt tgcagaccct catgcctggc   900
tatatatcat atggaaacaa gcagaagggg aaatacgcct tttacctgaa gctgccccac   960
tttgtgcaac acagctacac cgttcagtgc aagtgcatgt ccactgtgtc gcagttcgat   1020
aactacgtct tcgagttggc cgtggagggc ggcgagagcg atattgttgc caagtccttc   1080
caggag                                                              1086
```

<210> SEQ ID NO 19
<211> LENGTH: 427
<212> TYPE: PRT
<213> ORGANISM: Plasmodium falciparum

<400> SEQUENCE: 19

```
Ile Ile Asn Ile Ile Leu Phe Tyr Phe Phe Leu Trp Val Lys Lys Ser
1               5                   10                  15

Ile Ser Asp Leu Leu Ser Ser Thr Gln Tyr Val Cys Asp Phe Tyr Phe
            20                  25                  30

Asn Pro Leu Thr Asn Val Lys Pro Thr Val Val Gly Ser Ser Glu Ile
        35                  40                  45

Tyr Glu Glu Val Gly Cys Thr Ile Asn Asn Pro Thr Leu Gly Asp His
    50                  55                  60

Ile Val Leu Ile Cys Pro Lys Lys Asn Asn Gly Asp Phe Ser Asn Ile
65                  70                  75                  80

Glu Ile Val Pro Thr Asn Cys Phe Glu Ser His Leu Tyr Ser Ala Tyr
                85                  90                  95

Lys Asn Asp Ser Ser Ala Tyr His Leu Glu Lys Leu Asp Ile Asp Lys
            100                 105                 110

Lys Tyr Ala Ile Asn Ser Ser Phe Ser Asp Phe Tyr Leu Lys Ile Leu
        115                 120                 125

Val Ile Pro Asn Glu Tyr Lys Ser His Lys Thr Ile Tyr Cys Arg Cys
    130                 135                 140

Asp Asn Ser Lys Thr Glu Lys Asn Ile Pro Gly Gln Asp Lys Ile Leu
145                 150                 155                 160

Lys Gly Lys Leu Gly Leu Val Lys Ile Ile Leu Arg Asn Gln Tyr Asn
                165                 170                 175

Asn Ile Ile Glu Leu Glu Lys Thr Lys His Ile Ile His Asn Lys Lys
            180                 185                 190

Asp Thr Tyr Lys Tyr Asp Ile Lys Leu Lys Glu Ser Asp Ile Leu Met
        195                 200                 205

Phe Tyr Met Lys Glu Thr Ile Val Glu Ser Gly Asn Cys Glu Glu
    210                 215                 220

Ile Leu Asn Thr Lys Ile Asn Leu Leu Ser Asn Asn Val Val Leu
225                 230                 235                 240

Lys Met Pro Ser Ile Phe Ile Asn Asn Ile Asn Cys Met Leu Ser Ser
                245                 250                 255

Gln Asp Gln Asn Asn Glu Lys Tyr Asn Ile Asn Leu Lys Ala Asp Lys
            260                 265                 270

Thr Lys His Ile Asp Gly Cys Asp Phe Thr Lys Pro Lys Gly Lys Gly
        275                 280                 285
```

```
Ile Tyr Lys Asn Gly Phe Ile Ile Asn Asp Ile Pro Asn Glu Glu Glu
        290                 295                 300

Arg Ile Cys Thr Val His Leu Trp Asn Lys Lys Asn Gln Thr Ile Ala
305                 310                 315                 320

Gly Ile Lys Cys Pro Tyr Lys Leu Ile Pro Pro Tyr Cys Phe Lys His
                325                 330                 335

Val Leu Tyr Glu Lys Glu Ile Asp Ser Gln Lys Thr Tyr Lys Thr Phe
                340                 345                 350

Leu Leu Ser Asp Val Leu Asp Thr Pro Asn Ile Glu Tyr Tyr Gly Asn
            355                 360                 365

Asn Lys Glu Gly Met Tyr Met Leu Ala Leu Pro Thr Lys Pro Glu Lys
        370                 375                 380

Thr Asn Lys Ile Arg Cys Ile Cys Glu Gln Gly Gly Lys Lys Ala Val
385                 390                 395                 400

Met Glu Leu His Ile Ala Ser Thr Ser Thr Lys Tyr Ile Ser Met Phe
                405                 410                 415

Leu Ile Phe Phe Leu Ile Val Ile Phe Tyr Met
                420                 425

<210> SEQ ID NO 20
<211> LENGTH: 1282
<212> TYPE: DNA
<213> ORGANISM: Plasmodium falciparum

<400> SEQUENCE: 20
cattataaat ataatattat tctatttctt cctttgggta aaaaaaagta ttagtgatct      60
attaagctca acacaatacg tatgtgattt ttattttaat cccctgacta atgttaagcc     120
aactgtagtt gggtcatctg aaatatacga agaagttgga tgtactataa acaaccctac     180
gttgggtgac catatagtat taatatgtcc taagaaaaat aatggagatt ttagtaatat     240
agaaatagta cctactaact gttttgaatc tcatttatat tctgcttata aaaatgattc     300
cagcgcatat catttagaaa aattagatat cgataaaaag tatgcaataa attcatcgtt     360
cagtgatttc tatttaaaaa ttttagttat acctaatgaa tataaaagtc ataaaactat     420
atattgtaga tgtgataata gtaaaacgga aaaaaatatc ccaggacaag ataaaatatt     480
aaaaggaaaa ttaggattag taaaaataat tttaagaaac caatataata atataataga     540
attagaaaaa acaaaacata ttatacataa taagaaggat acatataagt atgatataaa     600
attaaaagaa agtgatatac ttatgtttta tatgaaagaa gaaactattg tagaatctgg     660
aaattgtgaa gaaatattaa atactaaaat aaatctatta tcaataataa atgtggtttt     720
aaaaatgcct tccatattta taataatat taattgtatg ctttcatctc aagatcaaaa     780
taatgaaaaa tataatataa atctaaaagc tgacaaaaca aaacatatag atgggtgtga     840
ttttacgaaa cctaaaggta aggtatata caaaaatgga ttcataataa atgatatacc     900
aaatgaagaa gaacgtatat gtactgttca tctttggaat aaaaaaaatc aaactattgc     960
aggcattaaa tgtccatata attaatacc accatattgt tttaaacatg tattatatga    1020
aaaagaaatc gattcgcaaa agacatataa aacatttcta ttaagtgatg tattagatac    1080
acctaatata gaatattatg gaaataataa ggaaggcatg tatatgttag ccttaccaac    1140
aaaaccagaa aaacaaaata aaattagatg tatttgtgaa caaggtggaa aaaagcagt    1200 aatggaatta catatcgcat ctacatctac aaaatatatt agtatgtttc ttatattttt    1260
tctgattgta attttttaca tg                                           1282
```

<210> SEQ ID NO 21
<211> LENGTH: 217
<212> TYPE: PRT
<213> ORGANISM: Plasmodium falciparum

<400> SEQUENCE: 21

```
Met Asn Lys Leu Tyr Ser Leu Phe Leu Phe Leu Phe Ile Gln Leu Ser
1               5                   10                  15
Ile Lys Tyr Asn Asn Ala Lys Val Thr Val Asp Thr Val Cys Lys Arg
            20                  25                  30
Gly Phe Leu Ile Gln Met Ser Gly His Leu Glu Cys Lys Cys Glu Asn
        35                  40                  45
Asp Leu Val Leu Val Asn Glu Glu Thr Cys Glu Glu Lys Val Leu Lys
    50                  55                  60
Cys Asp Glu Lys Thr Val Asn Lys Pro Cys Gly Asp Phe Ser Lys Cys
65                  70                  75                  80
Ile Lys Ile Asp Gly Asn Pro Val Ser Tyr Ala Cys Lys Cys Asn Leu
                85                  90                  95
Gly Tyr Asp Met Val Asn Asn Val Cys Ile Pro Asn Glu Cys Lys Asn
            100                 105                 110
Val Thr Cys Gly Asn Gly Lys Cys Ile Leu Asp Thr Ser Asn Pro Val
        115                 120                 125
Lys Thr Ala Val Cys Ser Cys Asn Ile Gly Lys Val Pro Asn Val Gln
    130                 135                 140
Asp Gln Asn Lys Cys Ser Lys Asp Gly Glu Thr Lys Cys Ser Leu Lys
145                 150                 155                 160
Cys Leu Lys Glu Asn Glu Thr Cys Lys Ala Val Asp Gly Ile Tyr Lys
                165                 170                 175
Cys Asp Cys Lys Asp Gly Phe Ile Ile Asp Asn Glu Ser Ser Ile Cys
            180                 185                 190
Thr Ala Phe Ser Ala Tyr Asn Ile Leu Asn Leu Ser Ile Met Phe Ile
        195                 200                 205
Leu Phe Ser Val Cys Phe Phe Ile Met
    210                 215
```

<210> SEQ ID NO 22
<211> LENGTH: 654
<212> TYPE: DNA
<213> ORGANISM: Plasmodium falciparum

<400> SEQUENCE: 22

```
atgaataaac tttacagttt gtttcttttc cttttcattc aacttagcat aaaatataat    60
aatgcgaaag ttaccgtgga tactgtatgc aaaagaggat ttttaattca gatgagtggt   120
catttggaat gtaaatgtga aaatgatttg gtgttagtaa atgaagaaac atgtgaagaa   180
aaagttctga atgtgacgaa aaagactgta aataaccat gtggagattt ttccaaatgt   240
attaaaatag atggaaatcc cgtttcatac gcttgtaaat gtaatcttgg atatgatatg   300
gtaaataatg tttgtatacc aaatgaatgt aagaatgtaa cttgtggtaa cggtaaatgt   360
atattagata caagcaatcc tgttaaaact gcagtttgct catgtaatat aggcaaagtt   420
cccaatgtac aagatcaaaa taaatgttca aaagatggag aaaccaaatg ctcattaaaa   480
tgcttaaaag aaaatgaaac ctgtaaagct gttgatggaa tttataaatg tgattgtaaa   540
gatggattta atagataa tgaaagctct atatgtactg cttttcagc atataatatt   600
```
ttaaatctaa gcattatgtt tatactattt tcagtatgct tttttataat gtaa    654

<210> SEQ ID NO 23
<211> LENGTH: 354
<212> TYPE: PRT
<213> ORGANISM: Plasmodium falciparum

<400> SEQUENCE: 23

```
Met Lys Ser Phe Ile Asn Ile Thr Leu Ser Leu Phe Leu Leu His Leu
1               5                   10                  15

Tyr Ile Tyr Ile Asn Asn Val Ala Ser Lys Glu Ile Val Lys Lys Tyr
            20                  25                  30

Asn Leu Asn Leu Arg Asn Ala Ile Leu Asn Asn Asn Ser Gln Ile Glu
        35                  40                  45

Asn Glu Glu Asn Val Asn Thr Thr Ile Thr Gly Asn Asp Phe Ser Gly
    50                  55                  60

Gly Glu Phe Leu Trp Pro Gly Tyr Thr Glu Glu Leu Lys Ala Lys Lys
65                  70                  75                  80

Ala Ser Glu Asp Ala Glu Lys Ala Ala Asn Asp Ala Glu Asn Ala Ser
                85                  90                  95

Lys Glu Ala Glu Glu Ala Ala Lys Glu Ala Val Asn Leu Lys Glu Ser
            100                 105                 110

Asp Lys Ser Tyr Thr Lys Ala Lys Glu Ala Cys Thr Ala Ala Ser Lys
        115                 120                 125

Ala Lys Lys Ala Val Glu Thr Ala Leu Lys Ala Lys Asp Asp Ala Glu
    130                 135                 140

Lys Ser Ser Lys Ala Asp Ser Ile Ser Thr Lys Thr Lys Glu Tyr Ala
145                 150                 155                 160

Glu Lys Ala Lys Asn Ala Tyr Glu Lys Ala Lys Asn Ala Tyr Gln Lys
                165                 170                 175

Ala Asn Gln Ala Val Leu Lys Ala Lys Glu Ala Ser Ser Tyr Asp Tyr
            180                 185                 190

Ile Leu Gly Trp Glu Phe Gly Gly Gly Val Pro Glu His Lys Lys Glu
        195                 200                 205

Glu Asn Met Leu Ser His Leu Tyr Val Ser Ser Lys Asp Lys Glu Asn
    210                 215                 220

Ile Ser Lys Glu Asn Asp Asp Val Leu Asp Glu Lys Glu Glu Glu Ala
225                 230                 235                 240

Glu Glu Thr Glu Glu Glu Leu Glu Glu Lys Asn Glu Glu Glu Glu Thr
                245                 250                 255

Glu Ser Glu Ile Ser Glu Asp Glu Glu Glu Glu Glu Glu Glu Glu Glu
            260                 265                 270

Lys Glu Glu Asn Asp Lys Lys Glu Gln Glu Lys Glu Gln Ser
        275                 280                 285

Asn Glu Asn Asn Asp Gln Lys Lys Asp Met Glu Ala Gln Asn Leu Ile
    290                 295                 300

Ser Lys Asn Gln Asn Asn Glu Lys Asn Val Lys Glu Ala Ala Glu
305                 310                 315                 320

Ser Ile Met Lys Thr Leu Ala Gly Leu Ile Lys Gly Asn Asn Gln Ile
                325                 330                 335

Asp Ser Thr Leu Lys Asp Leu Val Glu Glu Leu Ser Lys Tyr Phe Lys
            340                 345                 350

Asn His
```

-continued

```
<210> SEQ ID NO 24
<211> LENGTH: 1065
<212> TYPE: DNA
<213> ORGANISM: Plasmodium falciparum

<400> SEQUENCE: 24
atgaaaagtt ttataaatat tactctttca ttattttgt tacatttata tatttatata      60
aataatgttg ctagtaaaga aattgtaaaa aaatataatc ttaacttaag aaatgcaata     120
ttgaataata attctcaaat agaaaatgaa gaaaatgtaa atactacaat tactggtaat     180
gattttagtg gtggagaatt tttgtggcct ggttatacgg aagaattaaa agctaaaaaa     240
gcttccgaag atgctgaaaa agctgctaat gatgctgaaa atgcttcaaa agaggcagaa     300
gaagctgcta agaagcagt aaatttaaag gaatctgata atcttatac aaaagcaaaa      360
gaagcatgta cagctgcttc aaaggcaaag aaagctgttg aaactgcttt aaaggcaaaa     420
gatgatgctg aaaaatcttc aaaagctgat agtatttcta caaaaacaaa agaatatgct     480
gaaaaagcaa aaaatgctta tgaaaaggca aaaaatgctt atcaaaaagc aaaccaagct     540
gttttaaaag caaagaagc ttctagttat gattatattt taggttggga atttggagga      600
ggcgttccag aacacaaaaa agaagaaaat atgttatcac atttatatgt ttcttcaaag     660
gataaggaaa atatatctaa ggaaaatgat gatgtattag atgagaagga agaagaggca     720
gaagaaacag aagaagaaga acttgaagaa aaaaatgaag aagaaacaga atcagaaata     780
agtgaagatg aagaagaaga agaagaagaa gaagaaaagg aagaagaaaa tgacaaaaaa     840
aaagaacaag aaaagaaca agtaatgaa aataatgatc aaaaaaaaga tatggaagca      900
cagaatttaa tttctaaaaa ccagaataat aatgagaaaa acgtaaaaga agctgctgaa     960
agcatcatga aactttagc tggtttaatc aagggaaata atcaaataga ttctacctta    1020
aaagatttag tagaagaatt atccaaatat tttaaaaatc attaa                    1065

<210> SEQ ID NO 25
<211> LENGTH: 630
<212> TYPE: PRT
<213> ORGANISM: Plasmodium falciparum

<400> SEQUENCE: 25

Ala Glu Arg Ser Thr Ser Glu Asn Arg Asn Lys Arg Ile Gly Gly Pro
1               5                   10                  15

Lys Leu Arg Gly Asn Val Thr Ser Asn Ile Lys Phe Pro Ser Asp Asn
                20                  25                  30

Lys Gly Lys Ile Ile Arg Gly Ser Asn Asp Lys Leu Asn Lys Asn Ser
            35                  40                  45

Glu Asp Val Leu Glu Gln Ser Glu Lys Ser Leu Val Ser Glu Asn Val
        50                  55                  60

Pro Ser Gly Leu Asp Ile Asp Ile Pro Lys Glu Ser Ile Phe Ile
65                  70                  75                  80

Gln Glu Asp Gln Glu Gly Gln Thr His Ser Glu Leu Asn Pro Glu Thr
                85                  90                  95

Ser Glu His Ser Lys Asp Leu Asn Asn Asn Gly Ser Lys Asn Glu Ser
            100                 105                 110

Ser Asp Ile Ile Ser Glu Asn Asn Lys Ser Asn Lys Val Gln Asn His
        115                 120                 125

Phe Glu Ser Leu Ser Asp Leu Glu Leu Leu Glu Asn Ser Ser Gln Asp
    130                 135                 140

Asn Leu Asp Lys Asp Thr Ile Ser Thr Glu Pro Phe Pro Asn Gln Lys
```

```
            145                 150                 155                 160
        His Lys Asp Leu Gln Gln Asp Leu Asn Asp Glu Pro Leu Glu Pro Phe
                            165                 170                 175
        Pro Thr Gln Ile His Lys Asp Tyr Lys Glu Lys Asn Leu Ile Asn Glu
                            180                 185                 190
        Glu Asp Ser Glu Pro Phe Pro Arg Gln Lys His Lys Lys Val Asp Asn
                            195                 200                 205
        His Asn Glu Glu Lys Asn Val Phe His Glu Asn Gly Ser Ala Asn Gly
                    210                 215                 220
        Asn Gln Gly Ser Leu Lys Leu Lys Ser Phe Asp Glu His Leu Lys Asp
        225                 230                 235                 240
        Glu Lys Ile Glu Asn Glu Pro Leu Val His Glu Asn Leu Ser Ile Pro
                            245                 250                 255
        Asn Asp Pro Ile Glu Gln Ile Leu Asn Gln Pro Glu Gln Glu Thr Asn
                            260                 265                 270
        Ile Gln Glu Gln Leu Tyr Asn Glu Lys Gln Asn Val Glu Glu Lys Gln
                            275                 280                 285
        Asn Ser Gln Ile Pro Ser Leu Asp Leu Lys Glu Pro Thr Asn Glu Asp
                    290                 295                 300
        Ile Leu Pro Asn His Asn Pro Leu Glu Asn Ile Lys Gln Ser Glu Ser
        305                 310                 315                 320
        Glu Ile Asn His Val Gln Asp His Ala Leu Pro Lys Gly Asn Ile Ile
                            325                 330                 335
        Asp Lys Leu Asp Asn Gln Lys Glu His Ile Asp Gln Ser Gln His Asn
                            340                 345                 350
        Ile Asn Val Leu Gln Glu Asn Asn Ile Asn Asn His Gln Leu Glu Pro
                    355                 360                 365
        Gln Glu Lys Pro Asn Ile Glu Ser Phe Glu Pro Lys Asn Ile Asp Ser
                    370                 375                 380
        Glu Ile Ile Leu Pro Glu Asn Val Glu Thr Glu Ile Ile Asp Asp
        385                 390                 395                 400
        Val Pro Ser Pro Lys His Ser Asn His Glu Thr Phe Glu Gly Glu Thr
                            405                 410                 415
        Ser Glu Ser Glu His Glu Glu Ala Val Ser Glu Lys Asn Ala His Glu
                            420                 425                 430
        Thr Val Glu His Glu Glu Thr Val Ser Gln Glu Ser Asn Pro Glu Lys
                            435                 440                 445
        Ala Asp Asn Asp Gly Asn Val Ser Gln Asn Ser Asn Asn Glu Leu Asn
        450                 455                 460
        Glu Asn Glu Phe Val Glu Ser Glu Lys Ser Glu His Glu Ala Arg Ser
        465                 470                 475                 480
        Lys Pro Lys Tyr Glu Lys Lys Val Ile His Gly Cys Asn Phe Ser Ser
                            485                 490                 495
        Asn Val Ser Ser Lys His Thr Phe Thr Asp Ser Leu Asp Ile Ser Leu
                    500                 505                 510
        Val Asp Asp Ser Ala His Ile Ser Cys Asn Val His Leu Ser Glu Pro
                    515                 520                 525
        Lys Tyr Asn His Leu Val Gly Leu Asn Cys Pro Gly Asp Ile Ile Pro
                    530                 535                 540
        Asp Cys Phe Phe Gln Val Tyr Gln Pro Glu Ser Glu Glu Leu Glu Pro
        545                 550                 555                 560
        Ser Asn Ile Val Tyr Leu Asp Ser Gln Ile Asn Ile Gly Asp Ile Glu
                    565                 570                 575
```

```
Tyr Tyr Glu Asp Ala Glu Gly Asp Asp Lys Ile Lys Leu Phe Gly Ile
            580                 585                 590

Val Gly Ser Ile Pro Lys Thr Thr Ser Phe Thr Cys Ile Cys Lys Lys
        595                 600                 605

Asp Lys Lys Ser Ala Tyr Met Thr Val Thr Ile Asp Ser Ala Arg Ser
    610                 615                 620

His His His His His His
625                 630

<210> SEQ ID NO 26
<211> LENGTH: 1977
<212> TYPE: DNA
<213> ORGANISM: Plasmodium falciparum

<400> SEQUENCE: 26
atgaaattta ataaaaaaag agttgcaata gccacgttta ttgctttgat atttgtaagt     60
ttttttacaa tatcatcaat ccaagatgct caagcagccg aaagatccac aagtgagaat    120
agaaataaac gaatcggggg tcctaaatta aggggtaatg ttacaagtaa tataaagttc    180
ccatcagata caaaggtaa aattataaga ggttcgaatg ataaacttaa taaaaactct     240
gaagatgttt tagaacaaag cgaaaaatcg cttgtttcag aaaatgttcc tagtggatta    300
gatatagatg atatccctaa agaatctatt tttattcaag aagatcaaga aggtcaaact    360
cattctgaat taaatcctga acatcagaaa catagtaaag atttaaataa taatggttca    420
aaaaatgaat ctagtgatat tatttcgaaa aataataaat caaataaagt acaaaatcat    480
tttgaatcat tatcagattt agaattactt gaaaattcct cacaagataa tttagacaaa    540
gatacaattt caacagaacc ttttcctaat caaaaacata agacttaca acaagattta    600 aatgatgaac ctttagaacc cttccctaca caaatacata agattataa agaaaaaat     660 ttaataaatg aagaagattc agaaccattt cccagacaaa agcataaaaa ggtagacaat    720
cataatgaag aaaaaaacgt atttcatgaa atggttctg caaatggtaa tcaaggaagt    780
ttgaaactta atcattcga tgaacattta aaagatgaaa aatagaaaa tgaaccactt    840 gttcatgaaa atttatccat accaaatgat ccaatagaac aaatattaaa tcaacctgaa    900
caagaaacaa atatccagga caattgtat aatgaaaaac aaaatgttga agaaaaacaa    960
aattctcaaa taccttcgtt agatttaaaa gaaccaacaa tgaagatat tttaccaaat   1020 cataatccat tagaaaatat aaaacaaagt gaatcagaaa taaatcatgt acaagatcat   1080
gcgctaccaa aagagaatat aatagacaaa cttgataatc aaaaagaaca catcgatcaa   1140
tcacaacata atataaatgt attacaagaa aataacataa acaatcacca attagaacct   1200
caagagaaac ctaatattga atcgtttgaa cctaaaaata tagattcaga aattattctt   1260
cctgaaaatg ttgaaacaga gaaataata gatgatgtgc cttcccctaa acattctaac   1320
catgaaacat ttgaagaaga aacaagtgaa tctgaacatg aagaagccgt atctgaaaaa   1380
aatgcccacg aaactgtcga acatgaagaa actgtgtctc aagaaagcaa tcctgaaaaa   1440
gctgataatg atggaaatgt atctcaaaac agcaacaacg aattaaatga aaatgaattc   1500
gttgaatcgg aaaaaagcga gcatgaagca agatccgaaa aaaagtcat acacggatgt   1560 aacttctctt caaatgttag ttctaaacat acttttacag atagtttaga tatttcttta   1620
gttgatgata gtgcacatat ttcatgtaac gtacatttgt ctgaaccaaa atataatcat   1680
ttggtaggtt taaattgtcc tggtgatatt ataccagatt gctttttca agtatatcaa   1740
```

-continued

```
cctgaatcag aagaacttga accatccaac attgtttatt tagattcaca aataaatata    1800
ggagatattg aatattatga agatgctgaa ggagatgata aaattaaatt atttggtata    1860
gttggaagta taccaaaaac gacatctttt acttgtatat gtaagaagga taaaaaagt    1920 gcttatatga cagttactat agattcagca agatctcatc accatcatca ccattag      1977
```

```
<210> SEQ ID NO 27
<211> LENGTH: 727
<212> TYPE: PRT
<213> ORGANISM: Plasmodium falciparum

<400> SEQUENCE: 27
```

| | | | | | | | | | | | | | | |
|---|---|---|---|---|---|---|---|---|---|---|---|---|---|---|
| Ala | Glu | Arg | Ser | Thr | Ser | Glu | Asn | Arg | Asn | Lys | Arg | Ile | Gly | Gly | Pro |
| 1 | | | | 5 | | | | | 10 | | | | | 15 | |
| Lys | Leu | Arg | Gly | Asn | Val | Thr | Ser | Asn | Ile | Lys | Phe | Pro | Ser | Asp | Asn |
| | | | 20 | | | | | 25 | | | | | 30 | | |
| Lys | Gly | Lys | Ile | Ile | Arg | Gly | Ser | Asn | Asp | Lys | Leu | Asn | Lys | Asn | Ser |
| | | 35 | | | | | 40 | | | | | 45 | | | |
| Glu | Asp | Val | Leu | Glu | Gln | Ser | Glu | Lys | Ser | Leu | Val | Ser | Glu | Asn | Val |
| | 50 | | | | | 55 | | | | | 60 | | | | |
| Pro | Ser | Gly | Leu | Asp | Ile | Asp | Ile | Pro | Lys | Glu | Ser | Ile | Phe | Ile |
| 65 | | | | | 70 | | | | | 75 | | | | | 80 |
| Gln | Glu | Asp | Gln | Glu | Gly | Gln | Thr | His | Ser | Glu | Leu | Asn | Pro | Glu | Thr |
| | | | | 85 | | | | | 90 | | | | | 95 | |
| Ser | Glu | His | Ser | Lys | Asp | Leu | Asn | Asn | Asn | Gly | Ser | Lys | Asn | Glu | Ser |
| | | | 100 | | | | | 105 | | | | | 110 | | |
| Ser | Asp | Ile | Ile | Ser | Glu | Asn | Asn | Lys | Ser | Asn | Lys | Val | Gln | Asn | His |
| | | 115 | | | | | 120 | | | | | 125 | | | |
| Phe | Glu | Ser | Leu | Ser | Asp | Leu | Glu | Leu | Leu | Glu | Asn | Ser | Ser | Gln | Asp |
| | 130 | | | | | 135 | | | | | 140 | | | | |
| Asn | Leu | Asp | Lys | Asp | Thr | Ile | Ser | Thr | Glu | Pro | Phe | Pro | Asn | Gln | Lys |
| 145 | | | | | 150 | | | | | 155 | | | | | 160 |
| His | Lys | Asp | Leu | Gln | Gln | Asp | Leu | Asn | Asp | Glu | Pro | Leu | Glu | Pro | Phe |
| | | | | 165 | | | | | 170 | | | | | 175 | |
| Pro | Thr | Gln | Ile | His | Lys | Asp | Tyr | Lys | Glu | Lys | Asn | Leu | Ile | Asn | Glu |
| | | | 180 | | | | | 185 | | | | | 190 | | |
| Glu | Asp | Ser | Glu | Pro | Phe | Pro | Arg | Gln | Lys | His | Lys | Lys | Val | Asp | Asn |
| | | 195 | | | | | 200 | | | | | 205 | | | |
| His | Asn | Glu | Glu | Lys | Asn | Val | Phe | His | Glu | Asn | Gly | Ser | Ala | Asn | Gly |
| | 210 | | | | | 215 | | | | | 220 | | | | |
| Asn | Gln | Gly | Ser | Leu | Lys | Leu | Lys | Ser | Phe | Asp | Glu | His | Leu | Lys | Asp |
| 225 | | | | | 230 | | | | | 235 | | | | | 240 |
| Glu | Lys | Ile | Glu | Asn | Glu | Pro | Leu | Val | His | Glu | Asn | Leu | Ser | Ile | Pro |
| | | | | 245 | | | | | 250 | | | | | 255 | |
| Asn | Asp | Pro | Ile | Glu | Gln | Ile | Leu | Asn | Gln | Pro | Glu | Gln | Glu | Thr | Asn |
| | | | 260 | | | | | 265 | | | | | 270 | | |
| Ile | Gln | Glu | Gln | Leu | Tyr | Asn | Glu | Lys | Gln | Asn | Val | Glu | Glu | Lys | Gln |
| | | 275 | | | | | 280 | | | | | 285 | | | |
| Asn | Ser | Gln | Ile | Pro | Ser | Leu | Asp | Leu | Lys | Glu | Pro | Thr | Asn | Glu | Asp |
| | 290 | | | | | 295 | | | | | 300 | | | | |
| Ile | Leu | Pro | Asn | His | Asn | Pro | Leu | Glu | Asn | Ile | Lys | Gln | Ser | Glu | Ser |
| 305 | | | | | 310 | | | | | 315 | | | | | 320 |
| Glu | Ile | Asn | His | Val | Gln | Asp | His | Ala | Leu | Pro | Lys | Glu | Asn | Ile | Ile |
| | | | | 325 | | | | | 330 | | | | | 335 | |

```
Asp Lys Leu Asp Asn Gln Lys Glu His Ile Asp Gln Ser Gln His Asn
            340                 345                 350

Ile Asn Val Leu Gln Glu Asn Ile Asn Asn His Gln Leu Glu Pro
            355                 360                 365

Gln Glu Lys Pro Asn Ile Glu Ser Phe Glu Pro Lys Asn Ile Asp Ser
            370                 375                 380

Glu Ile Ile Leu Pro Glu Asn Val Glu Thr Glu Ile Ile Asp Asp
385                 390                 395                 400

Val Pro Ser Pro Lys His Ser Asn His Glu Thr Phe Glu Glu Thr
            405                 410                 415

Ser Glu Ser Glu His Glu Glu Ala Val Ser Glu Lys Asn Ala His Glu
            420                 425                 430

Thr Val Glu His Glu Glu Thr Val Ser Gln Glu Ser Asn Pro Glu Lys
            435                 440                 445

Ala Asp Asn Asp Gly Asn Val Ser Gln Asn Ser Asn Asn Glu Leu Asn
            450                 455                 460

Glu Asn Glu Phe Val Glu Ser Glu Lys Ser Glu His Glu Ala Arg Ser
465                 470                 475                 480

Lys Thr Lys Glu Tyr Ala Glu Lys Ala Lys Asn Ala Tyr Glu Lys Ala
            485                 490                 495

Lys Asn Ala Tyr Gln Lys Ala Asn Gln Ala Val Leu Lys Ala Lys Glu
            500                 505                 510

Ala Ser Ser Tyr Asp Tyr Ile Leu Gly Trp Glu Phe Gly Gly Gly Val
            515                 520                 525

Pro Glu His Lys Lys Glu Glu Asn Met Leu Ser His Leu Tyr Val Ser
            530                 535                 540

Ser Lys Asp Lys Glu Asn Ile Ser Lys Glu Asn Asp Val Leu Asp
545                 550                 555                 560

Glu Lys Glu Glu Glu Ala Glu Thr Glu Glu Glu Leu Glu Arg
            565                 570                 575

Ser Lys Pro Lys Tyr Glu Lys Lys Val Ile His Gly Cys Asn Phe Ser
            580                 585                 590

Ser Asn Val Ser Ser Lys His Thr Phe Thr Asp Ser Leu Asp Ile Ser
            595                 600                 605

Leu Val Asp Asp Ser Ala His Ile Ser Cys Asn Val His Leu Ser Glu
            610                 615                 620

Pro Lys Tyr Asn His Leu Val Gly Leu Asn Cys Pro Gly Asp Ile Ile
625                 630                 635                 640

Pro Asp Cys Phe Phe Gln Val Tyr Gln Pro Glu Ser Glu Glu Leu Glu
            645                 650                 655

Pro Ser Asn Ile Val Tyr Leu Asp Ser Gln Ile Asn Ile Gly Asp Ile
            660                 665                 670

Glu Tyr Tyr Glu Asp Ala Glu Gly Asp Asp Lys Ile Lys Leu Phe Gly
            675                 680                 685

Ile Val Gly Ser Ile Pro Lys Thr Thr Ser Phe Thr Cys Ile Cys Lys
            690                 695                 700

Lys Asp Lys Lys Ser Ala Tyr Met Thr Val Thr Ile Asp Ser Ala Arg
705                 710                 715                 720

Ser His His His His His His
            725
```

<210> SEQ ID NO 28
<211> LENGTH: 2268
<212> TYPE: DNA
<213> ORGANISM: Plasmodium falciparum

<400> SEQUENCE: 28

| | |
|---|---|
| atgaaattta ataaaaaaag agttgcaata gccacgttta ttgctttgat atttgtaagt | 60 |
| tttttttacaa tatcatcaat ccaagatgct caagcagccg aaagatccac aagtgagaat | 120 |
| agaaataaac gaatcggggg tcctaaatta aggggtaatg ttacaagtaa tataaagttc | 180 |
| ccatcagata acaaaggtaa aattataaga ggttcgaatg ataaacttaa taaaaactct | 240 |
| gaagatgttt tagaacaaag cgaaaaatcg cttgtttcag aaaatgttcc tagtggatta | 300 |
| gatatagatg atatccctaa agaatctatt tttattcaag aagatcaaga aggtcaaact | 360 |
| cattctgaat taaatcctga aacatcagaa catagtaaag atttaaataa taatggttca | 420 |
| aaaaatgaat ctagtgatat tatttcagaa aataataaat caaataaagt acaaaatcat | 480 |
| tttgaatcat tatcagattt agaattactt gaaaattcct cacaagataa tttagacaaa | 540 |
| gatacaattt caacagaacc ttttcctaat caaaaacata aagacttaca acaagattta | 600 |
| aatgatgaac ctttagaacc cttttcctaca caaatacata aagattataa agaaaaaaat | 660 |
| ttaataaatg aagaagattc agaaccattt cccagacaaa agcataaaaa ggtagacaat | 720 |
| cataatgaag aaaaaaacgt atttcatgaa aatggttctg caaatggtaa tcaaggaagt | 780 |
| ttgaaactta aatcattcga tgaacattta aaagatgaaa aatagaaaa tgaaccactt | 840 |
| gttcatgaaa atttatccat accaaatgat ccaatagaac aaatattaaa tcaacctgaa | 900 |
| caagaaacaa atatccagga caattgtat aatgaaaaac aaaatgttga agaaaaacaa | 960 |
| aattctcaaa taccttcgtt agatttaaaa gaaccaacaa atgaagatat tttaccaaat | 1020 |
| cataatccat tagaaaatat aaaacaaagt gaatcagaaa taaatcatgt acaagatcat | 1080 |
| gcgctaccaa aagagaatat aatagacaaa cttgataatc aaaaagaaca catcgatcaa | 1140 |
| tcacaacata atataaatgt attacaagaa aataacataa acaatcacca attagaacct | 1200 |
| caagagaaac ctaatattga atcgtttgaa cctaaaaata tagattcaga aattattctt | 1260 |
| cctgaaaatg ttgaaacaga agaaataata gatgatgtgc cttcccctaa acattctaac | 1320 |
| catgaaacat ttgaagaaga aacaagtgaa tctgaacatg aagaagccgt atctgaaaaa | 1380 |
| aatgcccacg aaactgtcga acatgaagaa actgtgtctc aagaaagcaa tcctgaaaaa | 1440 |
| gctgataatg atgaaatgt atctcaaaac agcaacaacg aattaaatga aaatgaattc | 1500 |
| gttgaatcgg aaaaaagcga gcatgaagca agatccaaaa caaaagaata tgctgaaaaa | 1560 |
| gcaaaaaatg cttatgaaaa ggcaaaaaat gcttatcaaa aagcaaacca agctgtttta | 1620 |
| aaagcaaaag aagcttctag ttatgattat attttaggtt gggaatttgg aggaggcgtt | 1680 |
| ccagaacaca aaaagaaga aaatatgtta tcacatttat atgtttcttc aaaggataag | 1740 |
| gaaaatatat ctaaggaaaa tgatgatgta ttagatgaga aggaagaaga ggcagaagaa | 1800 |
| acagaagaag aagaacttga agatccgaa aaaaagtca tacacggatg taacttctct | 1860 |
| tcaaatgtta gttctaaaca tacttttaca gatagtttag atatttcttt agttgatgat | 1920 |
| agtgcacata tttcatgtaa cgtacatttg tctgaaccaa aatataatca tttggtaggt | 1980 |
| ttaaattgtc ctggtgatat tataccagat tgctttttc aagtatatca acctgaatca | 2040 |
| gaagaacttg aaccatccaa cattgtttat ttagattcac aaataaatat aggagatatt | 2100 |

```
gaatattatg aagatgctga aggagatgat aaaattaaat tatttggtat agttggaagt    2160
ataccaaaaa cgacatcttt tacttgtata tgtaagaagg ataaaaaaag tgcttatatg    2220
acagttacta tagattcagc aagatctcat caccatcatc accattag                2268
```

PRODUCTION OF A CYSTEINE RICH PROTEIN

CROSS-REFERENCE TO RELATED APPLICATIONS

This application is a national stage of International Patent Application No. PCT/DK2012/000108, filed Oct. 3, 2013, which claims the benefit of the priority of Danish Patent Application No. PA 2011 00765, tiled Oct. 4, 2011, all of which are incorporated by reference herein.

FIELD OF INVENTION

Large scale production method of a cysteine-rich protein (CYRP) in a lactic acid bacterium by enhancing the secretion by fusion to a glutamate rich protein, stabilizing the monomeric protein, and enhancing the protein folding is described. A cysteine rich antigen based transmission-blocking vaccine or immunogenic composition against malaria comprising fusion proteins derived from *Plasmodium falciparum* Glutamate-rich protein (GLURP) genetically coupled to at least one other *Plasmodium falciparum* CYRP, e.g. Pfs48/45 and the DNA encoding this fusion protein is disclosed.

BACKGROUND

Malaria is affecting 40% of the world's population with an estimated 1.5-2.7 million deaths annually (32). This represents a tremendous human suffering and a burden that prevents the development of the affected endemic communities. Malaria is now almost confined to the poorest tropical areas of Africa, Asia and Latin America, but transmission is being reintroduced to areas where it had previously been eradicated. Malaria is one of the world's greatest public health problems.

The increasing emerging of insecticide resistant vectors and drug resistant parasites calls for investment in new and better control tools. Malaria vaccines hold the potential to dramatically alleviate the burden of malaria. However, our understanding of the mechanisms underlying protective immunity is incomplete hence specific markers of protection still needs to be defined.

An effective malaria vaccine will require the induction of appropriate humoral and cellular immune responses, against several key parasite antigens expressed during the various stages of the parasite life cycle. Each stage in the life cycle provides an opportunity for a vaccine.

Presently, three main lines of malaria vaccine research dominate: (i) induction of immunity against pre-erythrocytic antigens, a strategy rooted in first experiments with UV-inactivated *P. gallinaceum* sporozoites (25), (ii) identification of antigens that induce antibodies with specificities similar to those of immunoglobulin preparations of semi-immune adults with a therapeutic effect in malaria patients (5), and (iii) induction of transmission-blocking (TB) antibodies against parasite antigens that are expressed in the infected mosquito (11). The first two strategies rely on malaria antigens that induce a protective immune response, and the third strategy on malaria antigens that are essential for sexual development of the parasites in the infected mosquito.

The objective of a transmission-blocking malaria vaccine (TBMV) is to prevent an individual from becoming infected with *Plasmodium* parasites by mosquito bites of the *Anopheles* vector. As a result, the spread of malaria in the population is expected to decrease with subsequent reduction of the disease. TBMVs are based on sexual- or sporogonic-specific antigens and designed to arrest the development of sporogonic stages inside the mosquito. The specific antibodies generated in the human host are passively ingested together with parasites when mosquitoes take a blood meal and will bind to the parasites thereby preventing progression of their sporogonic development. Once inside the mosquito midgut, gametocytes rapidly emerge from the intracellular red blood cell environment to prepare for fertilization and are directly exposed to hostile immune components of the ingested blood. The sporogonic cycle is biologically the most vulnerable part of the lifecycle because parasite numbers are very low which makes this an attractive target for interventions.

The *Plasmodium falciparum* Pfs48/45 is a sexual stage-specific protein expressed by gametocytes (2, 12) and present on the surface of the sporogonic (macrogametes) stages of the malaria parasites. Pfs48/45 plays a key role in male gamete fertility and zygote formation e.g. parasite fertilization (29) and antibodies which target conformational epitopes of Pfs48/45 prevent fertilization (22, 31). Specific antibodies against Pfs48/45 are present in human sera from endemic areas (23) and correlate with TB activity (4, 23-24, 27).

Five distinct B-cell epitopes (epitope II is subdivided into IIa and IIb) have been defined based on binding studies with a panel of Pfs48/45 specific monoclonal antibodies (24) (FIG. 1). Epitopes I-III in the C-terminal domain of the protein are conformational and epitope IV is linear. For epitope V in the N-terminal domain, both linear- and conformation-dependent monoclonal antibodies have been described (24). Monoclonal antibodies to epitope I and V block transmission effectively in the membrane feeding assay but monoclonal antibodies of epitope IIb and epitope III were ineffective on their own but able to reduce transmission when used in combination (3, 21, 30).

Pfs48/45 has been produced on recombinant form in different expression systems; however, the major challenges with recombinant Pfs48/45 are that it is very difficult to produce correctly folded protein. Proper folding of many CYRPs, including Pfs48/45, depends on correct formation of disulphide bridges. In eukaryotes the oxidizing environment of the endoplasmic reticulum (ER) provides a milieu for disulphide bonds formation. Prokaryotic organisms such as *Escherichia coli* and *Lactococcus lactis* lack the sophisticated ER machinery of disulphide bond formation. In *Escherichia coli* correct disulphide bonds are formed in the periplasmic space catalyzed by a set of periplasmic oxidoreductases. Accordingly, the C-terminal Pfs48/45 fragment (10C) (FIG. 1) was produced as a correctly folded protein in the periplasm of *Escherichia coli* when genetically fused to the maltose binding protein (MBP) and co-expressed with four periplasmic folding catalysts, (17). Levels of up to 1 mg/L pure correctly folded material was reported. Such expression levels are insufficient for further up-scaling and GMP production.

It is therefore, desirable to develop a large scale production method for a vaccine based on a recombinant protein, which include Pfs48/45 or other cysteine-rich antigens from *P. falciparum* such as the Pfs25, Pfs47, Pfs230, EBA175 and Var2CSA antigens.

SUMMARY OF THE INVENTION

A method of producing a cysteine-rich protein (CYRP) on a large scale is disclosed. The CYRP is produced in a lactic acid bacteria system where the secretion of the protein is enhanced by fusing to a glutamate rich protein. The production is further optimized by stabilising the monomeric protein formation and the folding of the protein by modifying the redox conditions of the medium and the buffer solution during the down-stream processing. A transmission-blocking vaccine or immunogenic composition against malaria, which has an improved vaccine-induced antibody response, is produced in this way. The vaccine comprises a fusion protein derived from *Plasmodium falciparum* glutamate-rich protein (GLURP) or part of this genetically coupled to at least one other *Plasmodium falciparum* derived CYRP, e.g. Pfs48/45, Pfs25, Pfs47, Pfs230, EBA175 and Var2CSA or the corresponding nucleotide sequence coding said fusion protein.

DETAILED DISCLOSURE OF THE INVENTION

The present invention discloses a method for large scale production of a cysteine-rich protein (CYRP) where the CYRP is fused to a glutamate rich protein (GLURP, SEQ ID NO 1) or part of this and the fusion protein is produced in a lactic acid bacteria. The preferred lactic acid bacterium for the production is *Lactococcus lactis*.

The production is optimized by stabilizing the formation of monomeric fusion protein and enhancing the folding of the protein by modifying the redox conditions of the medium and the down-stream processing buffer.

Preferably the medium is modified by adding reduced form of a sulfhydryl containing compound such as L-cysteine or DTT or glutathione or TCEP or cysteamine (preferably L-cysteine) to the medium to a concentration of about 5-20 mM preferably about 10 mM.

The preferable method to enhance the folding of the protein is by addition of reduced and oxidized form of a sulfhydryl containing compound such as L-cysteine or DTT or glutathione or TCEP or cysteamine (preferably L-cysteine) to the washing buffer during the down-stream processing. The concentration of the reduced form is 1-10 M preferably about 4 mM and the concentration of the oxidized form is 0, 1-5 mM preferably about 0.4 mM A preferred CYRP originates from *Plasmodium falciparum* where the cysteine rich protein is chosen from the group of Pfs48/45 (SEQ ID NO 3), Pfs25 (SEQ ID NO 21), Pfs230 (SEQ ID NO 17), Pfs47 (SEQ ID NO 19), EBA175 (SEQ ID NO 13), Var2CSA (SEQ ID NO 15) or members of the PfEMP1, RIFIN, STEVOR protein families or a homologue hereof.

The present invention also discloses an antigen based transmission-blocking vaccine or immunogenic composition against malaria comprising a fusion protein derived from *Plasmodium falciparum* glutamate-rich protein (GLURP) or part of GLURP genetically coupled to at least one other *Plasmodium falciparum* derived CYRP or homologues hereof.

A preferred embodiment of the invention is an immunogenic composition or a vaccine where the protein genetically coupled to GLURP-R0 is derived from Pfs48/45 from *Plasmodium falciparum* with a C-terminal hexahistidine sequence, said fusion protein preferably having the following amino acid sequence R0-10C-6H:

(SEQ ID NO. 5)
AERSTSENRNKRIGGPKLRGNVTSNIKFPSDNKGKIIRGSNDKLNKNSE

DVLEQSEKSLVSENVPSGLDIDDIPKESIFIQEDQEGQTHSELNPETSE

HSKDLNNNGSKNESSDIISENNKSNKVQNHFESLSDLELLENSSQDNLD

KDTISTEPFPNQKHKDLQQDLNDEPLEPFPTQIHKDYKEKNLINEEDSE

PFPRQKHKKVDNHNEEKNVFHENGSANGNQGSLKLKSFDEHLKDEKIEN

EPLVHENLSIPNDPIEQILNQPEQETNIQEQLYNEKQNVEEKQNSQIPS

LDLKEPTNEDILPNHNPLENIKQSESEINHVQDHALPKENIIDKLDNQK

EHIDQSQHNINVLQENNINNHQLEPQEKPNIESFEPKNIDSEIILPENV

ETEEIIDDVPSPKHSNHETFEEETSESEHEEAVSEKNAHETVEHEETVS

QESNPEKADNDGNVSQNSNNELNENEFVESEKSEHEADNTEKVISSIEG

RSAMVHVRVLKYPHNILFTNLTNDLFTYLPKTYNESNFVSNVLEVELND

GELFVLACELINKKCFQEGKEKALYKSNKIIYHKNLTIFKAPFYVTSKD

VNTECTCKFKNNNYKIVLKPKYEKKVIHGCNFSSNVSSKHTFTDSLDIS

LVDDSAHISCNVHLSEPKYNHLVGLNCPGDIIPDCFFQVYQPESEELEP

SNIVYLDSQINIGDIEYYEDAEGDDKIKLFGIVGSIPKTTSFTCICKKD

KKSAYMTVTIDSAHHHHHH

The major epitope for transmission blocking antibodies encoded by the 10C fragment is termed "epitope I" (17). This epitope is located in the C-terminal part of Pfs48/45 and include the distal 6 cysteine residues. It was therefore speculated that protein fusions between GLURP.R0 and smaller fragments of Pfs48/45 which only contain the distal 6 cysteine residues might adopt a more correct protein fold in *L. lactis* as compared to the R0.10C protein fusion containing 10 cysteine residues. We have accordingly produced a protein fusion (R0-6C-6H) which contains the GLURP.R0 region fused in frame to a Pfs48/45 fragment containing the distal 6 cysteine residues. The C-terminus of this fusion protein is identical the C-terminus of the R0.10C hybrid protein.

An equivalent and more preferred embodiment RO-6C-6H:

(SEQ ID NO 25)
AERSTSENRNKRIGGPKLRGNVTSNIKFPSDNKGKIIRGSNDKLNKNSE

DVLEQSEKSLVSENVPSGLDIDDIPKESIFIQEDQEGQTHSELNPETSE

HSKDLNNNGSKNESSDIISENNKSNKVQNHFESLSDLELLENSSQDNLD

KDTISTEPFPNQKHKDLQQDLNDEPLEPFPTQIHKDYKEKNLINEEDSE

PFPRQKHKKVDNHNEEKNVFHENGSANGNQGSLKLKSFDEHLKDEKIEN

EPLVHENLSIPNDPIEQILNQPEQETNIQEQLYNEKQNVEEKQNSQIPS

LDLKEPTNEDILPNHNPLENIKQSESEINHVQDHALPKENIIDKLDNQK

EHIDQSQHNINVLQENNINNHQLEPQEKPNIESFEPKNIDSEIILPENV

ETEEIIDDVPSPKHSNHETFEEETSESEHEEAVSEKNAHETVEHEETVS

QESNPEKADNDGNVSQNSNNELNENEFVESEKSEHEARSKPKYEKKVIH

GCNFSSNVSSKHTFTDSLDISLVDDSAHISCNVHLSEPKYNHLVGLNCP

GDIIPDCFFQVYQPESEELEPSNIVYLDSQINIGDIEYYEDAEGDDKIK

LFGIVGSIPKTTSFTCICKKDKKSAYMTVTIDSARSHHHHHH

It is obvious that the fusion protein as such can comprise the amino acid sequence of GLURP or part hereof coupled to other immunogenic epitopes derived from Pfs48/45 or other cysteine rich proteins derived from *Plasmodium falciparum*, such as Pfs25, Pfs230, Pfs47, EBA175, Var2CSA (Table 1) or members of the PfEMP1, RIFIN, STEVOR protein families or a homologue hereof (17).

The fusion protein can even comprise other proteins derived from *Plasmodium falciparum*, to achieve an additional immunogenic response. Using MSP3 or part of MSP3 as a fusion partner to GLURP-R0 even enhances the production of the CYRP. A most preferred embodiment to increase the production yield of the CYRP the selected fragment of Pfs48/45 containing 6 cysteine residues (6C) is coupled to GLURP-R0 fused to MSP3 (R0-MSP3-6C-6H):

(SEQ ID NO 27)
AERSTSENRNKRIGGPKLRGNVTSNIKFPSDNKGKIIRGSNDKLNKNSE

DVLEQSEKSLVSENVPSGLDIDDIPKESIFIQEDQEGQTHSELNPETSE

HSKDLNNNGSKNESSDIISENNKSNKVQNHFESLSDLELLENSSQDNLD

KDTISTEPFPNQKHKDLQQDLNDEPLEPFPTQIHKDYKEKNLINEEDSE

PFPRQKHKKVDNHNEEKNVFHENGSANGNQGSLKLKSFDEHLKDEKIEN

EPLVHENLSIPNDPIEQILNQPEQETNIQEQLYNEKQNVEEKQNSQIPS

LDLKEPTNEDILPNHNPLENIKQSESEINHVQDHALPKENIIDKLDNQK

EHIDQSQHNINVLQENNINNHQLEPQEKPNIESFEPKNIDSEIILPENV

ETEEIIDDVPSPKHSNHETFEEETSESEHEEAVSEKNAHETVEHEETVS

QESNPEKADNDGNVSQNSNNELNENEFVESEKSEHEARSKTKEYAEKAK

NAYEKAKNAYQKANQAVLKAKEASSYDYILGWEFGGGVPEHKKEENMLS

HLYVSSKDKENISKENDDVLDEKEEEAEETEEEELERSKPKYEKKVIHG

CNFSSNVSSKHTFTDSLDISLVDDSAHISCNVHLSEPKYNHLVGLNCPG

DIIPDCFFQVYQPESEELEPSNIVYLDSQINIGDIEYYEDAEGDDKIKL

FGIVGSIPKTTSFTCICKKDKKSAYMTVTIDSARSHHHHHH

In another aspect, the invention relates a nucleic acid encoding the above mentioned fusion protein and the use of said nucleic acid for preparing a vaccine composition.

A preferred embodiment of a nucleic acid used for production of a CYRP is the following sequence for R0-10C-6H:

(SEQ ID NO 6)
ATGAAATTTAATAAAAAAAGAGTTGCAATAGCCACGTTTATTGCTTTGA

TATTTGTAAGTTTTTTTACAATATCATCAATCCAAGATGCTCAAGCAGC

CGAAAGATCTACAAGTGAGAATAGAAATAAACGAATCGGGGGTCCTAAA

TTAAGGGGTAATGTTACAAGTAATATAAAGTTCCCATCAGATAACAAAG

GTAAAATTATAAGAGGTTCGAATGATAAACTTAATAAAAACTCTGAAGA

TGTTTTAGAACAAAGCGAAAAATCGCTTGTTTCAGAAAATGTTCCTAGT

GGATTAGATATAGATGATATCCCTAAAGAATCTATTTTTATTCAAGAAG

ATCAAGAAGGTCAAACTCATTCTGAATTAAATCCTGAAACATCAGAACA

TAGTAAAGATTTAAATAATAATGGTTCAAAAAATGAATCTAGTGATATT

ATTTCAGAAAATAATAAATCAAATAAAGTACAAAATCATTTTGAATCAT

TATCAGATTTAGAATTACTTGAAAATTCCTCACAAGATAATTTAGACAA

AGATACAATTTCAACAGAACCTTTTCCTAATCAAAAACATAAAGACTTA

CAACAAGATTTAAATGATGAACCTTTAGAACCCTTTCCTACACAAATAC

ATAAAGATTATAAAGAAAAAAATTTAATAAATGAAGAAGATTCAGAACC

ATTTCCCAGACAAAAGCATAAAAAGGTAGACAATCATAATGAAGAAAAA

AACGTATTTCATGAAAATGGTTCTGCAAATGGTAATCAAGGAAGTTTGA

AACTTAAATCATTCGATGAACATTTAAAAGATGAAAAAATAGAAAATGA

ACCACTTGTTCATGAAAATTTATCCATACCAAATGATCCAATAGAACAA

ATATTAAATCAACCTGAACAAGAAACAAATATCCAGGAACAATTGTATA

ATGAAAAACAAATGTTGAAGAAAAACAAAATTCTCAAATACCTTCGTT

AGATTTAAAAGAACCAACAAATGAAGATATTTTACCAAATCATAATCCA

TTAGAAAATATAAAACAAAGTGAATCAGAAATAAATCATGTACAAGATC

ATGCGCTACCAAAAGAGAATATAATAGACAAACTTGATAATCAAAAAGA

ACACATCGATCAATCACAACATAATATAAATGTATTACAAGAAAATAAC

ATAAACAATCACCAATTAGAACCTCAAGAGAAACCTAATATTGAATCGT

TTGAACCTAAAAATATAGATTCAGAAATTATTCTTCCTGAAAATGTTGA

AACAGAAGAAATAATAGATGATGTGCCTTCCCCTAAACATTCTAACCAT

GAAACATTTGAAGAAGAAACAAGTGAATCTGAACATGAAGAAGCCGTAT

CTGAAAAAAATGCCCACGAAACTGTCGAACATGAAGAAACTGTGTCTCA

AGAAAGCAATCCTGAAAAAGCTGATAATGATGGAAATGTATCTCAAAAC

AGCAACAACGAATTAAATGAAAATGAATTCGTTGAATCGGAAAAAAGCG

AGCATGAAGCAGATAATACTGAAAAGGTTATATCAAGTATAGAAGGGAG

AAGTGCTATGGTACATGTACGTGTATTAAAATATCCACATAATATTTTA

TTTACTAATTTAACAAATGATCTTTTTACATATTTGCCGAAAACATATA

ATGAATCTAATTTTGTAAGTAATGTATTAGAAGTAGAATTGAATGATGG

AGAATTATTTGTTTTAGCTTGTGAACTAATTAATAAAAAATGTTTTCAA

GAAGGAAAAGAAAAAGCCTTATATAAAAGTAATAAAATAATTTATCATA

AAAACTTAACTATCTTTAAAGCTCCATTTTATGTTACATCAAAAGATGT

TAATACAGAATGTACATGCAAATTTAAAAATAATAATTATAAAATAGTT

TTAAAACCAAAATATGAAAAAAAAGTCATACACGGATGTAACTTCTCTT

CAAATGTTAGTTCTAAACATACTTTTACAGATAGTTTAGATATTTCTTT

AGTTGATGATAGTGCACATATTTCATGTAACGTACATTTGTCTGAACCA

AAATATAATCATTTGGTAGGTTTAAATTGTCCTGGTGATATTATACCAG

ATTGCTTTTTTCAAGTATATCAACCTGAATCAGAAGAACTTGAACCATC

CAACATTGTTTATTTAGATTCACAAATAAATATAGGAGATATTGAATAT

TATGAAGATGCTGAAGGAGATGATAAAATTAAATTATTTGGTATAGTTG

GAAGTATACCAAAAACGACATCTTTTACTTGTATATGTAAGAAGGATAA

AAAAAGTGCTTATATGACAGTTACTATAGATTCAGCACATCACCATCAT

CACCATTAG

And the nucleic acid sequence for R0-6C-6H:

(SEQ ID NO 26)
ATGAAATTTAATAAAAAAGAGTTGCAATAGCCACGTTTATTGCTTTGAT

ATTTGTAAGTTTTTTTACAATATCATCAATCCAAGATGCTCAAGCAGCCG

AAAGATCCACAAGTGAGAATAGAAATAAACGAATCGGGGGTCCTAAATTA

AGGGGTAATGTTACAAGTAATATAAAGTTCCCATCAGATAACAAAGGTAA

AATTATAAGAGGTTCGAATGATAAACTTAATAAAAACTCTGAAGATGTTT

```
TAGAACAAAGCGAAAAATCGCTTGTTTCAGAAAATGTTCCTAGTGGATTA
CTCAGATATAGATGATATCCCTAAAGAATCTATTTTTATTCAAGAAGATC
AAGAAGGTCAAATTCTGAATTAAATCCTGAAACATCAGAACATAGTAAAG
ATTTAAATAATAATGGTTCAAAAAATGAATCTAGTGATATTATTTCAGAA
AATAATAAATCAAATAAAGTACAAAATCATTTTGAATCATTATCAGATTT
AGAATTACTTGAAAATTCCTCACAAGATAATTTAGACAAAGATACAATTT
CAACAGAACCTTTTCCTAATCAAAAACATAAAGACTTACAACAAGATTTA
AATGATGAACCTTTAGAACCCTTTCCTACACAAATACATAAAGATTATAA
AGAAAAAATTTAATAAATGAAGAAGATTCAGAACCATTTCCCAGACAAA
AGCATAAAAAGGTAGACAATCATAATGAAGAAAAAAACGTATTTCATGAA
AATGGTTCTGCAAATGGTAATCAAGGAAGTTTGAAACTTAAATCATTCGA
TGAACATTTAAAAGATGAAAAAATAGAAAATGAACCACTTGTTCATGAAA
ATTTATCCATACCAAATGATCCAATAGAACAAATATTAAATCAAAAAACA
CCTGAACAAGAAACAAATATCCAGGAACAATTGTATAATGAAAAACAAAA
TGTTGAAGAAAATTCTCAAATACCTTCGTTAGATTTAAAAGAACCAACAA
ATGAAGATATTTTACCAAATCATAATCCATTAGAAAATATAAAACAAAGT
GAATCAGAAATAAATCATGTACAAGATCATGCGCTACCAAAAGAGAATAT
AATAGACAAACTTGATAATCAAAAAGAACACATCGATCAATCACAACATA
ATATAAATGTATTACAAGAAAATAACATAAACAATCACCAATTAGAACCT
CAAGAGAAACCTAATATTGAATCGTTTGAACCTAAAAATATAGATTCAGA
AATTATTCTTCCTGAAAATGTTGAAACAGAAGAAATAATAGATGATGTGC
CTTCCCCTAAACATTCTAACCATGAAACATTTGAAGAAGAAACAAGTGAA
TCTGAACATGAAGAAGCCGTATCTGAAAAAAATGCCCACGAAACTGTCGA
ACATGAAGAAACTGTGTCTCAAGAAAGCAATCCTGAAAAAGCTGATAATG
ATGGAAATGTATCTCAAAACAGCAACAACGAATTAAATGAAAATGAATTC
GTTGAATCGGAAAAAAGCGAGCATGAAGCAAGATCCGAAAAAAAAGTCAT
ACACGGATGTAACTTCTCTTCAAATGTTAGTTCTAAACATACTTTTACAG
ATAGTTTAGATATTTCTTTAGTTGATGATAGTGCACATATTTCATGTAAC
GTACATTTGTCTGAACCAAAATATAATCATTTGGTAGGTTTAAATTGTCC
TGGTGATATTATACCAGATTGCTTTTTTCAAGTATATCAACCTGAATCAG
AAGAACTTGAACCATCCAACATTGTTTATTTAGATTCACAAATAAATATA
GGAGATATTGAATATTATGAAGATGCTGAAGGAGATGATAAAATTAAATT
ATTTGGTATAGTTGGAAGTATACCAAAAACGACATCTTTTACTTGTATAT
GTAAGAAGGATAAAAAAGTGCTTATATGACAGTTACTATAGATTCAGCA
AGATCTCATCACCATCATCACCATTAG
```

The nucleic acid sequence for GLURP-R0-MSP3-6C-6H:

(SEQ ID NO 28)
```
ATGAAATTTAATAAAAAAGAGTTGCAATAGCCACGTTTATTGCTTTGAT
ATTTGTAAGTTTTTTTACAATATCATCAATCCAAGATGCTCAAGCAGCCG
AAAGATCCACAAGTGAGAATAGAAATAAACGAATCGGGGGTCCTAAATTA
AGGGGTAATGTTACAAGTAATATAAAGTTCCCATCAGATAACAAAGGTAA
AATTATAAGAGGTTCGAATGATAAACTTAATAAAAACTCTGAAGATGTTT
TAGAACAAAGCGAAAAATCGCTTGTTTCAGAAAATGTTCCTAGTGGATTA
GATATAGATGATATCCCTAAAGAATCTATTTTTATTCAAGAAGATCAAGA
AGGTCAAACTCATTCTGAATTAAATCCTGAAACATCAGAACATAGTAAAG
ATTTAAATAATAATGGTTCAAAAAATGAATCTAGTGATATTATTTCAGAA
AATAATAAATCAAATAAAGTACAAAATCATTTTGAATCATTATCAGATTT
AGAATTACTTGAAAATTCCTCACAAGATAATTTAGACAAAGATACAATTT
CAACAGAACCTTTTCCTAATCAAAAACATAAAGACTTACAACAAGATTTA
AATGATGAACCTTTAGAACCCTTTCCTACACAAATACATAAAGATTATAA
AGAAAAAATTTAATAAATGAAGAAGATTCAGAACCATTTCCCAGACAAA
AGCATAAAAAGGTAGACAATCATAATGAAGAAAAAAACGTATTTCATGAA
AATGGTTCTGCAAATGGTAATCAAGGAAGTTTGAAACTTAAATCATTCGA
TGAACATTTAAAAGATGAAAAAATAGAAAATGAACCACTTGTTCATGAAA
ATTTATCCATACCAAATGATCCAATAGAACAAATATTAAATCAACCTGAA
CAAGAAACAAATATCCAGGAACAATTGTATAATGAAAAACAAATGTTGA
AGAAAACAAATTCTCAAATACCTTCGTTAGATTTAAAAGAACCAACAA
ATGAAGATATTTTACCAAATCATAATCCATTAGAAAATATAAAACAAAGT
GAATCAGAAATAAATCATGTACAAGATCATGCGCTACCAAAAGAGAATAT
AATAGACAAACTTGATAATCAAAAAGAACACATCGATCAATCACAACATA
ATATAAATGTATTACAAGAAAATAACATAAACAATCACCAATTAGAACCT
CAAGAGAAACCTAATATTGAATCGTTTGAACCTAAAAATATAGATTCAGA
AATTATTCTTCCTGAAAATGTTGAAACAGAAGAAATAATAGATGATGTGC
CTTCCCCTAAACATTCTAACCATGAAACATTTGAAGAAGAAACAAGTGAA
TCTGAACATGAAGAAGCCGTATCTGAAAAAAATGCCCACGAAACTGTCGA
ACATGAAGAAACTGTGTCTCAAGAAAGCAATCCTGAAAAAGCTGATAATG
ATGGAAATGTATCTCAAAACAGCAACAACGAATTAAATGAAAATGAATTC
GTTGAATCGGAAAAAAGCGAGCATGAAGCAAGATCCAAAACAAAAGAATA
TGCTGAAAAAGCAAAAAATGCTTATGAAAAGCAAAAAATGCTTATCAAA
AAGCAAACCAAGCTGTTTTAAAAGCAAAGAAGCTTCTAGTTATGATTAT
ATTTTAGGTTGGGAATTTGGAGGAGGCGTTCCAGAACACAAAAAAGAAGA
AAATATGTTATCACATTTATATGTTTCTTCAAAGGATAAGGAAAATATAT
CTAAGGAAAATGATGATGTATTAGATGAGAAGGAAGAAGAGGCAGAAGAA
ACAGAAGAAGAAGAACTTGAAAGATCCGAAAAAAAAGTCATACACGGATG
TAACTTCTCTTCAAATGTTAGTTCTAAACATACTTTTACAGATAGTTTAG
ATATTTCTTTAGTTGATGATAGTGCACATATTTCATGTAACGTACATTTG
TCTGAACCAAAATATAATCATTTGGTAGGTTTAAATTGTCCTGGTGATAT
TATACCAGATTGCTTTTTTCAAGTATATCAACCTGAATCAGAAGAACTTG
AACCATCCAACATTGTTTATTTAGATTCACAAATAAATATAGGAGATATT
GAATATTATGAAGATGCTGAAGGAGATGATAAAATTAAATTATTTGGTAT
AGTTGGAAGTATACCAAAAACGACATCTTTTACTTGTATATGTAAGAAGG
```

-continued

```
ATAAAAAAAGTGCTTATATGACAGTTACTATAGATTCAGCAAGATCTCAT
CACCATCATCACCATTAG
```

TABLE 1

| | |
|---|---|
| SEQ ID 1 | GLURP protein sequence |
| SEQ ID 2 | GLURP nucleic acid sequence |
| SEQ ID 3 | Pfs48/45 protein sequence |
| SEQ ID 4 | Pfs48/45 nucleic acid sequence |
| SEQ ID 5 | R0-10C-6H protein sequence |
| SEQ ID 6 | R0-10C-6H nucleic acid sequence |
| SEQ ID 7 | R0-16C-6H protein sequence |
| SEQ ID 8 | R0-16C-6H nucleic acid sequence |
| SEQ ID 9 | tR0-10C protein sequence |
| SEQ ID 10 | tR0-10C nucleic acid sequence |
| SEQ ID 11 | tR0-16C protein sequence |
| SEQ ID 12 | tR0-16C nucleic acid sequence |
| SEQ ID 13 | EBA175 protein sequence |
| SEQ ID 14 | EBA175 nucleic acid sequence |
| SEQ ID 15 | Var2CSA protein sequence |
| SEQ ID 16 | Var2CSA nucleic acid sequence |
| SEQ ID 17 | Pfs230 protein sequence |
| SEQ ID 18 | Pfs230 nucleic acid sequence |
| SEQ ID 19 | Pfs47 protein sequence |
| SEQ ID 20 | Pfs47 nucleic acid sequence |
| SEQ ID 21 | Pfs25 protein sequence |
| SEQ ID 22 | Pfs25 nucleic acid sequence |
| SEQ ID 23 | MSP3 protein sequence |
| SEQ ID 24 | MSP3 nucleic acid sequence |
| SEQ ID 25 | R0-6C-6H protein sequence |
| SEQ ID 26 | R0-6C-6H nucleic acid sequence |
| SEQ ID 27 | R0-MSP3-6C-6H protein sequence |
| SEQ ID 28 | R0-MSP3-6C-6H nucleic acid seq. |

Since *Lactococcus lactis* lack the sophisticated ER machinery of disulphide bond formation we speculated that *Lactococcus lactis* being very cysteine poor in its proteome and lacking any disulphide assisting machinery would be unsuited for production of CYRPs like Pfs48/45 either because of instability of the protein or from an insufficient amount of tRNA for cystein leading to translational problems and premature termination of transcription and/or translation. However, contrary to expectations we found surprising high levels of expression of correctly folded Pfs48/45 in *Lactococcus lactis* when this protein was genetically linked to the N-terminal region of GLURP.

Since vaccines based on GLURP and Pfs48/45 induce IgG antibody responses with different in vitro activities and possibly complement each other as targets for the immune system, the GLURP$_{133-500}$ region (termed tR0) was fused to both the Pfs48/45$_{27-417}$ region (termed 16C) creating the recombinant fusion protein tR0-16C and the Pfs48/45$_{159-428}$ region (termed 10C) regions creating the recombinant fusion protein tR0-10C. These two constructs were introduced in *Lactococcus lactis* in a gene expression system, which is based on the pH and growth phase regulated promoter, P170, from *Lactococcus lactis* (1, 9, 16). This gene expression system offers a simple fermentation procedure, which has been developed specifically for the P170 promoter.

*Lactococcus lactis* was chosen as expression host because i) it is a well characterized industrial generally recognized as safe (GRAS) microorganism, best known for its use in the production of fermented dairy products, ii) it can be grown in a defined synthetic medium, iii) it does not produce toxic substances and iv) it has the possibility of secretory protein expression, which offers easy recovery of target protein with the added advantage of optimizing growth conditions for preservation of target protein activity and stability.

The tR0 region of GLURP and the 16C or the 10C region of Pfs48/45 have now been produced, as the hybrid proteins, tR0-16C and tR0-10C using *Lactococcus lactis*, with estimated expression levels of up to 50 mg fusion protein pr. liter culture supernatant. To facilitate purification a C-terminal hexahistidine (6H) was introduced in each construct leading to constructs termed tR0-16C-6H and tR0-10C-6H, respectively. Following addition of 6H the tR0 was changed to the GLURP$_{27-500}$ region (termed R0). Both permutations didn't influence the protein expression levels.

In contrast, when either of the 16C or 10C regions of Pfs48/45 were cloned individually into the same *Lactococcus lactis* expression plasmid without the GLURP fusion partner, protein yields were low, and the recombinant proteins rPfs45/48_16C, rPfs45/48_10C seemed to remain inside the cell indicating little or no secretion.

Thus, R0 helps in both cases to increases expression levels of these otherwise non-secreted 16C and 10C protein fragments. Moreover, R0 also helps to increase the yield of correctly folded Pfs48/45 protein species in the culture supernatant as determined by the reactivity with mAb 85RF45.1 which possesses strong TB activity and is specific for the conformational epitope I. This is a surprising ability of R0 which can be used with other malaria antigens also.

When R0-10C-6H and R0-16C-6H are produced, the majority (>60%) of the protein is produced as aggregates of disulphide bonded monomers, as judged from a non-reducing SDS-PAGE gel. The monomeric form is stabilized by modifying the redox potential of the medium by the addition of L-cysteine, dithiothreitol (DTT), reduced glutathione (GSH) or tris(2-carboxyethyl)phosphine (TCEP) in the range of 1-20 mM, making the monomer fraction >50%.

The monomeric protein can be separated from the aggregates using gel filtration. Immunoreactivity of these monomeric species using a set of monoclonal antibodies targeting epitope I, IIb and III (FIG. 1) is very low, which indicates uncorrect cysteine pairing in the monomer. The correct cysteine pairing of R0-10C-6H can be achieved by modifying the redox potential of the buffer by the addition of reduced and oxidized glutathione or cysteine or cysteamine or DTT or TCEP to the washing buffer in the range of 1-10 and 0.1-5, respectively during the initial immobilized metal-ion affinity chromatography (IMAC) capturing step. This treatment leads to a change in the immunoreactivity towards the beforementioned monoclonal antibodies. This change of the monomeric R0-10C-6H hybrid protein have been studied in rats with Freunds complete/incomplete adjuvant. Three rats received R0-10C-6H purified without glutathione (R0-10C-6H$_{-GSH}$) and three rats received R0-10C-6H purified with glutathione (R0-10C-6H$_{+GSH}$). When the sera from the rats where tested in an ELISA against native Pfs48/45 extracted from gametocytes, the three R0-10C-6H$_{-GSH}$ rat sera almost didn't respond, while the three R0-10C-6H$_{+GSH}$ rat sera responded well. One out of the three R0-10C-6H$_{+GSH}$ rat sera demonstrated >90% transmission blocking activity.

In another embodiment of this invention, fragments of Pfs48/45 are fused in-frame to GMZ2, a protein fusion between GLURP.R0 and MSP3, thus creating R0.MSP3.10C or R0.MSP3.6C chimera. These alternative versions of Pfs48/45 aim to beside the main objective of increasing the yield of correctly folded protein species in the culture supernatant of *L. lactis*, to expand the breath of the immune response against *P. falciparum* by including responses against one (GLURP.R0) or two (GLURP.R0 and MSP3) antigens from the blood stage of the infection, and at the same time potentially enhance antibody responses against correctly folded epitope I of Pfs48/45.

The GLURP-Pfs48/45 hybrid protein secreted in the *Lactococcus lactis* or in another lactic acid bacteria expression system under controlled medium redox potential and purified under controlled buffer redox potential, therefore has four major advantages compared to the Pfs48/45 molecule alone:

i) GLURP enhance secretion of Pfs48/45 ii) Medium redox potential stabilizes formation of monomeric Pfs48/45 iii) Buffer redox potential enhances proper folding of Pfs48/45.

iv) The fusion protein elicits antibodies that target the sexual as well as the a-sexual stages of *Plasmodium falciparum.*

Definitions

By monomeric form is meant a protein species with the molecular weight determined by mass spectroscopy to be equal to the molecular weight of the protein as calculated from the amino acid sequence of the protein.

By multimeric form is meant a protein species with the molecular weight determined by mass spectroscopy to be equal to two times or more of the molecular weight of the monomeric form. Under reducing conditions the multimeric and monomeric forms are the same.

By correctly folded monomeric form is meant the monomeric form protein species which has correct disulphides as determined by conformational monoclonal antibodies.

By conformational monoclonal antibodies is meant antibodies originating from a immortalized single B-cell line and which can detect correctly folded monomeric form of protein in a Western blot or ELISA under nonreducing conditions, but not under reducing conditions.

By controlled medium redox potential is meant the addition of reduced forms of L-cysteine or DTT or glutathione or TCEP or cysteamine or any other small sulfhydryl containing compound capable of reducing cystines in proteins in the range of 1-20 mM, preferably 10 mM of L-cysteine to the medium in which the protein production is taking place.

By controlled buffer redox potential is meant the addition of reduced and oxidized forms of L-cysteine or DTT or glutathione or TCEP or cysteamine or any other small sulfhydryl containing compound capable of reducing or oxidixing cystines or cysteines in proteins. Concentrations is in the range of 1-10 mM (of the reduced form) and 0.1-5 mM (of the oxidized form), respectively, preferably 4 mM reduced L-cysteine and 0.4 mM oxidized L-cysteine to a washing buffer during the initial immobilized metal-ion affinity chromatography (IMAC) capturing step. The contact time with the buffer can be between 15 min and 4 hours, but preferably 30 min.

By potency of a given protein sample is meant the value in arbitrary units which comes from division of the EC50 value from a standard 2-SITE ELISA with the EC50 value from a standard 1-SITE ELISA.

By relative potency of a given protein sample is meant the potency of a sample divided by the potency of a reference sample. E.g. if the reference sample is input for a purification step, then the relative potency of an eluted sample equals to fold purification in the given step. If the reference sample is immunopurified sample, the relative potency equals the actual purity of the given sample.

By a glutamate rich protein is meant any protein with more than 10% glutamic acid residues.

By GLURP is meant the glutamate-rich protein from *Plasmodium falciparum* or a fraction of this protein. A preferred fraction is the $GLURP_{27-500}$ region is termed R0.

By cysteine-rich protein (CYRP) is meant any protein with more than six cysteine residues. Cysteine rich proteins derived from *Plasmodium falciparum* e.g. Pfs45/48, PfEMP1, RIFIN, STEVOR, Pfs230, EBA-175, Pfs25, Pfs47, Var2CSA or immunogenic fragments hereof. Producing full-length CYRP on recombinant form is often difficult due to incorrect protein folding and possibly aggregation as illustrated with our 16C construct. Instead, one may focus on a small fragment of the protein comprising one or several B-cell epitopes, defined as "immunogenic fragments". Examples of preferred fragments of Pfs48/45 are described in example 6 as fragment 10C and 6C. Single amino acid deletions or substitution that does not alter the antibody-binding properties of the epitope can also be beneficial if they results in a more correct folding of the polypeptide fragment and a more favorable presentation to the immune system.

By homologues are meant polypeptides or polypeptide fragments where single amino acid deletions or substitutions of the fragment that do not alter the immunogenic properties of the epitope have been introduced or various length of a fragment that does not alter the immunogenic properties of the epitope. Examples of homologue fragments of Pfs48/45 are described in table 7 in example 6. Another type of homologue can be fragments including amino acids that make up part of a restriction cleaving site e.g. the N-terminal aa AERS in some of the present constructs.

Immunogenic Fragment or Epitope

An immunogenic fraction, fragment or epitope is defined as a part of or a fragment of the protein that induces an immune response in a biological sample or an individual currently or previously infected with a microorganism such as malaria.

The immune response may be monitored by one of the following methods:

An in vitro cellular response is determined by release of a relevant cytokine such as IFN-γ, from lymphocytes withdrawn from an animal or human being currently or previously infected with malaria, or by detection of proliferation of these T cells. The induction being performed by the addition of the polypeptide or the immunogenic portion to a suspension comprising from $1\times10^5$ cells to $3\times10^5$ cells per well. The cells being isolated from the blood, the spleen, the liver or the lung and the addition of the polypeptide or the immunogenic portion resulting in a concentration of not more than 20 μg per ml suspension and the stimulation being performed from two to five days. For monitoring cell proliferation the cells are pulsed with radioactive labeled Thymidine and after 16-22 hours of incubation detecting the proliferation by liquid scintillation counting. A positive response being a response more than background plus two standard deviations. The release of IFN-γ can be determined by the ELISA method, which is well known to a person skilled in the art. A positive response being a response more than background plus two standard deviations. Other cytokines than IFN-γ could be relevant when monitoring the immunological response to the polypeptide, such as IL-12, TNF-α, IL-4, IL-5, IL-10, IL-6, TGF-β. Another and more sensitive method for determining the presence of a cytokine (e.g. IFN-γ) is the ELISPOT method where the cells isolated from either the blood, the spleen, the liver or the lung are diluted to a concentration of preferable of 1 to $4\times10^6$ cells/ml and incubated for 18-22 hrs in the presence of the polypeptide or the immunogenic portion resulting in a concentration of not more than 20 μg per ml. The cell suspensions are hereafter diluted to 1 to $2\times10^6$/ml and transferred to Maxisorp plates coated with anti-IFN-γ and incubated for preferably 4 to 16 hours. The IFN-γ producing cells are determined by the use of labelled secondary anti-IFN-γ antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or a malaria infected person where the T cell lines have been driven with either live *P. falciparum*, extracts from the parasite or culture filtrate for 10 to 20 days with the addition of IL-2. The induction being performed by addition of not more than 20 µg polypeptide per ml suspension to the T cell lines containing from $1 \times 10^5$ cells to $3 \times 10^5$ cells per well and incubation being performed from two to six days. The induction of IFN-γ or release of another relevant cytokine is detected by ELISA. The stimulation of T cells can also be monitored by detecting cell proliferation using radioactively labeled Thymidine as described above. For both assays a positive response being a response more than background plus two standard deviations.

An in vivo cellular response which may be determined as a positive DTH response after intradermal injection or local application patch of at most 100 µg of the polypeptide or the immunogenic portion to an individual who is clinically or subclinically infected with *P. falciparum*, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the polypeptide or the immunogenic portion is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the OD e.g. by ELISA where a positive response is a response of more than background plus two standard deviations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection. Readout for induced protection could be decrease of the parasite density compared to non-vaccinated animals; prolonged survival times compared to non-vaccinated animals and diminished weight loss compared to non-vaccinated animals.

Homologue Protein

Homology is defined as an analogue or variant of the fusion protein of the present invention. The fusion protein is characterized by specific amino acids and is encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". Substitutions are preferably silent substitutions in the codon usage which will not lead to any change in the amino acid sequence, but may be introduced to enhance the expression of the protein. These are defined according to the following table. Amino acids in the same block in the second column and preferably in the same line in the third column may be substituted for each other. The amino acids in the third column are indicated in one-letter code.

TABLE 2

| ALIPHATIC | Non-polar | GAP |
| --- | --- | --- |
| | | ILV |
| | Polar-uncharged | CSTM |
| | | NQ |
| | Polar-charged | DE |
| | | KR |
| AROMATIC | | HFWY |

Fusion Proteins

A recombinant fusion protein is encoded by a nucleotide sequence, which is obtained by genetically joining nucleotide sequences derived from different regions of one gene and/or by joining nucleotide sequences derived from two or more separate genes. These nucleotide sequences may be derived from *P. falciparum*, but they may also be derived from other organisms, the plasmids used for the cloning procedures or from other nucleotide sequences. According to the present invention the fusion proteins are produced in a lactic acid bacteria system.

As used herein, the term "lactic acid bacterium" designates a gram-positive, microaerophilic or anaerobic bacterium which ferments sugars with the production of acids including lactic acid as the predominantly produced acid, acetic acid and propionic acid. The industrially most useful lactic acid bacteria are found among *Lactococcus* spp., *Streptococcus* spp., *Lactobaccillus* spp., *Leuconostoc* spp., *pediococcus* spp., *Brevibacterium* spp. And *Propionibacterium* spp. Additionally, lactic acid producing bacteria belonging to the group of the strict anaerobic bacteria, bifidobacteria, i.e. *Bifidobacterium* spp., which are frequently used as food starter cultures alone or in combination with lactic acid bacteria, are generally included in the group of lactic acid bacteria. A presently preferred host cell species is *Lactococcus lactis*.

Following the transformation of the selected lactic acid bacterial host species, the transformed bacterium is cultivated under conditions where the fusion protein is expressed. The culture medium used to cultivate recombinant lactic acid bacterial host cells can be any conventional medium which is suitable for the purpose e.g. with respect to its nutrient composition and pH. In useful embodiments, the host cells are cultivated under anaerobic conditions in an industrial production scale. In the present context, large scale production or industrial production scale indicates that the volume of culture medium in the fermentation vessel is at least 1 liter, such as at least 5 liter e.g. at least 10 liter. It is also envisaged that the volume can be larger such as at least 100 liter including at least 250 liter.

The choice of specific fermentation conditions such as fermentation time and temperature depends on the requirements of the selected lactic acid bacterial host cell. Generally, the fermentation time is in the range of 10 to 30 hours such as in the range of 20-30 hours.

Preferably, the amount of fusion protein that is secreted into the culture medium after completion of the lactic acid bacterial fermentation process is at least 20 mg/l, such as at least 50 mg/l, preferably at least 100 mg/l e.g. at least 250 mg/l including at least 500 mg/l. The monomeric form of the cysteine rich protein fused to a glutamate rich protein can be enhanced by modifying the redox potential of the medium in which the protein is secreted into. This is achieved by the addition of reduced forms of L-cysteine or DTT or glutathione or TCEP or cysteamine or any other small sulfhydryl containing compound capable of reducing cystines in proteins in the range of 1-20 mM, preferably 10 mM of L-cysteine to the culture medium.

In a final step of the method according to the invention, the fusion protein is purified. Depending on whether or not the coding sequence is associated with a signal sequence which affects the secretion of the fusion protein across the cell membrane and into the culture medium, the step of purification includes either the isolation of the fusion protein from the host cell (no signal sequence) or that it is isolated directly from the culture medium. These steps can be carried out using any conventional method of down-stream processing.

Generally, it is preferred that the fusion protein is secreted into the culture medium rather than being accumulated intracellularly, as it appears that a polypeptide that is not subjected to extraction from the host cell may have a higher bioreactivity than a cell-extracted derived polypeptide.

Thus, when the fusion protein is secreted into the culture medium, the first step of purification is a separation of the host cell e.g. by centrifugation or filtration followed by isolating the fusion protein from the supernatant or the filtrate. It is preferred that the fusion protein amounts to at least 25% of the total protein content of the supernatant or the filtrate such as at least 30%, including at least 40% e.g. at least 50%.

Generally, the supernatant or filtrate is subjected to a step of concentration and/or at least partial purification using any conventional method for such purposes such as e.g. cross-flow filtration, salting out, immobilized metal-ion affinity chromatography, immunoaffinity chromatography, hydrophobic interaction chromatography and/or ion exchange chromatography. In preferred embodiments, the concentration and at least partially purified preparation of the fusion protein contains at least 0.5 mg/ml of fusion protein, such as at least 1.0 mg/ml including at least 1.5 mg/ml e.g. at least 2.0 mg/ml.

The amount of correctly folded monomeric form of the cysteine rich protein fused to a glutamate rich protein can be enhanced in the initial partial purification by treatment of the material with a buffer containing a controlled buffer redox potential.

The crude or optionally partially purified fusion protein preparation obtained by the purification steps as defined above may be used as such or it may be formulated e.g. splitting the fusion protein in its components, to provide a storage stable and convenient composition such as an immunogenic composition or a vaccine. Thus, such ready-to-use composition may e.g. include preserving agents, polypeptide stabilizing agents or substances which enhances the reactivity of the fusion protein. Additionally, a crude protein preparation may be subjected to further concentration or dilution in order to obtain a pre-determined amount or activity of the ready-to-use composition such as an immunogenic composition or a vaccine.

Vaccine, Protein

The invention pertains to an immunogenic composition, a vaccine comprising a fusion protein according to the invention and the production hereof. In order to ensure optimum performance of such a vaccine composition it is preferred that it comprises an immunologically and pharmaceutically acceptable carrier, vehicle or adjuvant.

An effective immunogenic composition or vaccine, wherein a protein of the invention is recognized by the animal, will in an animal model be able to decrease parasite load in blood and target organs, prolong survival times and/or diminish weight loss after challenge with a malarial parasite, compared to non-vaccinated animals.

Furthermore, the fusion protein of the invention may be coupled to a carbohydrate or a lipid moiety, e.g. a carrier, or a modified in other ways, e.g. being acetylated.

When produced in a microorganism the fusion protein of the invention will normally not be acetylated if no special measures are taken. The acetylation may be advantageous as acetylated polypeptides may be more stable in cell, blood or body and tissue fluids. Furthermore, the acetylation may confer the polypeptide with a structure and confirmation which mimics the structure and confirmation of the native *P. falciparum* antigen.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyldi-octadecylammonium bromide (DDA), Quil A, poly I:C, aluminium hydroxide, Freund's incomplete adjuvant, IFN-γ, IL-2, IL-12, monophosphoryl lipid A (MPL), Treholose Dimycolate (TDM), Trehalose Dibehenate and muramyl dipeptide (MDP).

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFN-γ inducers such as poly I:C in combination with the above-mentioned adjuvants.

Another interesting possibility for achieving adjuvant effect is to employ the technique described in Gosselin et al., 1992 (7). In brief, a relevant antigen such as an antigen of the present invention can be conjugated to an antibody (or antigen binding antibody fragment) against the Fcγ receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

In many instances, it will be necessary to have multiple administrations of the vaccine. Especially, vaccines can be administered to prevent an infection with malaria and/or to treat established malarial infection. When administered to prevent an infection, the vaccine is given prophylactically, before definitive clinical signs or symptoms of an infection are present.

Due to genetic variation, different individuals may react with immune responses of varying strength to the same protein. Therefore, the vaccine according to the invention may comprise several different proteins in order to increase the immune response. The vaccine may comprise two or more polypeptides or immunogenic portions, where all of the proteins are as defined above, or some but not all of the peptides may be derived from *P. falciparum* or other microorganisms. In the latter example, the polypeptides not necessarily fulfilling the criteria set forth above for polypeptides may either act due to their own immunogenicity or merely act as adjuvants.

The vaccine may comprise 1-20, such as 2-20 or even 3-20 different proteins or fusion proteins, such as 3-10 different proteins or fusion proteins.

The invention also pertains to a method for immunising an animal, including a human being, against malaria caused by e.g. *P. falciparum*, comprising administering to the animal the fusion protein of the invention, or a vaccine composition of the invention as described above, or a living vaccine described below.

The invention also pertains to a method for producing an immunologic composition according to the invention, the method comprising preparing, synthesising or isolating a fusion protein according to the invention, and solubilizing or dispersing the fusion protein in a medium for a vaccine, and optionally adding other antigens and/or a carrier, vehicle and/or adjuvant substance.

Another aspect of the invention is producing the hybrid protein of the invention in a recombinant microorganism which, besides expressing the DNA sequence encoding the present hybrid protein, additionally expresses one or more antigens having a therapeutic or protective effect against another disease than malaria, e.g. tuberculosis. These other antigens can be expressed as separate antigens or as fused to the hybrid protein of the present invention. Examples of other antigens effective against *M. tuberculosis* are ESAT6, CFP7, CFP10, CFP29, ORF2c, TB 13, MPT59, α-crystalline, Rv0285 and hybrids hereof, but the concept is not limited to tuberculosis or antigens against tuberculosis alone.

Vaccine DNA.

The nucleic acid fragments of the invention may be used for effecting in vivo expression of antigens, i.e. the nucleic acid fragments may be used in so-called DNA vaccines as reviewed in Ulmer et al 1993, which is included by reference.

Hence, the invention also relates to a vaccine comprising a nucleic acid fragment according to the invention, the vaccine effecting in vivo expression of antigen by an animal, including a human being, to whom the vaccine has been administered, the amount of expressed antigen being effective to confer substantially increased resistance to infections caused by *P. falciparum* in an animal, including a human being.

The efficacy of such a DNA vaccine can possibly be enhanced by administering the gene encoding the expression product together with a DNA fragment encoding a polypeptide which has the capability of modulating an immune response.

Live Recombinant Vaccines

One possibility for effectively activating a cellular immune response for a vaccine can be achieved by expressing the relevant antigen in a vaccine in a non-pathogenic microorganism or virus. Well-known examples of such microorganisms are *Mycobacterium bovis* BCG, *Salmonella* and *Pseudomona* and examples of viruses are Vaccinia Virus and Adenovirus.

Therefore, another important aspect of the present invention is an additional quality of the living BCG vaccine presently available, wherein one or more copies of a DNA sequence encoding one or more fusion proteins as defined above has been incorporated into the genome of the microorganism in a manner allowing the micro-organism to express and secrete the protein. The incorporation of more than one copy of a nucleotide sequence of the invention is contemplated to enhance the immune response.

Another aspect of the invention is a non-pathogenic microorganism, such as e.g. *Lactococcus lactis* or BCG, expressing the DNA sequence encoding one or more fusion proteins as defined above and additionally expressing one or more antigens having a therapeutic or protective effect against a disease different from malaria, such as e.g. tuberculosis caused by *Mycobacterium tuberculosis*. These other antigens can be expressed as separate antigens or as fused to the hybrid protein of the present invention. Examples of other antigens effective against *M. tuberculosis* (identified by their Sanger database accession number) are Rv3875 (ESAT6), Rv1886c (Ag85B), Rv0288 (CFP7), Rv3874 (CFP10), Rv0798c (CFP29), Rv2031c (α-crystalline) and Rv0285 or fragments or hybrids hereof most preferable the ESAT6-Ag85B hybrid, but the concept is not limited to tuberculosis or antigens against tuberculosis alone.

The effect of such a DNA-vaccine can possibly be enhanced by administering the gene encoding the expression product together with a DNA fragment encoding a polypeptide which has the capability of modulating an immune response. For instance, a gene encoding lymphokine precursors or lymphokines (e.g. INF-γ, IL-2, IL-12) could be administered together with the gene encoding the immunogenic fusion protein, either by administering two separate DNA fragments or by administering both DNA fragments included in the same vector.

Another possibility is to integrate the DNA encoding the polypeptide according to the invention in an attenuated virus such as the vaccinia virus or Adenovirus (40). The recombinant vaccinia virus is able to replicate within the cytoplasma of the infected host cell and the protein of interest can therefore induce an immune response, which is envisioned to induce protection against malaria.

Therapeutic Vaccine

The invention also relates to the use of a fusion protein or nucleic acid of the invention for use as therapeutic vaccines as have been described in the literature exemplified by D. Lowry (15). Antigens with therapeutic properties may be identified based on their ability to diminish the severity of malarial infection in experimental animals or prevent reactivation of previous infection, when administered as a vaccine. The composition used for therapeutic vaccines can be prepared as described above for vaccines.

Transmission-blocking Vaccines

The objective of a transmission-blocking vaccine is to prevent an individual from becoming infected with *Plasmodium* parasites by mosquito bites of the *Anopheles* vector. As a result, the spread of malaria in the population is expected to decrease with subsequent reduction of the disease. Transmission-blocking vaccines are based on sexual- or sporogonic-specific antigens and designed to elicit transmission-blocking antibodies with the ultimate aim to arrest the development of sporogonic stages inside the mosquito. Human transmission-blocking antibodies are passively ingested together with parasites when mosquitoes take a blood meal and will bind to the parasites thereby interfering with zygote formation.

LEGENDS TO FIGURES

FIG. 1: Structures and properties of specific subdomains cloned. The top line shows the native Pfs45/48 with the position of the 16 cysteine residues indicated. Lines below show the portion of Pf48/45 included in the 16C, 10C, 6C, 6N, and 10N constructs.

Figure 2:
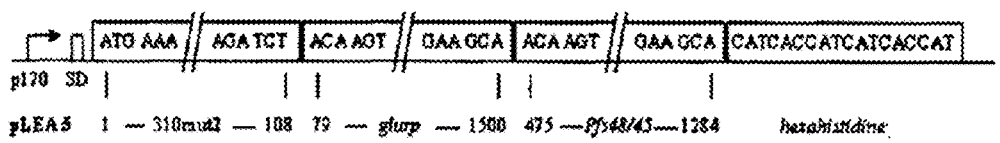

FIG. 2: Schematic representation the pLEA 5 expression constructs used in *L. lactis*. The position of vector-encoded promoter P170, Shine-Dalgarno sequence (SD), and 310mut2 signal peptide are indicated. The signal peptidase is predicted to cleave between amino acid nos. 32 and 33, thus leaving Ala-Glu residues in the N-terminal end of the mature recombinant proteins. The nucleotide numbering of glurp and Pfs48/45 was relative to A in the ATG codon of M59706 and (XM_001350145), respectively.

Figure 3:
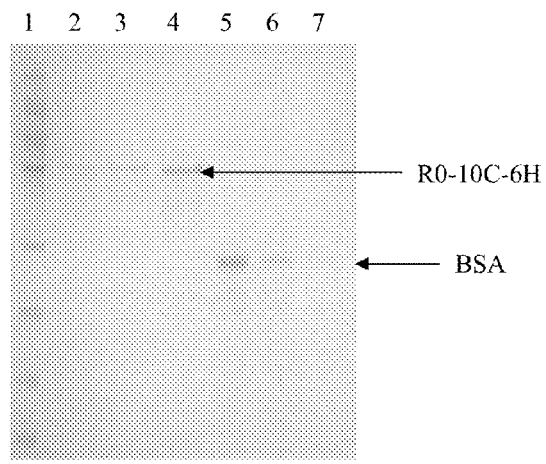

FIG. 3: Coomassie stained SDS-PAGE of culture supernatant. Lane 1: 5 µl HiMark Protein Ladder, Lane 2-4: culture supernatant taken after 16 h, 18 h and 20 h of cultivation respectively. Loaded 20 µl sample +4 µl 6×SDS sample loading buffer pr. well. Lane 5-7: 1 µg, 0.5 µg and 0.2 µg of Bovine Serum Albumin respectively. Estimated yield of recombinant protein after 20 h of cultivation is 25-50 mg/L (20 µl on an SDS-PAGE/Coomassie gel gives intensity between 0.5 and 1.0 µg BSA).

Figure 4:
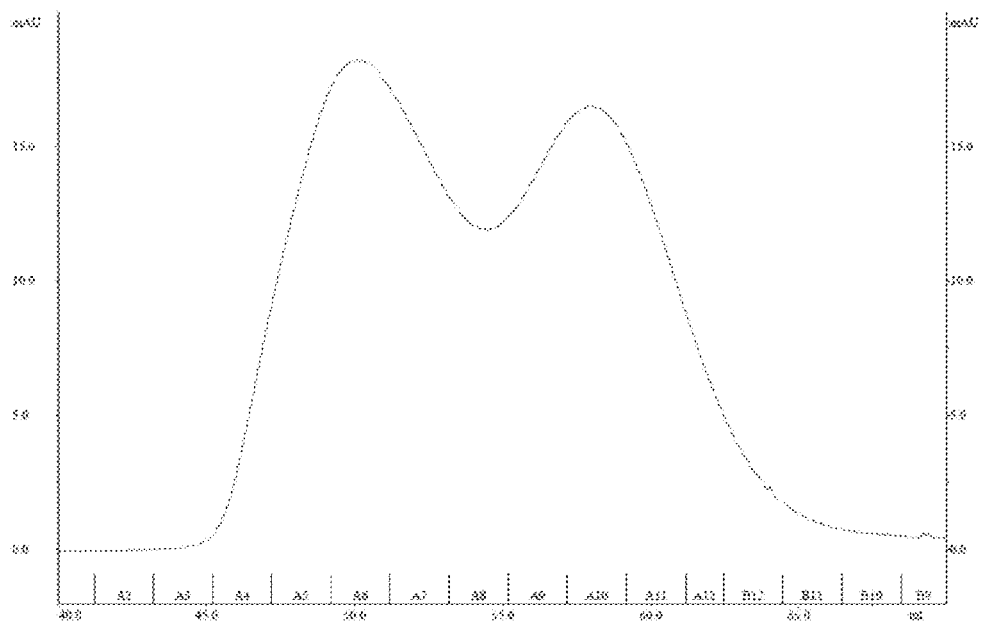

FIG. 4: Separation of different forms of R0-10C-6H on a 16/60 Superdex 200 column. The X-axis is the retention volume (in ml) and the black chromatogram shows the UV280 signal (seen on the Y-axis in arbitrary units). The fraction indicators on the X-axis indicate the fractionation profile. Fraction A4-A7 (approx. retention volume between 45-53 ml) corresponds to peak 1 and contains mainly multimeric R0-10C-6H. Fractions A8-A9 (approx. retention volume between 53 and 57 ml) contains a mixture of dimeric and monomeric forms of R0-10C-6H. Fraction A10-B12 (approx. retention volume between 57 and 65 ml) contains the monomeric form of R0-10C-6H.

Figure 5:
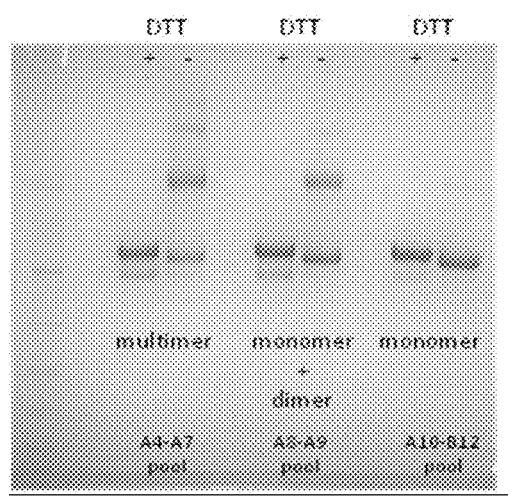

FIG. 5: Coomassie stained SDS-PAGE of fraction pools from the gel filtration of R0-10C-6H seen in FIG. 4. 3 µg of protein is loaded in each well. Samples are loaded with and without the presence of 50 mM DTT.

Figure 6:
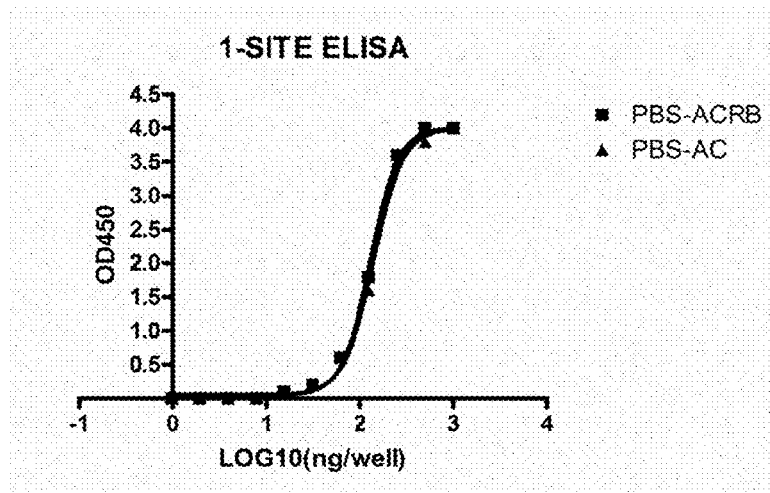

FIG. 6: 1-SITE ELISA of purified R0-10C-6H with (PBS-ACRB) or without (PBS-ACBB) redox buffer wash. Protein was coated with two fold dilution of protein starting at 1000 ng. Anti-hexahistidine(C-term)-HRP was used as detecting antibody and TMB for developing.

Figure 7:
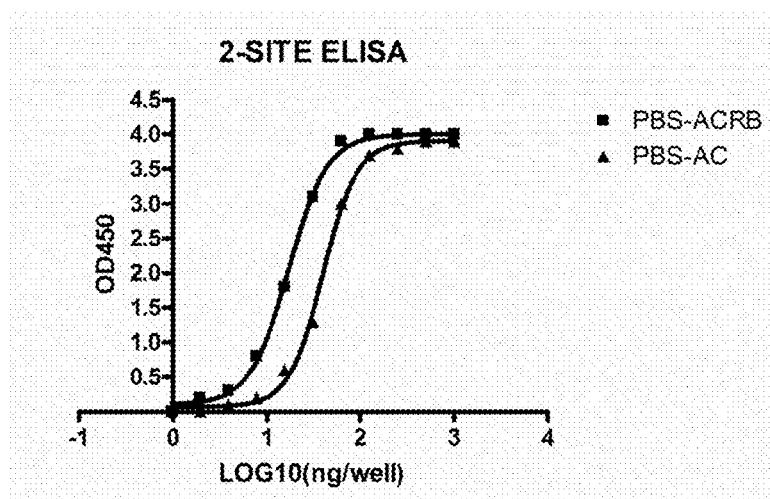

FIG. 7: 2-SITE ELISA of purified R0-10C-6H with (PBS-ACRB) or without (PBS-ACBE) redox buffer wash. 250 ng of monoclonal antibody, 85RF45.1, was coated as capturing antibody and incubation with two fold dilution of protein starting at 1000 ng. Anti-hexahistidine(C-term)-HRP was used as detecting antibody and TMB for developing.

Figure 8:
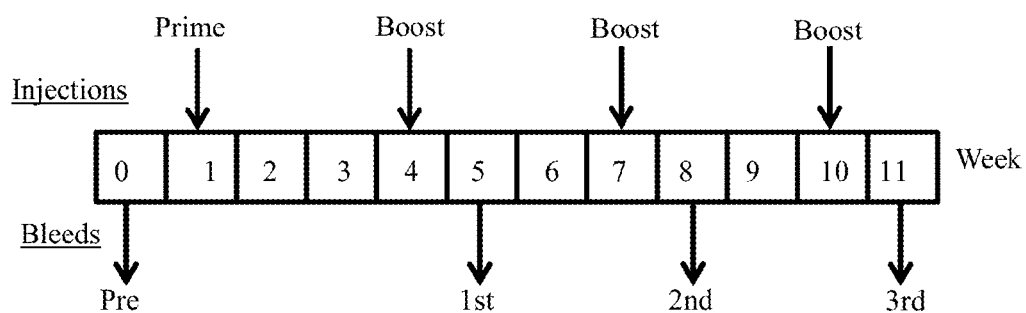

FIG. 8: Immunization schedule. Rats where divided into two groups (Group 1 and Group 2) with three rats in each. Group 1 was injected with the PBS-ACRB protein and Group 2 with the PBS-ACBB protein. At day zero (2-3 weeks prior to priming immunization) a pre-bleed was taken. Three boosts where made with 3 weeks apart starting three weeks after the priming Bleeds where taken 1 week after each of the boosts with $3^{rd}$ bleed being the final bleed.

Figure 9:
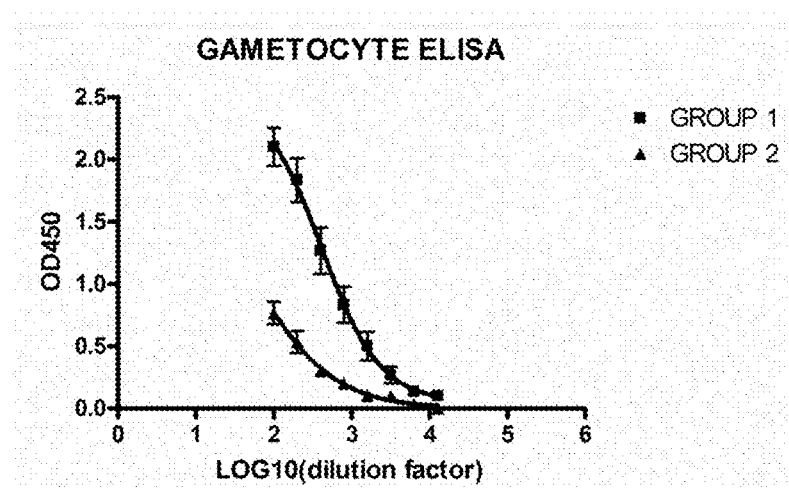

FIG. 9: Comparison in gametocyte ELISA reactivity. Sera were tested for reactivity towards native Pfs48/45 from gametocyte extract. Gametocyte extract was coated on the plate. The rat sera was used in two-fold dilutions (starting from 100 fold diluted) as primary antibody and HRP labeled rabbit anti-rat as secondary antibody was used as detecting antibody with TMB for developing. The points represent the mean and standard deviation of the $3^{rd}$ bleed from the three animals in each group.

Figure 10:
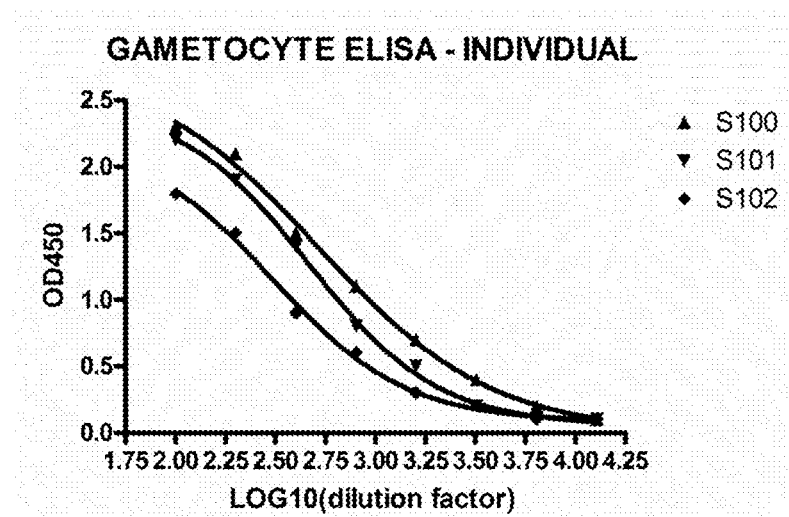

FIG. 10: Comparison between individual animals from Group 1. The same data as for FIG. 9, but with each point representing each animal.

Figure 11:
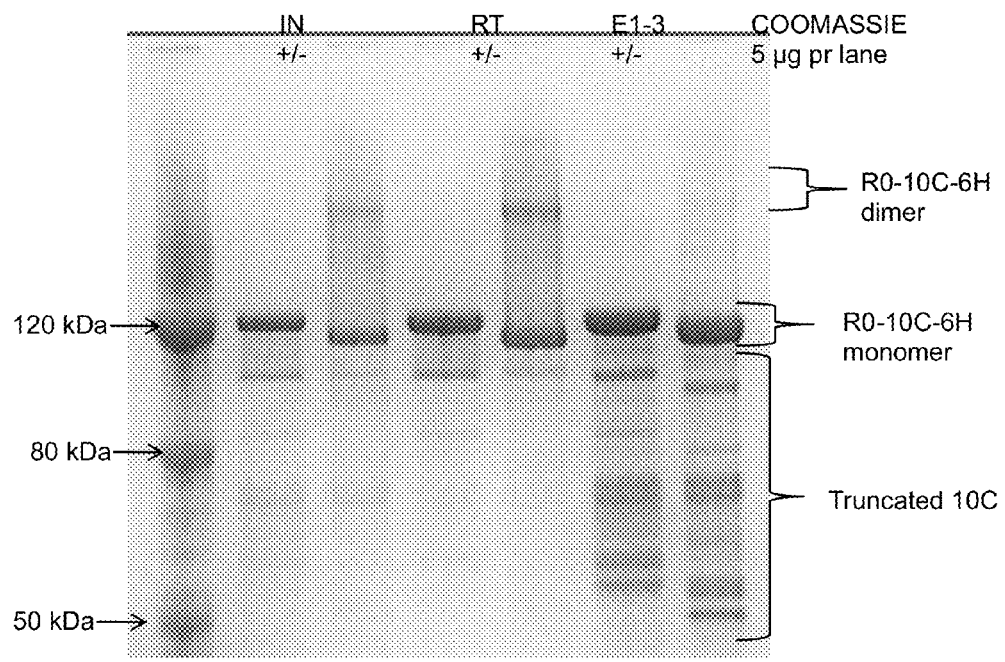

FIG. 11: SDS-PAGE of samples from immunopurification. Loaded 5 µg of protein in each well +/DTT and used Coomassie staining.

Figure 12:
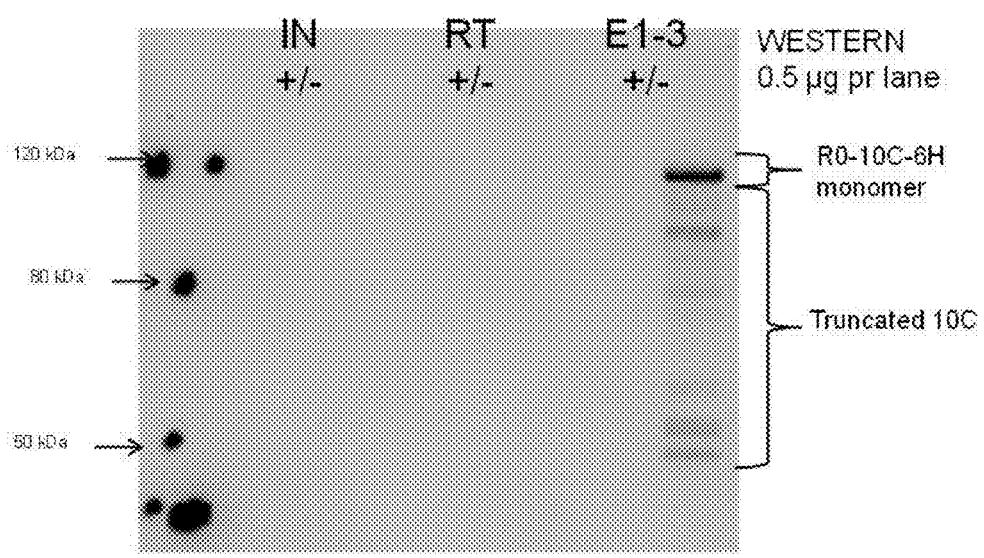

FIG. 12: Western blot of samples from immunopurification. Loaded 0.5 µg of protein in each well +/−DTT and transferred to membrane. Used 85RF45.1 as primary and HRP labeled rabbit anti-rat as secondary antibody. Used chemiluminescence for detection.

Figure 13:
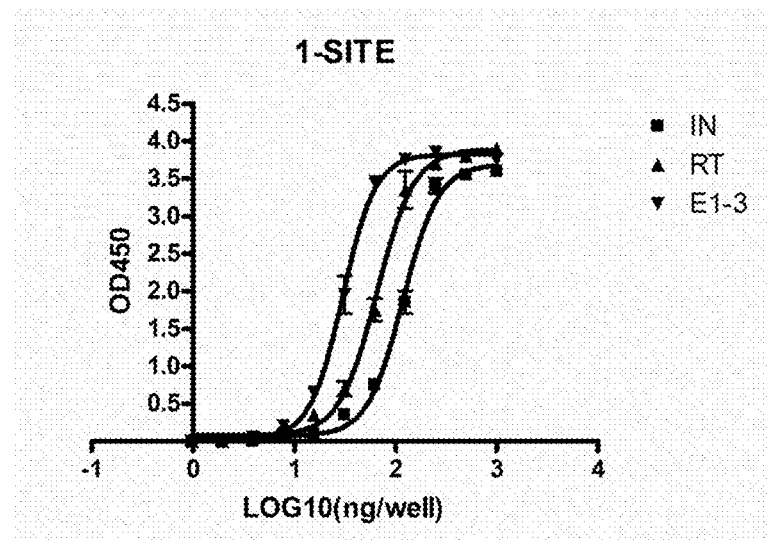

FIG. 13: 1-SITE ELISA of immunopurified R0-10C-6H. Protein was coated with two fold dilution of protein starting at 1000 ng. Anti-hexahistidine(C-term)-HRP was used as detecting antibody and TMB for developing.

Figure 14:
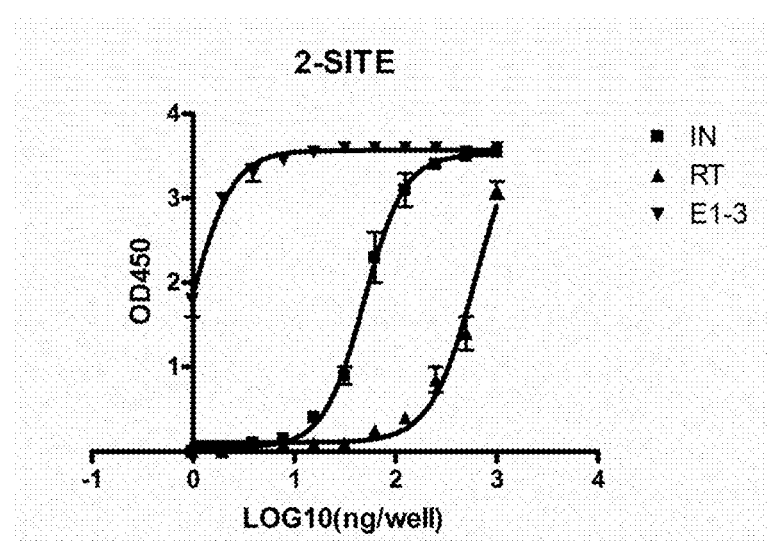

FIG. 14: 2-SITE ELISA of immunopurified R0-10C-6H. 250 ng of monoclonal antibody, 85RF45.1, was coated as capturing antibody and incubation with two fold dilution of protein starting at 1000 ng. Anti-hexahistidine(C-term)-HRP was used as detecting antibody and TMB for developing.

Figure 15:
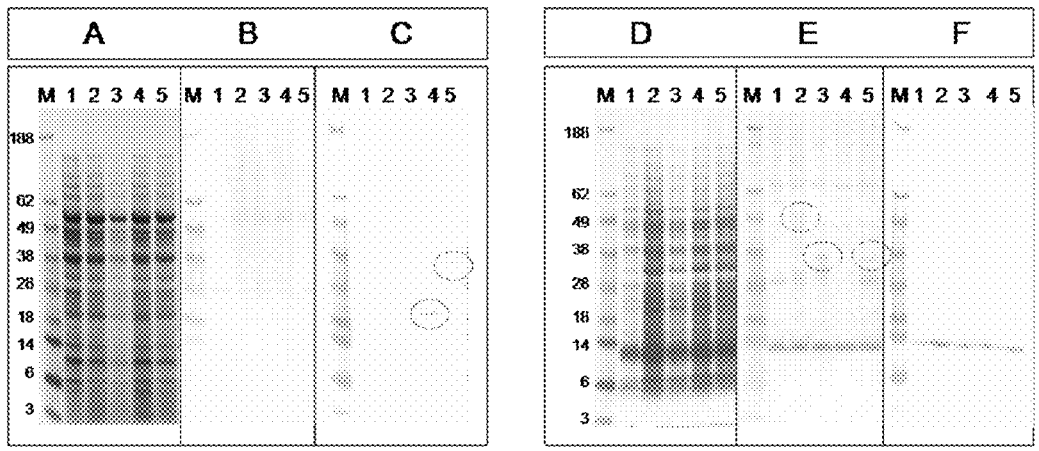

FIG. 15. Expression of Pfs45/48 fragments in pAMJ328: (A) SDS-PAGE of culture supernatants; (A-F) lane 1 MG1363 transformed with pAMJ328 (control), lanes 2-5 MG1363 transformed with pCNR5 (Pfs45/48_16C), pCNR6 (Pfs45/48_10C), pCNR7 (Pfs45/48_6N), and pCNR8 (Pfs45/48_10N), respectively. (B; C) Western blots of culture supernatants. (B) A polyclonal rabbit antibody against Pfs45/48 was used as primary antibody and a swine anti-rabbit antibody was used as secondary antibody. (C) A rat monoclonal antibody raised against the Pfs45/48 epitope V was used as primary antibodies and goat anti-rat IgG were used as secondary antibody. (D) SDS-PAGE of intracellular and cell-associated proteins. (E; F) Western blots of intracellular and cell-associated proteins. (E) Antibodies are as described in (B). (F) Antibodies are as described in (C).

Figure 16:
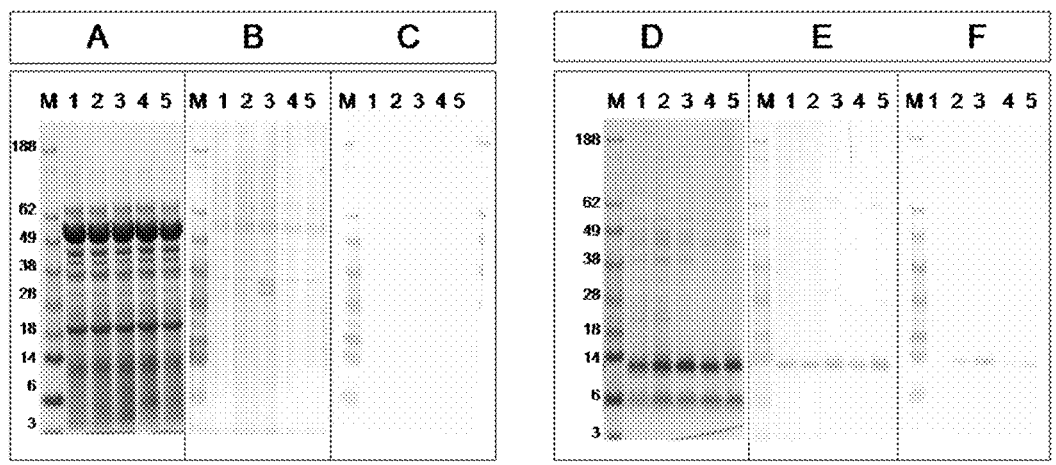

FIG. 16. Expression of Pfs45/48 fragments in pAMJ219: (A) SDS-PAGE of culture supernatants; (A-F) lane 1 MG1363 transformed with pAMJ219 (control), lanes 2-5 MG1363 transformed with pCNR9 (Pfs45/48_16C), pCNR10 (Pfs45/48_10C), pCNR11 (Pfs45/48_6N), and pCNR12 (Pfs45/48_10N), respectively. (B; C) Western blots of culture supernatants. (B) A polyclonal rabbit antibody against Pfs45/48 was used as primary antibody and a swine anti-rabbit antibody was used as secondary antibody. (C) A rat monoclonal antibody raised against the Pfs45/48 epitope V was used as primary antibody and goat anti-rat IgG was used as secondary antibody. (D) SDS-PAGE of intracellular and cell-associated proteins. (E; F) Western blots of intracellular and cell-associated proteins. (E) Antibodies are as described in (B). (F) Antibodies are as described in (C).

Figure 17:
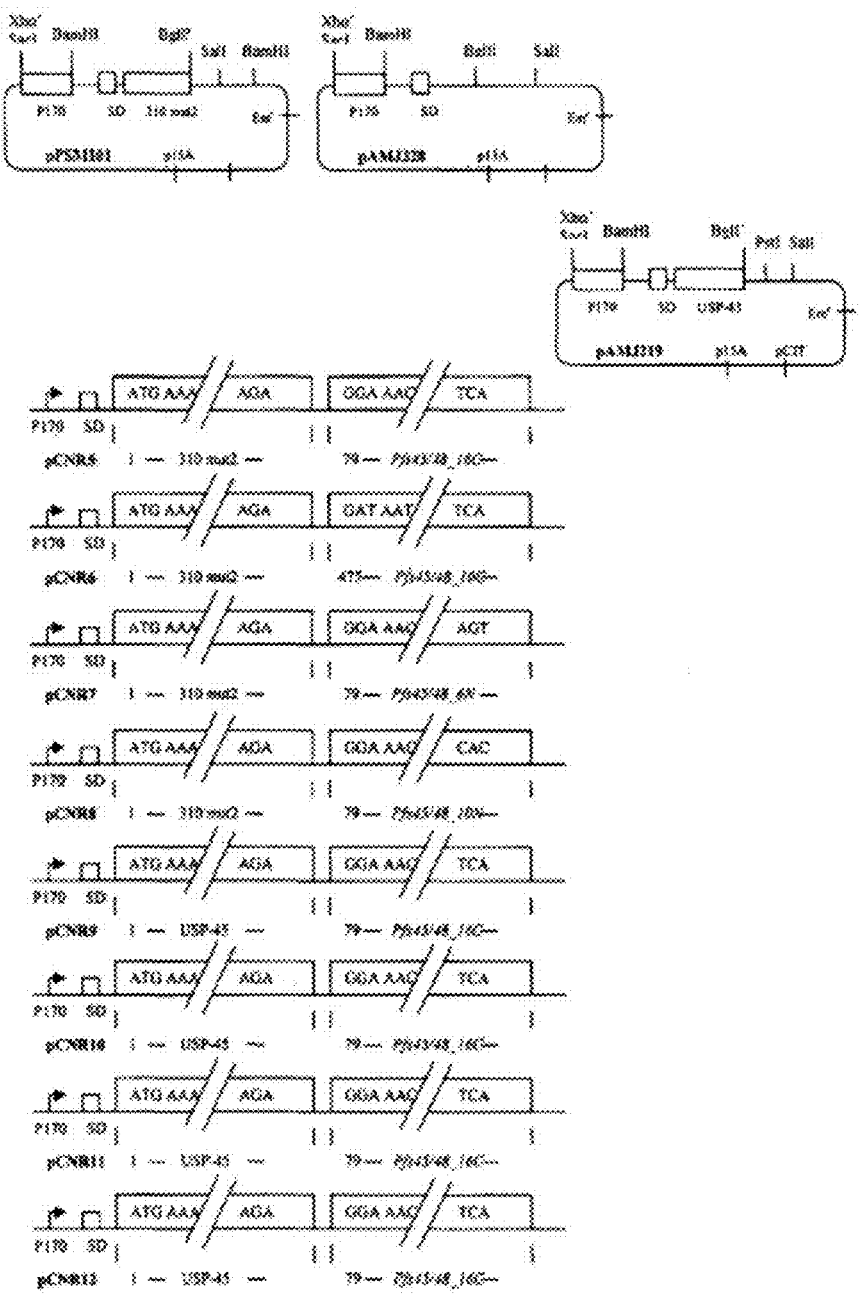

FIG. 17. Schematic representation of pPSM1013, pAMJ328 and, pAMJ219 and the expression constructs used in *L. lactis*. The position of vector-encoded restriction sites mentioned in the text, promoter P170, Shine-Dalgarno sequence (SD), 310mut2—and, USP-45 signal peptide are indicated. The nucleotide numbering of Pfs45/48 is relative to A in the ATG codon.

Figure 18:
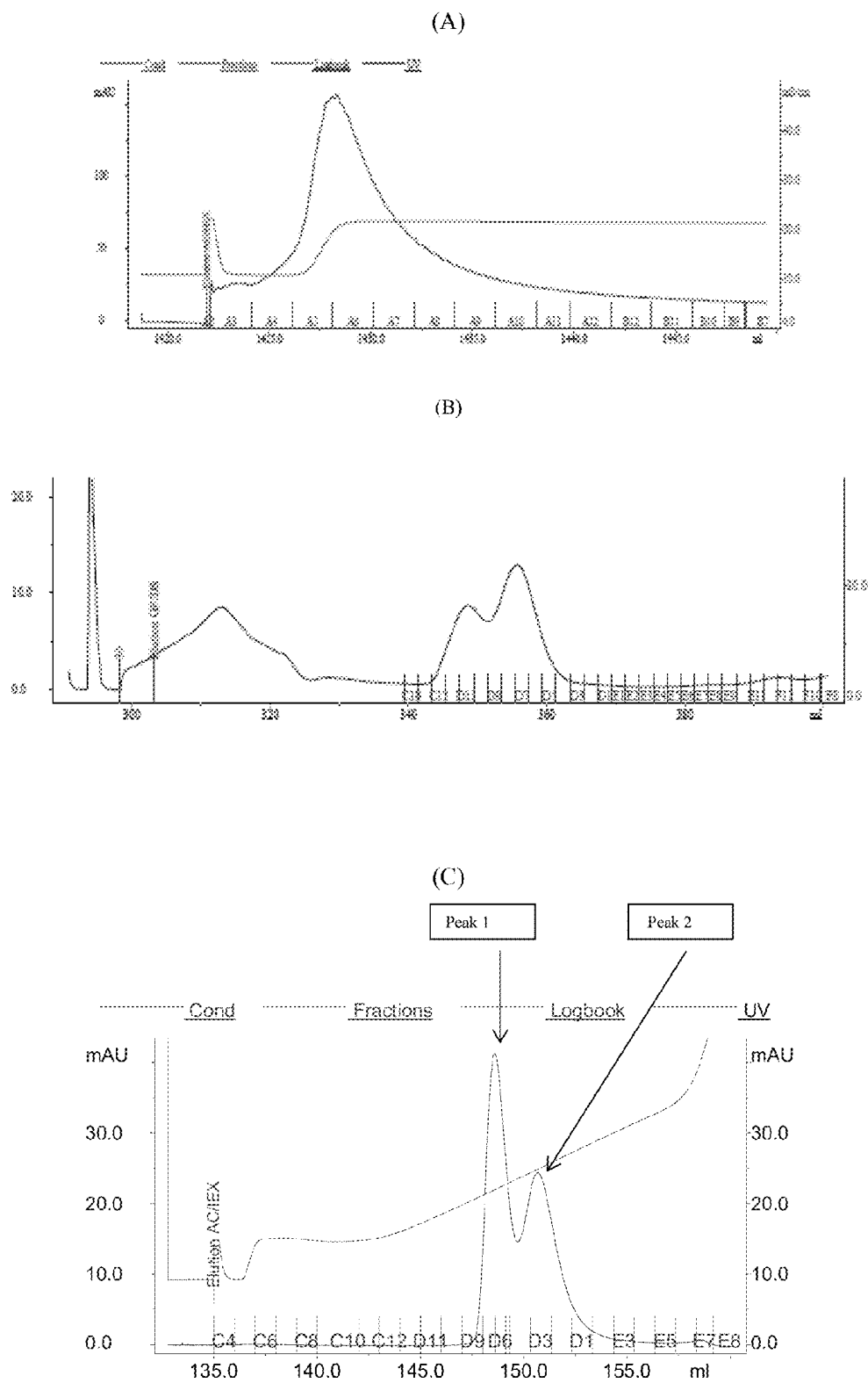

FIG. 18: Purification of RO-MSP3-6C-6H on (A) Step 1: a Hitrap crude FF Ni$^{++}$-column, (B) Step 2: size exclusion chromatography on a Superdex 200S column and (C) Step 3: ion exchange chromatography on a Q HP column.

EXAMPLES

Example 1

Expression of the R0-10C-6H in *L. lactis*

Construction of Plasmids

The 1.4 kb GLURP-R0 fragment (bp 79-1500) was amplified from gDNA from the *P. falciparum* line F32 using forward primer GA52 (ccagatctacaagtgagaatagaaataaacgaatc) and reverse primer GA4 (ctatacttgatataacctttttcagtattatctgcttcatgctcgcttttttccgattc).

The 0.8 kb 10C fragment of Pfs48/45 (bp 475-1282) was amplified from gDNA from the *P. falciparum* line 3D7 using forward primer GA12 (gaatcggaaaaaagcgagcatgaagcagataatactgaaaaggttatatcaagtatag) and reverse primer GA53 (ccagatctctaatggtgatgatggtgatgtgctgaatctatagtaactgtcatataag).

These two amplicons were fused inframe by amplifying 28 ng of the R0 fragment with 16 ng of the 10C fragment using primers GA52 and GA53. The fusion was then treated with amplicon polymerase for 15 minutes at 72° C. This topo treated fragment was ligated into the Topo vector pCR2.1 (Invitrogen) and the sequence was verified. The Topo product was digested with BglII and the resulting fragment cloned into a BglII digested pKBR11 vector yielding pLEA_5 (FIG. 2).

Protein Description

The recombinant protein (after processing of the $SP_{310}$ signal peptide) is composed of four vector encoded residues (AERS) followed by GLURP-R0$_{27-500}$, Pfs48/45-10C$_{159-428}$ and finally a six histidine C-terminus (R0-10C-6H). The theoretical molecular weight of the protein is 89.8 kDa of which 30.7 kDa originates from the 10C fragment. The pI and the extinction coefficient are calculated to be 4.9 and 2.7 (at 1%), respectively.

Production of Recombinant R0-10C-6H Protein

Working Cell Bank pLEA_5 was transformed into the *L. lactis* strain MG1363 and plated on YPDKN[E] selective plate. A colony was picked into 50 ml YPDKN[E] selective medium in a 50 ml tube. Culture was incubated overnight at 30° C. at 150 RPM. Following the overnight inoculation, 350 µl of the pre-culture is used to inoculate a 35 ml YPDKN[E] selective medium in a 50 ml tube. The culture is harvested (3.700 g, 15 min, 4° C.) at $OD_{600}$=1-3. Cells were washed in 20 ml cold YPDKN non-selective medium and spun down (3.700 g, 15 min, 4° C.). Finally, cells were resuspended in 10 ml non-selective cryopreservation solution YPDKNG (final cell density $OD_{600}$=12.5), and 200 µl is dispensed into 2 ml cryotubes (27 tubes), and stored in a box at −80° C.

Fermentation

Day 1

A Working Cell Bank vial was thawn and inoculated into 50 ml prewarmed YPD[3%] in a 50 ml tube. Pre-culture was grown @ 30° C. with gentle shaking (150 RPM).

Inoculation of fermentor containing 1 liter Basic LAB Medium[1] was done with syringe and needle through septum on the fermentor head-piece, when $OD_{600nm}$>0.6 (approx. 4-5 hours).

[1] 1% yeast extract, 2% Soya peptone, 3% dextrose, 0.1% potassium phosphate dibasic, 0.17% ammonium sulphate dibasic, 0.12% ammonium phosphate dibasic, 0.26% sodium citrate tribasic dihydrate, 0.025% magnesium sulphate heptahydrate, 0.0034% manganese sulphate monohydrate.

Fermentation @ 30° C.; 150 RPM; pH=6.5 (adjusted with 2 M sodium hydroxide), no DO electrode; no aeration; no feed Culture grows to $OD_{600nm}$ Induction of protein expression when culture reaches low pH.

Grown overnight.

Day 2

Cells were removed (10.000 g, 4° C., 10 min).

Estimated yield of recombinant protein is 25-50 mg/L (20 µl on an SDS-PAGE/Coomassie gel gives intensity between 0.5 and 1.0 µg BSA, (FIG. 3)).

Purification

Concentration and Diafiltration

Supernatant was concentrated to approx. 200 ml on a Quixstand system mounted with a 30.000 MWCO Hollow-Fiber Cartridge (GE Healthcare). Then the sample was diafiltrated against 1 liter 50 mM sodium phosphate (pH 7.0) (PBS-DFB1) and 1 liter 50 mM sodium phosphate (pH 7.0), 250 mM sodium chloride (PBS-DFB2), before being concentrated to approx. 125 ml. Sample was filtered (0.2 µm filter) and stored at 4° C. untill purification. Concentration and diafiltration was done at room temperature (20-22° C.). These procedures do not result in a major loss of recombinant protein.

Affinity Purification

Processed supernatant was mixed with 50 mM sodium phosphate (pH 7.0), 250 mM sodium chloride, 200 mM imidazole (PBS-ACEB) 9 to 1, to reach 20 mM imidazole in the sample. Purification of 6×his-tagged proteins was done on a ÄKTAxpress mounted with a 5 ml HistTrap HP (GE Healthcare). Briefly, column was equilibrated with 50 mM sodium phosphate (pH 7.0), 250 mM sodium chloride, 20 mM imidazole (PBS-ACBB), before loading sample. Unbound sample was washed out with PBS-ACBB. The column was then washed with 50 mM sodium phosphate (pH 7.0), 250 mM sodium chloride, 20 mM imidazole, 4/0.4 mM reduced glutathione/oxidized glutathione (PBS-ACRB) at 1 ml/min for 30 minutes, before a step elution with PBS-ACEB was done. All steps where run at 8° C. with a flow of 4 ml/min unless noted otherwise. Total yield of R0-10C-6H at this stage is up to 35 mg pr. liter culture.

Gel Filtration

The affinity purified protein is loaded on a 16/60 HiLoad S-200 column to separate the monomeric form of R0-10C-6H from the multimeric forms. It was run with 50 mM 50 mM Tris-HCl (pH 8.0), 100 mM sodium chloride (TBS-GFB). Approximately 40% was in the monomeric form (judged from the chromatogram (FIG. 4)), which gives a monomer yield in the affinity chromatography step of 6-14 mg pr. liter culture. However, due to the loss in the purification system (approx. 70% recovery) and because baseline separation was not achieved (approx. 60% is separated. Eg. fractions A10-B12 are monomeric (FIG. 5)), the actual recovery of the >95% pure monomeric R0-10C-6H after the gel filtration was approx. 6 mg pr. liter culture.

Ion-exchange Chromatography

Fractions containing the monomeric form of R0-10C-6H are pooled and purified on a 1 ml Q HP column (GE Healthcare). Briefly, column is equilibrated with 50 mM Tris-HCl (pH 8.0), 100 mM sodium chloride (TBS-IECB), before loading sample. Unbound sample was washed out with TBS-IECBB before a step elution with 50% 50 mM Tris-HCl (pH 8.0), 1 M sodium chloride (TBS-IECEB) is done. Final yield of >95% pure monomeric R0-10C-6H was approx. 5 mg pr. liter culture.

TABLE 3

Protein purification overview

| Step | Purity R0-10C-6H | Purity monomer | Amounts R0-10C-6H | Amounts monomer | Recovery (loss*) |
|---|---|---|---|---|---|
| Fermentation | 60% | 24% | 25-50 mg | 10-20 mg | 40% (60%) |
| Diafiltration | 60% | 24% | 25-50 mg | 10-20 mg | 40% (0%) |
| Affinity | >95% | 40% | 15-35 mg | 6-14 mg | 28% (30%) |
| Gel filtration | >95% | >95% | 3-6 mg | 3-6 mg | 12% (60%) |
| Ion-exchange | >95% | >95% | 2.5-5 mg | 2.5-5 mg | 10% (20%) |

*Loss is the estimated percentage of protein loss in given step. E.g. in the Fermentation step loss is the amount of the total R0-10C-6H which is in the multerimeric forms (judged from FIG. 5).

Example 2

Immunogenicity of Recombinant R0-10C-6H

The effect of PBS-ACRB washing step was tested by purifying R0-10C-6H with and without the PBS-ACRB washing step (without was done by exchanging PBS-ACRB with PBS-ACBB). The protein was tested in a 1-SITE and a 2-site ELISA to determine the potency of each sample. In the 1-SITE ELISA different concentrations of antigen was coated and detected with commercial HRP conjugated anti-hexahistidine antibody (FIG. 6). In the 2-SITE ELISA first the monoclonal antibody (85RF45.1) against Pfs48/45 was coated as capturing antibody on an ELISA plate, followed by blocking with skimmed milk. Different concentrations of antigen were applied and finally bound antigen was detected using commercial HRP conjugated anti-hexahistidine antibody (FIG. 7). The reactivity was more than two times higher with the PBS-ACRB wash compared to without (Table 4).

TABLE 4

| | EC50 (1-SITE) | EC50 (2-SITE) | POTENCY | REL. POTENCY (PBS-ACBB) |
|---|---|---|---|---|
| PBS-ACRB | 130.1 | 17.2 | 7.6 | 2.18 |
| PBS-ACBB | 139 | 40.1 | 3.5 | 1.00 |

Two groups of three rats each were immunized with different R0-10C-6H purifications adjuvanted with Freund's adjuvant. The groups were immunized 4 times according to immunization schedule (FIG. 8) with either 12.5 μg R0-10C-6H purified with the PBS-ACRB wash (Group 1), 25 μg R0-10C-6H purified without the PBS-ACRB wash (Group 2). The sera from the bleed after the last immunization ($3^{rd}$ bleed) were tested in a gametocyte ELISA (17). The level of reactivity towards gametocyte extract in Group 1 is higher compared to Group 2, with EC50 values of 417 and 54 fold serum dilution, respectively (FIG. 9). When comparing the individual sera from Group 1, some difference can be seen (FIG. 10).

Example 3

Immunopurification of Correctly Folded R0-10C-6H

To immunopurify correctly folded R0-10C-6H 1.8 mg of 85RF45.1 was coupled to a 1 ml NHS-activated HiTrap column (GE-HEalthcare, 17-0716-01), then IMAC purified R0-10C-6H from 200 ml supernatant (approx. 15 mg) was run through the column and bound protein was eluted according to manufacturers description. Fractions containing the desired protein were concentrated to 300 μl using a Vivaspin column. The input (IN), runthrough (RT) and pooled concentrated eluate (E1-3) were analysed by SDS-PAGE, Western blotting, and by 1-SITE and a 2-SITE ELISA (FIG. 11-14, respectively). The SDS-PAGE shows that the majority of the eluted protein is monomeric, but some smaller products have been co-purified. On the Western blot a very faint band can be seen in the input, while a clear band is visible in the E1-3 fractions. The relative potency of the correctly folded monomer compared to the input can be calculated from the relative EC50 value ($EC50_{E1-3}/EC50_{IN}$) in the 2-SITE ELISA divided by the same value in the 1-SITE ELISA (Table 6). The relative potency of the eluted sample is 13.07 and of the runthrough is 0.04, thus together with the Western blot it is evident that only correctly folded monomeric R0-10C-6H (E1-3) has been separated from the non-correctly folded monomeric and multimeric R0-10C-6H (RT). Calculating backwards using E1-3 as reference sample the input has a relative potency of 0.08 which equals 8% correctly folded R0-10C-6H.

TABLE 6

| | EC50 (1-SITE) | EC50 (2-SITE) | POTENCY | REL. POTENCY (IN) | REL. POTENCY (E1-3) |
|---|---|---|---|---|---|
| IN | 118.5 | 49.1 | 2.4 | 1.00 | 0.08 |
| RT | 65.6 | 619.6 | 0.1 | 0.04 | 0.00 |
| E1-3 | 30.1 | 1.0 | 31.5 | 13.07 | 1.00 |

Example 4

Expression of Individual Pfs48/45 Fragments

These experiments aimed to produce four overlapping Pfs48/45 fragments, 16C, 10C, 6N, and 10N as individual recombinant proteins in *Lactococcus lactis* (FIG. 1).

Expression of Pfs45/48 16C, 10C, 6N, and 10N in pAMJ328

Four different fragments of the Pfs45/48 gene were cloned inframe with the signal sequence SP310mut2 into the plasmid pAMJ328. The resultant plasmids, pCNR5 (Pfs45/48_16C), pCNR6 (Pfs45/48_10C), pCNR7 (Pfs45/48_6N), and pCNR8 (Pfs45/48_10N), were transformed into the *L. lactis* strain MG1363. MG1363 cells carrying the expression plasmids pCNR5, pCNR6, pCNR7, and pCNR8 were grown in *L. lactis* media containing 1% (w/v) glucose and 10 µg/ml of erythromycin. The growth of the cultures was monitored by measuring $OD_{600}$ every ½-1 h. Start $OD_{600}$'s were 0.04 and pH values were approximately 7.5. After 5½ h of growth, pH decreased to approximately 6.0 and 1 h later cells had entered the stationary growth phase ($OD_{600}$=~1.75). The expression and localization of rPfs45/48 constructs was analyzed by SDS-PAGE and Western blot of cultures harvested two hours after cells had entered the stationary growth phase. A polyclonal antiserum and a monoclonal antibody (85RF45.5) were used for rPfs45/48 detection. Proteins from 5 ml of each culture supernatant were separated on a 4-12% SDS-gel and stained with Coomassie brilliant blue (FIG. 15A). SDS-PAGE analysis of Pfs45/48 culture supernatants did not reveal the presence of any additional or more apparent protein bands when lanes were compared to the control in which MG1363 cells had been transformed with pAMJ328. Western blot analysis did, however, reveal expression and secretion of two of the prepared Pfs45/48 constructs: rPfs45/48_6N and rPfs45/48_10N (FIG. 15C; lanes 4-5). The molecular weight of the bands matches the theoretical weight of Pfs45/48_6N (17 kDa) and Pfs45/48_10N (32 kDa). Pfs45/48_6N and Pfs45/48_10N could only be detected with the monoclonal anti-Pfs45/48 epV antibody as no bands were revealed on the Western blot in which the polyclonal antiserum was used for detection (FIG. 15B). As the anti-Pfs45/48 epV antibody can not be used for detecting the 10C construct of Pfs45/48 it remains uncertain if expression and secretion also has been obtained for this construct. The level of Pfs45/48_6N and Pfs45/48_10N expressed and secreted is, however, estimated to be low. One possibility is that the rPfs45/48 fragments remain poorly, and/or are not at all secreted, when fused to the signal peptide SPmut2. This would lead to intracellular accumulation. Western blot analysis of intracellular and cell associated proteins did seem to show the presence of Pfs45/48_16C (46 kDa), Pfs45/48_10C (31 kDa), and Pfs45/48_10N (32 kDa) (FIG. 15D; lanes 2, 3, and 5). The faint protein bands matching these three Pfs45/48 constructs were only detected on the Western blot incubated with the polyclonal antiserum. From these analyses it seems as the general expression level of the four Pfs45/48 constructs prepared in pAMJ328 and expressed in *L. lactis* MG1363 is low.

Expression of Pfs45/48 16C, 10C, 6N, and 10N in pAMJ219

To investigate whether pAMJ219 could be a better expression vector for the production and secretion of Pfs45/48 constructs all four Pfs45/48 fragments were cloned into the Usp45 containing pAMJ219. The growth of *L. lactis* MG1363 transformed with pCNR9 (Pfs45/48_16C), pCNR10 (Pfs45/48_10C), pCNR11 (Pfs45/48_6N), and pCNR12 (Pfs45/48_10N) was similar to that of the control plasmid. However, we were unable to detect any of the rPfs45/48 fragments by SDS-PAGE or by Immuno blot analysis of secreted as well as cellular proteins were (FIG. 16).

Conclusion

Two different expression vectors (pAMJ328 and pAMJ219) were used for the production of four different but overlapping Pfs45/48 fragments in *L. lactis* MG1363. Expression of the Pfs45/48 constructs was only seen in pAMJ328 in which the constructs had been cloned inframe with the signal peptide SPmut2. No expression was detected when the constructs were cloned into pAMJ219. In general expression levels are low and only minor amounts of rPfs45/48_6N and rPfs45/48_10N are detectable in the culture medium. Pfs45/48_16C, Pfs45/48_10C and some of the rPfs45/48_10N seems to remain inside the cells.

Example 5

Materials and Methods

Bacterial Strains and Plasmids

*E. coli* Xl-1 blue (Stratagene), used as primary host for the construction and propagation of plasmids, was grown at 37° C. in Luria-Bertani (LB) broth supplemented with erythromycin (100 µg/ml). *L. Lactis* MG1363 (6) was grown at 30° C. in *L. lactis* media (1% (w/v) soya peptone, 1% (w/v) yeast extract, 0.1% (w/v) $MgSO_4 \times 7H_2O$, 0.1% (w/v) ascorbin acid, 3.8% (w/v) glycerophosphate) containing 1% (w/v) glucose and 10 µg/ml of erythromycin. Solidified LB and M17 media was supplemented with 250 and 5 µg/ml of erythromycin, respectively. The vector, pPSM1013 (FIG. 17), is a high-copy number expression plasmid based on the pAMβ1 replicon (26) containing multiple cloning sites allowing the construction of in-frame fusions with the modified and highly efficient secretion signal peptide SP310mut2 (20). The vector, pAMJ328 (FIG. 17) is derived from pPSM1013 by deleting all lacZ regulatory sequences to avoid transcription from the lac promoter and by creating a new cloning region devoid of the signal peptide (10). The vector, pAMJ219 (FIG. 17) is a low-copy number expression plasmid containing the minimal replicon pCIT (19). The multiple cloning site comprising BglII, PstI and SalI restrictionsites is located between by position 3572 and position 3589 allowing the construction of in-frame fusions with the signal peptide of Usp45 (the main secreted protein in *L. lactis*) efficiently recognized by the lactococcal secretion machinery. All vectors used in the study contain derivatives of the same promoter, P170, which is upregulated at low pH during the transition to stationary phase.

Construction of Plasmids Expressing Pfs48/45 16C, 10C, 6N and 10N in *L. lactis*

All plasmids were constructed in *E. coli* Xl-1-blue and transformed into *L. lactis*

MG1363 by electroporation as described (8). All plasmid constructions were verified by DNA sequencing. The key plasmids constructed in Example 4 are listed in FIG. 17.

pCNR1, pCNR2, pCNR3, and pCNR4

The sequence encoding the full length 16 cysteines (16C) mature protein (without the leader peptide and GPI addition sequence) was PCR amplified from the *P. falciparum* line 3D7 using the primers 5'-CACC <u>GGA TCC</u> GGA AAC AAT GAT TTT TGT AAG CCT AGC 3' (nucleotides 79-105) (counting from A in the ATG start codon of Pfs48/45) and 5'-<u>GGA TCC</u> CTA TGC TGA ATC TAT AGT AAC TGT CAT ATA AGC 3'(nucleotides 1255-1284). The sequence encoding the C-terminal 10 cysteine part (10C) was PCR amplified using the primers 5'-CACC <u>GGA TCC</u> GAT AAT ACT GAA AAG GTT ATA TCA AGT ATA (nucleotides 475-504) and 5'-<u>GGA TCC</u> CTA TGC TGA ATC TAT AGT AAC TGT CAT ATA AGC 3' (nucleotides 1255-1284). The sequence encoding the N-terminal 6 cysteine part (6N) was amplified using the primers 5'-CACC <u>GGA TCC</u> GGA AAC AAT GAT TTT TGT AAG CCT AGC 3' (nucleotides 79-105) and 5'-<u>GGA TCC</u> CTA AGC ACT TCT CCC TTC TAT ACT TGA 3' (nucleotides 496-519). Finally, the sequence encoding the N-terminal 10 cysteine part (10N) was amplified using the primers 5'-CAC C GGA TCC GGA AAC AAT GAT TTT TGT AAG CCT AGC 3' (nucleotides 79-105) and 5'-GGA TCC CTA TCC GTG TAT GAC TTT TTT TTC ATA 3' (nucleotides 868-891). The BamHI restriction sites in the primers are underlined and the artificial STOP codons are in bold. Following digestion with BamHI (New England Biolabs), the amplified DNA fragments were inserted into (i): BglII digested pPSM1013, resulting in the plasmids pCNR1 (Pfs45/48_16C), pCNR2 (Pfs45/48_10C), pCNR3 (Pfs45/48_6N), and, pCNR4 (Pfs45/48_10N) or (ii) BglII digested pAMJ219, resulting in the plasmids pCNR9 (Pfs45/48_16C), pCNR10 (Pfs45/48_10C), pCNR11 (Pfs45/48_6N), and, pCNR12 (Pfs45/48_10N).

pCNR5, pCNR6, pCNR7, and, pCNR8

Plasmids pCNR1, pCNR2, pCNR3, and, pCNR4 were digested with BamHI and SalI, and the resulting DNA fragments containing the Pfs45/48-16C, -10C, -6N and, -10N inserts, were cloned into BamHI-SalI digested pAMJ328.

Culture Conditions

All flask experiments were carried out at 30° C. without shaking or an active supply of air. Each flask, containing 300 ml *L. lactis* media supplemented with 1% (w/v) glucose and 10 ng/ml of erythromycin, were inoculated with 3 ml of a fresh overnight culture grown in the same medium. Cultures were grown until approximately two h after the stationary phase had been reached. Growth was monitored by measuring the $OD_{600}$ every ½-1 h.

Product Analysis, SDS-PAGE, and Immunoblotting

For product analysis, 5 ml of *L. lactis* cultures collected 2 h after cells had entered the stationary phase were harvested by centrifugation at 4° C. and 8000×g for 5 min. The culture supernatants and cells were processed separately. Supernatants were filtered on 0.2-µm-pore-size filters and trichloroacetic acid (TCA) (5% final concentration) was added to the culture filtrate and incubated at 4° C. over night. Following centrifugation (4° C. and 15.000×g for 20 min) the resulting pellets were redissolved in 15 µl of SDS sample buffer. Intracellular and cell-associated proteins were prepared by the method of Le Loir et al. (14). Briefly, cell pellets were washed once with 1 ml of ice-cold TES (25% sucrose, 1 mM EDTA, 50 mM Tris-HCL; pH 8), resuspended in TES and precipitated with TCA (10% final concentration). Cell pellets were then washed once with 1 ml of ice cold acetone, dried, and resuspended in 70 µl of TES containing lysozyme (1 mg/ml). After 30 min of incubation at 37° C., cells were lysed with 30 µl of 20% SDS. SDS-PAGE was performed according to Laemmli (13) using the Xcell SureLock mini-cell system (Invitrogen). Samples were boiled for 5 min and separated on 4-12% Tris-glycine gels from Invitrogen according to the manufacturer. The proteins were either Coomassie stained or electroblotted onto nitrocellulose membranes using the Xcell II blot module (Invitrogen). Nitrocellulose membranes were blocked in Tris buffer (50 mM Tris-HCl [pH 8], 0.15 M NaCl) containing 1% BSA. A polyclonal serum raised against Pfs45/48 in rabbits (dilution 1:100) and rat monoclonal antibodies raised against the Pfs45/48 epitope V (code nr: 85RF45.5) (dilution 1:1000) was kindly provided by N. Outchkourov, Radboud University, The Netherlands Immunodetection was performed with alkaline-phosphatase-coupled swine anti-rabbit antibodies (dilution 1:1000) (Dako) and alkaline-phosphatase-coupled goat anti-rat antibodies (dilution 1:30.000) (Sigma).

Example 6

Fusions between GLURP-R0 (R0), MSP3, and Fragments of Pfs48/45

In an attempt to increase the yield of correctly folded Pfs48/45 protein, a range of new fusions between GLURP-R0 (R0), MSP3, and carefully selected fragments of Pfs48/45 containing either 10 cysteine (10C) or 6 cysteine (6C) residues were screened in the 2-sided ELISA after fermentation at the 1 L scale.

The Pfs48/45 fragments where selected so they contained epitope I (domaine III in FIG. 1) or the epitope I, II and III (domaine II & III) e.g. the 6C homologues (6Ca, 6Cb, 6Cc, 6Cd) and the 10C homologues (10Ca, 10Cb, 10Cc, 10Cd) in table 7. The amino acid sequence (AA) and the nucleic acid sequence (bp) of the homologues in table 7 refer to the sequence numbers in SEQ ID NO 3 and 4 respectively.

TABLE 7

Various homologues of 10C and 6C fragments fused in frame to either GLURP.R0 or GLURP.R0-MSP3

| Name | Start in Pfs48/45 (AA) | Start in Pfs48/45 (bp) | Stop in Pfs48/45 (AA) | Stop in Pfs48/45 (bp) |
|---|---|---|---|---|
| 10Ca | D159 | 475 | A428 | 1284 |
| 10Cb | D159 | 475 | A419 | 1257 |
| 10Cc | P200 | 598 | A428 | 1284 |
| 10Cd | P200 | 598 | A419 | 1257 |
| 6Ca | K287 | 859 | A419 | 1284 |
| 6Cb | K287 | 859 | A419 | 1257 |
| 6Cc | A292 | 871 | A419 | 1284 |
| 6Cd | A292 | 871 | A419 | 1257 |

The yield of the culture supernatant of the Pfs48/45 fragments/homologues fused to GLURP.R0-MSP3 is given in table 8

TABLE 8

| Name | Yield mg/L |
|---|---|
| 10Ca | 39 |
| 10Cb | 38 |
| 10Cc | 56 |
| 10Cd | 30 |
| 6Ca | 32 |
| 6Cb | 43 |
| 6Cc | 50 |
| 6Cd | 26 |

One of these, R0.MSP3.6 Cc proved to have enhanced intrinsic structural properties allowing for better protein folding and a high yield. R0.MSP3.6 Cc, produces 30-60 mg recombinant protein per L culture supernatant, of which ~35% is correctly folded. Preliminary data suggests that it is feasible to purify 100% correctly folded R0.6 Cc using conventional purification methods. The purification was done in three steps. Step 1: Purification on a Hitrap crude FF $Ni^{++}$-column where raw culture supernatant was adjusted to pH 7.4, applied to the column, and eluted with 500 mM Imidazole; binding efficiency is approx 65% (FIG. 18A, table 9). Step 2: Size exclusion chromatography on a Superdex 200S. The eluate from step 1 was applied to a Superdex 200S column and eluted in two overlapping peaks. Peak 1 contains predominantly multimers and peak 2 contains predominantly monomer. Approximately 55% of peak 2 is correctly folded (FIG. 18B, table 9). Step 3: Ion exchange chromatography on Q HP. The monomer fraction from step 2 was applied to a Q HP column and bound protein was eluted with a gradient of NaCl in the column buffer. Two overlapping peaks are apparent. Peak 1 contains ~100% correctly folded monomer (FIG. 18C, table 9).

This represents a significant increase in correctly folded protein species as compared to R0.10C.

TABLE 9

Potency of R0.MSP3.6Cc at each step.

| Sample | Total yield of R0.6Cc (mg) | Potency[a] (%) | Yield of correctly folded R0.6Cc (mg) |
|---|---|---|---|
| Culture supernatant | 50 | 35 | 17.5 |
| Step 1 | 35 | 35 | 12.6 |
| Step 2 (peak 2) | 9 | 55 | 5 |
| Step 3 (peak 1) | 4.5 | 100 | 4.5 |

[a]The 100% correctly folded R0.10C is used as a reference for estimating the amount of correctly folded R0.6Cc. By using this reference we assume that the affinity of mAb 45.1 for epitope 1 encoded by R0.10C is similar to the affinity for epitope 1 encoded by the R0.6Cc construct.

Example 7

Production of other CYRP Proteins

In addition to the described Pfs48/45 protein fusions, we have created a set of protein fusions between GLURP.R0 and cysteine-rich domains of Var2CSA, Var4, and EBA175. As for R0.10C and R0.6 Cc, these chimera accumulate in *L. lactis* culture supernatants as monomeric recombinant proteins.

REFERENCES

1. Bredmose, L., S. M. Madsen, A. Vrang, P. Ravn, M. G. Johnsen, J. Glenting, J. Arnau, and H. Israelsen. 2001. Development of a heterologous geneexpression system for use in *Lactococcus lactis*, p. 269-275. In O.-W. Merten, D. Mattanovich, C. Lang, G. Larsson, P. Neubauer, D. Porro, P. Postma, J. Teixeira de Mattos, and J. A. Cole (ed.), Recombinant Protein Production with Prokaryotic and Eukaryotic Cells. Kluwer Academic Publishers.
2. Carter, R. 2001. Transmission blocking malaria vaccines. Vaccine 19:2309-2314.
3. Carter, R., G. Bushell, A. Saul, P. M. Graves, and C. Kidson. 1985. Two apparently nonrepeated epitopes on gametes of *Plasmodium falciparum* are targets of transmission-blocking antibodies. Infect Immun 50:102-106.
4. Carter, R., P. M. Graves, D. B. Keister, and I. A. Quakyi. 1990. Properties of epitopes of Pfs 48/45, a target of transmission blocking monoclonal antibodies, on gametes of different isolates of *Plasmodium falciparum*. Parasite Immunol 12:587-603.
5. Cohen, S., A. McGregor, and S. Carrington. 1961. Gamma globulin and acquired immunity to human malaria. Nature 192:733-737.
6. Gasson, M. J. 1983. Plasmid complements of *Streptococcus lactis* NCDO 712 and other lactic streptococci after protoplast-induced curing. J Bacteriol 154:1-9.
7. Gosselin, E. J., K. Wardwell, D. R. Gosselin, N. Alter, J. L. Fisher, and P. M. Guyre. 1992. Enhanced antigen presentation using human Fc gamma receptor (monocyte/macrophage)-specific immunogens. J. Immunol. 149:3477-3481.
8. Holo, H., and I. F. Nes. 1995. Transformation of *Lactococcus* by electroporation. Methods Mol Biol 47:195-199.
9. Israelsen, H., S. M. Madsen, A. Vrang, E. B. Hansen, and E. Johansen. 1995. Cloning and partial characterization of regulated promoters from *Lactococcus lactis* Tn917-lacZ integrants with the new promoter probe vector, pAK80. Appl. Environ. Microbiol. 61:2540-2547.
10. Israelsen, H., S. M. Madsen, A. Vrang, E. B. Hansen, and E. Johansen. 1995. Cloning and partial characterization of regulated promoters from *Lactococcus lactis* Tn917-lacZ integrants with the new promoter probe vector, pAK80. Appl Environ Microbiol 61:2540-2547.
11. Kaslow, D. C. 2002. Transmission-blocking vaccines. Chem Immunol 80:287-307.
12. Kaslow, D. C., I. C. Bathurst, and P. J. Barr. 1992. Malaria transmission-blocking vaccines. Trends Biotechnol 10:388-391.
13. Laemmli, U. K. 1970. Cleavage of structural proteins during the assembly of the head of bacteriophage T4. Nature 227:680-685.
14. Le Loir, Y., A. Gruss, S. D. Ehrlich, and P. Langella. 1998. A nine-residue synthetic propeptide enhances secretion efficiency of heterologous proteins in *Lactococcus lactis*. J Bacteriol 180:1895-1903.
15. Lowrie, D. B., R. E. Tascon, V. L. Bonato, V. M. Lima, L. H. Faccioli, E. Stavropoulos, M. J. Colston, R. G. Hewinson, K. Moelling, and C. L. Silva. 1999. Therapy of tuberculosis in mice by DNA vaccination. Nature 400:269-271.
16. Madsen, S. M., J. Arnau, A. Vrang, M. Givskov, and H. Israelsen. 1999. Molecular characterization of the pH-inducible and growth phase-dependent promoter P170 of *Lactococcus lactis*. Mol. Microbiol. 32:75-87.
17. Outchkourov, N., A. Vermunt, J. Jansen, A. Kaan, W. Roeffen, K. Teelen, E. Lasonder, A. Braks, M. van de Vegte-Bolmer, L. Y. Qiu, R. Sauerwein, and H. G. Stunnenberg. 2007. Epitope analysis of the malaria surface antigen pfs48/45 identifies a subdomain that elicits transmission blocking antibodies. J Biol Chem 282:17148-17156.
18. Outchkourov, N. S., W. Roeffen, A. Kaan, J. Jansen, A. Luty, D. Schuiffel, G. J. van Gemert, M. van de Vegte-Bolmer, R. W. Sauerwein, and H. G. Stunnenberg. 2008. Correctly folded Pfs48/45 protein of *Plasmodium falciparum* elicits malaria transmission-blocking immunity in mice. Proc Natl Acad Sci USA 105:4301-4305.
19. Pedersen, M. L., K. R. Arnved, and E. Johansen. 1994. Genetic analysis of the minimal replicon of the *Lactococcus lactis* subsp. *lactis* biovar diacetylactis citrate plasmid. Mol Gen Genet 244:374-382.
20. Ravn, P., J. Arnau, S. M. Madsen, A. Vrang, and H. Israelsen. 2003. Optimization of signal peptide SP310 for heterologous protein production in *Lactococcus lactis*. Microbiology 149:2193-2201.
21. Rener, J., P. M. Graves, R. Carter, J. L. Williams, and T. R. Burkot. 1983. Target antigens of transmission-blocking immunity on gametes of *plasmodium falciparum*. J Exp Med 158:976-981.
22. Roeffen, W., T. Lensen, B. Mulder, K. Teelen, R. Sauerwein, J. Van Druten, W. Eling, J. H. Meuwissen, and P. J. Beckers. 1995. A comparison of transmission-blocking activity with reactivity in a *Plasmodium falciparum* 48/45-kD molecule-specific competition enzyme-linked immunosorbent assay. Am J Trop Med Hyg 52:60-65.
23. Roeffen, W., B. Mulder, K. Teelen, M. Bolmer, W. Eling, G. A. Targett, P. J. Beckers, and R. Sauerwein. 1996. Association between anti-Pfs48/45 reactivity and *P. falciparum* transmission-blocking activity in sera from Cameroon. Parasite Immunol 18:103-109.
24. Roeffen, W., K. Teelen, J. van As, M. vd Vegte-Bolmer, W. Eling, and R. Sauerwein. 2001. *Plasmodium falciparum*: production and characterization of rat monoclonal antibodies specific for the sexual-stage Pfs48/45 antigen. Exp Parasitol 97:45-49.
25. Russel, P. F., and M. B N. 1942. The immunization of fowls against mosquito-borne *Plasmodium* gallinaceum by injections of serum and of inactivated homologous sporozoites. J Exp Med 76:477-495.

26. Simon, D., and A. Chopin. 1988. Construction of a vector plasmid family and its use for molecular cloning in *Streptococcus lactis*. Biochimie 70:559-566.
27. Targett, G. A., P. G. Harte, S. Eida, N. C. Rogers, and C. S. Ong. 1990. *Plasmodium falciparum* sexual stage antigens: immunogenicity and cell-mediated responses. Immunol Lett 25:77-81.
28. Theisen, M., S. Soe, K. Brunstedt, F. Follmann, L. Bredmose, H. Israelsen, S. M. Madsen, and P. Druilhe. 2004. A *Plasmodium falciparum* GLURP-MSP3 chimeric protein; expression in *Lactococcus lactis*, immunogenicity and induction of biologically active antibodies. Vaccine 22:1188-1198.
29. van Dijk, M. R., C. J. Janse, J. Thompson, A. P. Waters, J. A. Braks, H. J. Dodemont, H. G. Stunnenberg, G. J. van Gemert, R. W. Sauerwein, and W. Eling. 2001. A central role for P48/45 in malaria parasite male gamete fertility. Cell 104:153-164.
30. Vermeulen, A. N., T. Ponnudurai, P. J. Beckers, J. P. Verhave, M. A. Smits, and J. H. Meuwissen. 1985. Sequential expression of antigens on sexual stages of *Plasmodium falciparum* accessible to transmission-blocking antibodies in the mosquito. J Exp Med 162:1460-1476.
31. Vermeulen, A. N., W. F. Roeffen, J. B. Henderik, T. Ponnudurai, P. J. Beckers, and J. H. Meuwissen. 1985. *Plasmodium falciparum* transmission blocking monoclonal antibodies recognize monovalently expressed epitopes. Dev Biol Stand 62:91-97.
32. WHO. 1999. Malaria, 1982-97. Weekly Epidemiol Record 74:265-272.

---

The invention claimed is:

1. A method of producing a cysteine-rich protein, comprising expressing a cysteine-rich protein fused to a glutamate-rich protein in a lactic acid bacterial system, where the formation of monomeric fusion protein is enhanced by controlling the redox potential in the lactic acid bacterial production medium by adding the reduced form of a sulfhydryl containing compound to a concentration of 5-20 mM.

2. The method according to claim 1, where the glutamate-rich protein is GLURP or part of GLURP.

3. The method according to claim 1 where the lactic acid bacterium is *Lactococcus lactis*.

4. The method according to claim 1 where said sulfhydryl containing compound is L-cysteine.

5. The method according to claim 1 where the cysteine-rich protein originates from *Plasmodium falciparum*.

6. The method according to claim 5 where the cysteine-rich protein is Pfs48/45, Pfs25, Pfs230, Pfs47, EBA175, a member of the PfEMP1, RIFIN or STEVOR protein families or a fragment or a homologue hereof.

7. The method according to claim 1 where the correct folding of the cysteine rich protein is enhanced by addition of reduced and oxidized forms of a sulfhydryl containing compound capable of reducing or oxidixing cystines or cysteines in proteins to the buffer during the down-stream processing.

8. The method according to claim 7 where 1-10 mM of the reduced form and 0.1-5 mM of the oxidized form of the sulfhydryl containing compound is added.

9. The method according to claim 4 wherein L-cysteine is added to the medium to a concentration of about 10 mM.

10. The method according to claim 7, wherein said sulfhydryl containing compound is L-cysteine, DTT, glutathione, TCEP, or cysteamine.

11. The method according to claim 7, wherein said sulfhydryl containing compound is L-cysteine.

12. A method of producing a cysteine-rich protein, comprising expressing a cysteine-rich protein fused to a glutamate-rich protein in a lactic acid bacterial system, where the formation of monomeric fusion protein is enhanced by controlling the redox potential in the lactic acid bacterial production medium by adding the reduced form of L-cysteine, DTT, glutathione, TCEP, or cysteamine to a concentration of 5-20 mM.

13. The method according to claim 12, wherein said reduced form of L-cysteine, DTT, glutathione, TCEP, or cysteamine is added to the medium to a concentration of about 10 mM.

14. The method according to claim 13, wherein L-cysteine is added to the medium to a concentration of about 10 mM.

15. The method according to claim 12, where the glutamate-rich protein is GLURP or part of GLURP.

16. The method according to claim 12, where the lactic acid bacterium is *Lactococcus lactis*.

17. The method according to claim 12, where the cysteine-rich protein originates from *Plasmodium falciparum*.

18. The method according to claim 17, where the cysteine-rich protein is Pfs48/45, Pfs25, Pfs230, Pfs47, EBA175, a member of the PfEMP1, RIFIN or STEVOR protein families or a fragment or a homologue hereof.

19. The method according to claim 12, where the correct folding of the cysteine rich protein is enhanced by addition of reduced and oxidized forms of a small sulfhydryl containing compound capable of reducing or oxidixing cystines or cysteines in proteins to the buffer during the down-stream processing.

20. The method according to claim 19, where 1-10 mM of the reduced form and 0.1-5 mM of the oxidized form of the sulfhydryl containing compound is added.

* * * * *